(12) United States Patent
Laufer et al.

(10) Patent No.: US 7,713,277 B2
(45) Date of Patent: May 11, 2010

(54) TISSUE RECONFIGURATION

(75) Inventors: Michael D. Laufer, Menlo Park, CA (US); Jeffrey C. Cerier, Franklin, MA (US); Amos Cruz, Franklin, MA (US); Jonathan O'Keefe, Scituate, MA (US); Richard Andrews, Lincoln, RI (US); Ram Chuttani, Dover, MA (US); Vincent A. Puicci, Jr., Spencer, MA (US); Michael Barenboym, Ashland, MA (US); Neal H. Marshall, Bolton, MA (US); Randall B. Chinnock, Sturbridge, MA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1177 days.

(21) Appl. No.: 10/828,469

(22) Filed: Apr. 21, 2004

(65) Prior Publication Data
US 2004/0194790 A1 Oct. 7, 2004

Related U.S. Application Data

(63) Continuation of application No. 09/859,579, filed on May 18, 2001, now Pat. No. 6,821,285, which is a continuation-in-part of application No. 09/574,424, filed on May 19, 2000, now Pat. No. 6,494,888, which is a continuation-in-part of application No. 09/520,273, filed on Mar. 7, 2000, now Pat. No. 6,663,639, and a continuation-in-part of application No. 09/519,945, filed on Mar. 7, 2000, now Pat. No. 6,506,196.

(60) Provisional application No. 60/140,492, filed on Jun. 22, 1999.

(51) Int. Cl.
*A61B 17/08* (2006.01)

(52) U.S. Cl. .................................. 606/153

(58) Field of Classification Search ................ 606/142, 606/151, 153, 213, 215, 219, 220; 128/898; 227/175.1, 66, 67
See application file for complete search history.

(56) References Cited

U.S. PATENT DOCUMENTS 663,639 A 12/1900 Rand (Continued)

FOREIGN PATENT DOCUMENTS

EP 0 480 428 4/1992

(Continued)

OTHER PUBLICATIONS

International Search Report dated Oct. 16, 2000.

(Continued)

*Primary Examiner*—Julian W Woo
(74) *Attorney, Agent, or Firm*—Nutter McClennen & Fish LLP

(57) ABSTRACT

A medical instrument for engaging tissue includes a flexible shaft, a tissue piercing coil at a distal portion of the shaft, and a tissue stabilizer positioned over the shaft and biased in a distal direction such that as the tissue piercing coil enters tissue, the tissue stabilizer is urged against a surface of the tissue. A medical instrument for reconfiguring tissue includes a flexible shaft defining a lumen housing actuating controls, and a distal actuating assembly with a sealing portion configured to substantially seal the shaft lumen from contact with bodily fluids. A cartridge assembly includes first and second members configured for releasable attachment to a medical instrument, and a holder configured to receive the first and second members and to be released from the first and second members upon action of the first and second members attaching to the medical instrument.

20 Claims, 48 Drawing Sheets

U.S. PATENT DOCUMENTS

| | | | |
|---|---|---|---|
| 1,343,289 A | 6/1920 | Suchy | |
| 1,548,250 A | 8/1925 | Bobner | |
| 2,104,885 A | 1/1938 | robbins | |
| 2,199,025 A | 4/1940 | Conn | |
| 3,399,432 A | 9/1968 | Merser | |
| 3,470,875 A | 10/1969 | Johnson | |
| 3,551,987 A | 1/1971 | Wilkinson | |
| 3,636,594 A | 1/1972 | Faivre et al. | |
| 3,638,653 A | 2/1972 | Berry | |
| 3,734,375 A | 5/1973 | Bone et al. | |
| 3,749,085 A | 7/1973 | Willson et al. | |
| 3,842,840 A | 10/1974 | Schweizer | |
| 3,875,648 A | 4/1975 | Bone | |
| 3,900,925 A | 8/1975 | La Torraca | |
| 3,901,244 A | 8/1975 | Schweizer | |
| 3,933,291 A | 1/1976 | Stephenson | |
| 3,946,740 A | 3/1976 | Bassett | |
| 4,006,747 A | 2/1977 | Kronenthal et al. | |
| 4,014,492 A | 3/1977 | Rothfuss | |
| 4,043,504 A | 8/1977 | Hueil et al. | |
| 4,144,890 A | 3/1979 | Hess | |
| 4,164,225 A | 8/1979 | Johnson et al. | |
| 4,168,703 A | 9/1979 | Kenigsberg | |
| 4,210,148 A | 7/1980 | Stivala | |
| 4,229,930 A | 10/1980 | Ostermaier | |
| 4,235,238 A | 11/1980 | Ogiu et al. | |
| 4,265,226 A | 5/1981 | Cassimally | |
| 4,375,866 A | 3/1983 | Giersch et al. | |
| 4,399,810 A | 8/1983 | Samuels et al. | |
| 4,407,286 A | 10/1983 | Noiles et al. | |
| 4,448,194 A | 5/1984 | DiGiovanni et al. | |
| 4,471,781 A | 9/1984 | DiGiovanni et al. | |
| 4,500,024 A | 2/1985 | DiGiovanni et al. | |
| 4,506,670 A | 3/1985 | Crossley | |
| 4,573,469 A | 3/1986 | Golden et al. | |
| 4,585,153 A | 4/1986 | Failla et al. | |
| 4,586,502 A | 5/1986 | Bedi et al. | |
| 4,591,085 A | 5/1986 | Di Giovanni et al. | |
| 4,605,004 A | 8/1986 | Di Giovanni et al. | |
| 4,606,345 A | 8/1986 | Dorband et al. | |
| 4,607,638 A | 8/1986 | Crainich | |
| 4,627,437 A | 12/1986 | Bedi et al. | |
| 4,635,637 A | 1/1987 | Schreiber | |
| 4,649,938 A | 3/1987 | McArthur | |
| 4,653,496 A | 3/1987 | Bundy et al. | |
| 4,665,906 A | 5/1987 | Jervis | |
| 4,669,473 A | 6/1987 | Richards et al. | |
| 4,696,300 A | 9/1987 | Anderson | |
| 4,705,040 A | 11/1987 | Mueller et al. | |
| 4,724,840 A | 2/1988 | McVay et al. | |
| 4,736,746 A | 4/1988 | Anderson | |
| 4,741,336 A | 5/1988 | Failla et al. | |
| 4,753,469 A | 6/1988 | Hiscott | |
| 4,809,695 A | 3/1989 | Gwathmey et al. | |
| 4,841,888 A | 6/1989 | Mills et al. | |
| 4,862,359 A | 8/1989 | Trivedi et al. | |
| 4,880,015 A | 11/1989 | Nierman | |
| 4,887,612 A | 12/1989 | Esser et al. | |
| 4,890,615 A | 1/1990 | Caspari et al. | |
| 4,935,027 A | 6/1990 | Yoon | |
| 5,015,249 A | 5/1991 | Nakao et al. | |
| 5,037,021 A | 8/1991 | Mills et al. | |
| 5,037,433 A | 8/1991 | Wilk et al. | |
| 5,067,957 A | 11/1991 | Jervis | |
| 5,076,285 A | 12/1991 | Hess et al. | |
| 5,080,663 A | 1/1992 | Mills et al. | |
| 5,088,979 A | 2/1992 | Filipi et al. | |
| 5,147,373 A | 9/1992 | Ferzli | |
| 5,174,487 A | 12/1992 | Rothfuss et al. | |
| 5,190,546 A | 3/1993 | Jervis | |
| 5,219,359 A | 6/1993 | McQuilkin et al. | |
| 5,222,963 A | 6/1993 | Brinkerhoff et al. | |
| 5,230,344 A | 7/1993 | Ozdamar et al. | |
| 5,254,126 A | 10/1993 | Filipi et al. | |
| 5,289,963 A | 3/1994 | McGarry et al. | |
| 5,290,296 A | 3/1994 | Phillips | |
| 5,309,923 A | 5/1994 | Leuchter et al. | |
| 5,324,325 A | 6/1994 | Moaddeb | |
| 5,331,969 A | 7/1994 | Silberstein | |
| 5,336,263 A | 8/1994 | Ersek | |
| 5,346,504 A | 9/1994 | Oritz et al. | |
| 5,350,391 A | 9/1994 | Iacovelli | |
| 5,354,311 A | 10/1994 | Kambin et al. | |
| 5,356,416 A | 10/1994 | Chu et al. | |
| 5,358,508 A | 10/1994 | Cobb | |
| 5,364,408 A | 11/1994 | Gordon | |
| 5,381,943 A | 1/1995 | Allen et al. | |
| 5,383,260 A | 1/1995 | Deschenes et al. | |
| D356,154 S | 3/1995 | Ferragamo | |
| 5,395,030 A | 3/1995 | Kuramoto et al. | |
| 5,395,367 A | 3/1995 | Wilk | |
| 5,403,326 A | 4/1995 | Harrison et al. | |
| 5,433,721 A | 7/1995 | Hooven et al. | |
| 5,437,266 A | 8/1995 | McPherson et al. | |
| 5,441,507 A | 8/1995 | Wilk | |
| 5,447,512 A | 9/1995 | Wilson et al. | |
| 5,451,406 A | 9/1995 | Lawin | |
| 5,464,426 A | 11/1995 | Bonutti | |
| 5,465,894 A | 11/1995 | Clark et al. | |
| 5,470,337 A | 11/1995 | Moss | |
| 5,485,952 A | 1/1996 | Fontayne | |
| 5,486,189 A | 1/1996 | Mudry et al. | |
| 5,496,331 A | 3/1996 | Xu et al. | |
| 5,522,820 A | 6/1996 | Caspari et al. | |
| 5,528,334 A | 6/1996 | Lee | |
| 5,538,008 A | 7/1996 | Crowe et al. | |
| 5,549,618 A | 8/1996 | Fleenor et al. | |
| 5,558,665 A | 9/1996 | Kieturakis | |
| 5,571,090 A | 11/1996 | Sherts | |
| 5,571,116 A | 11/1996 | Bolanos et al. | |
| 5,573,496 A | 11/1996 | McPherson et al. | |
| 5,588,581 A | 12/1996 | Conlon et al. | |
| 5,597,378 A | 1/1997 | Jervis | |
| 5,624,453 A | 4/1997 | Ahmed | |
| 5,626,613 A | 5/1997 | Schmieding | |
| 5,645,552 A | 7/1997 | Sherts | |
| 5,662,683 A | 9/1997 | Kay | |
| 5,665,096 A | 9/1997 | Yoon | |
| 5,671,507 A | 9/1997 | Deschenes et al. | |
| 5,674,230 A | 10/1997 | Tovey et al. | |
| 5,676,674 A | 10/1997 | Bolanos et al. | |
| 5,697,940 A | 12/1997 | Chu et al. | |
| 5,699,808 A | 12/1997 | John | |
| 5,722,421 A | 3/1998 | Francese et al. | |
| 5,725,524 A | 3/1998 | Mulier et al. | |
| 5,728,109 A | 3/1998 | Schulze et al. | |
| 5,735,861 A | 4/1998 | Peifer et al. | |
| 5,741,280 A | 4/1998 | Fleenor | |
| 5,749,898 A | 5/1998 | Schulze et al. | |
| 5,787,897 A | 8/1998 | Kieturakis | |
| 5,788,138 A | 8/1998 | Deschenes et al. | |
| 5,792,153 A | 8/1998 | Swain et al. | |
| 5,792,478 A | 8/1998 | Lawin | |
| 5,794,948 A | 8/1998 | Schmitt et al. | |
| 5,797,927 A | 8/1998 | Yoon | |
| 5,810,855 A | 9/1998 | Rayburn et al. | |
| 5,810,882 A | 9/1998 | Bolduc et al. | |
| 5,814,054 A | 9/1998 | Kortenbach et al. | |
| 5,826,776 A | 10/1998 | Schulze et al. | |
| 5,845,645 A | 12/1998 | Bonutti | |
| 5,846,254 A | 12/1998 | Schulze et al. | |
| 5,853,409 A | 12/1998 | Swanson et al. | |
| 5,855,311 A | 1/1999 | Hamblin et al. | |
| 5,887,594 A | 3/1999 | LoCicero, III et al. | |

| | | | | | | |
|---|---|---|---|---|---|---|
| 5,893,592 | A | 4/1999 | Schulze et al. | 6,632,227 | B2 | 10/2003 | Adams |
| 5,897,562 | A | 4/1999 | Bolanos et al. | 6,645,201 | B1 | 11/2003 | Utley et al. |
| 5,899,915 | A | 5/1999 | Saadat | 6,652,545 | B2 | 11/2003 | Shipp et al. |
| 5,901,895 | A | 5/1999 | Heaton et al. | 6,660,301 | B1 | 12/2003 | Vogel et al. |
| 5,954,731 | A | 9/1999 | Yoon | 6,663,639 | B1 | 12/2003 | Laufer et al. |
| 5,958,444 | A | 9/1999 | Wallace | 6,666,848 | B2 | 12/2003 | Stone |
| 5,984,932 | A | 11/1999 | Yoon | 6,669,713 | B2 | 12/2003 | Adams |
| 5,993,466 | A | 11/1999 | Yoon | 6,673,058 | B2 | 1/2004 | Snow |
| 6,009,877 | A | 1/2000 | Edwards | 6,673,070 | B2 | 1/2004 | Edwards et al. |
| 6,051,003 | A | 4/2000 | Chu et al. | 6,692,507 | B2 | 2/2004 | Pugsley et al. |
| 6,059,798 | A | 5/2000 | Tolkoff | 6,695,764 | B2 | 2/2004 | Silverman et al. |
| 6,067,990 | A | 5/2000 | Kieturakis | 6,695,866 | B1 | 2/2004 | Kuehn et al. |
| 6,083,202 | A | 7/2000 | Smith | 6,699,243 | B2 | 3/2004 | West et al. |
| 6,086,600 | A | 7/2000 | Kortenbach | 6,712,074 | B2 | 3/2004 | Edwards et al. |
| 6,086,603 | A | 7/2000 | Termin et al. | 6,712,814 | B2 | 3/2004 | Edwards et al. |
| 6,098,629 | A | 8/2000 | Johnson | 6,716,226 | B2 | 4/2004 | Sixto, Jr. et al. |
| 6,102,887 | A | 8/2000 | Altman | 6,716,233 | B1 | 4/2004 | Whitman |
| 6,113,609 | A | 9/2000 | Adams | 6,725,866 | B2 | 4/2004 | Johnson et al. |
| 6,129,761 | A | 10/2000 | Hubbell | 6,743,240 | B2 | 6/2004 | Smith et al. |
| RE36,974 | E | 11/2000 | Bonutti | 6,773,440 | B2 | 8/2004 | Gannoe et al. |
| 6,152,935 | A | 11/2000 | Kammerer et al. | 6,773,441 | B1 | 8/2004 | Laufer et al. |
| 6,159,146 | A | 12/2000 | El Gazayerli | 6,790,214 | B2 | 9/2004 | Kraemer et al. |
| 6,179,840 | B1 | 1/2001 | Bowman | 6,790,237 | B2 | 9/2004 | Stinson |
| 6,221,084 | B1 | 4/2001 | Fleenor | 6,793,652 | B1 | 9/2004 | Whitman et al. |
| 6,238,335 | B1 | 5/2001 | Silverman et al. | 6,808,491 | B2 | 10/2004 | Kortenbach et al. |
| 6,254,642 | B1 | 7/2001 | Taylor | 6,821,285 | B2 | 11/2004 | Laufer et al. |
| 6,258,064 | B1 | 7/2001 | Smith et al. | 6,824,548 | B2 | 11/2004 | Smith et al. |
| 6,267,285 | B1 | 7/2001 | Raymond et al. | 6,835,200 | B2 | 12/2004 | Laufer et al. |
| 6,312,437 | B1 | 11/2001 | Kortenbach | 6,843,403 | B2 | 1/2005 | Whitman |
| 6,312,448 | B1 | 11/2001 | Bonutti | 6,843,794 | B2 | 1/2005 | Sixto, Jr. et al. |
| 6,315,184 | B1 | 11/2001 | Whitman | 6,846,307 | B2 | 1/2005 | Whitman et al. |
| 6,325,503 | B1 | 12/2001 | McCue, Jr. et al. | 6,846,308 | B2 | 1/2005 | Whitman et al. |
| 6,352,503 | B1 | 3/2002 | Matsui et al. | 6,846,309 | B2 | 1/2005 | Whitman et al. |
| 6,387,104 | B1 | 5/2002 | Pugsley, Jr. et al. | 6,849,071 | B2 | 2/2005 | Whitman et al. |
| 6,443,973 | B1 | 9/2002 | Whitman | 6,916,332 | B2 | 7/2005 | Adams |
| 6,454,778 | B2 | 9/2002 | Kortenbach | 6,926,722 | B2 | 8/2005 | Geitz |
| 6,461,366 | B1 | 10/2002 | Seguin | 6,945,979 | B2 | 9/2005 | Kortenbach et al. |
| 6,478,210 | B2 | 11/2002 | Adams et al. | 6,971,395 | B2 | 12/2005 | Edwards et al. |
| 6,494,888 | B1 | 12/2002 | Laufer et al. | 6,981,941 | B2 | 1/2006 | Whitman et al. |
| 6,506,196 | B1 | 1/2003 | Laufer | 6,986,737 | B2 | 1/2006 | Suzuki et al. |
| 6,540,789 | B1 | 4/2003 | Silverman et al. | 7,032,798 | B2 | 4/2006 | Whitman et al. |
| 6,544,291 | B2 | 4/2003 | Taylor | 7,033,370 | B2 | 4/2006 | Gordon et al. |
| 6,544,503 | B1 | 4/2003 | Vanderhoff et al. | 7,066,944 | B2 | 6/2006 | Laufer et al. |
| 6,547,776 | B1 | 4/2003 | Gaiser et al. | 7,077,856 | B2 | 7/2006 | Whitman |
| 6,548,501 | B2 | 4/2003 | Hakkinen | 7,087,073 | B2 | 8/2006 | Bonutti |
| 6,548,518 | B2 | 4/2003 | Rubin et al. | 7,153,314 | B2 | 12/2006 | Laufer et al. |
| 6,551,315 | B2 | 4/2003 | Kortenbach et al. | 2001/0049537 | A1 | 12/2001 | Kortenbach |
| 6,551,328 | B2 | 4/2003 | Kortenbach | 2001/0056282 | A1 | 12/2001 | Sonnenschein |
| 6,552,045 | B2 | 4/2003 | Rubin et al. | 2002/0010418 | A1 | 1/2002 | Lary et al. |
| 6,552,046 | B2 | 4/2003 | Druzgala et al. | 2002/0022851 | A1 | 2/2002 | Kalloo et al. |
| 6,552,047 | B2 | 4/2003 | Garvey et al. | 2002/0063143 | A1 | 5/2002 | Adams et al. |
| 6,558,400 | B2 | 5/2003 | Deem et al. | 2002/0068945 | A1 | 6/2002 | Sixto et al. |
| 6,558,429 | B2 | 5/2003 | Taylor | 2002/0068946 | A1 | 6/2002 | Kortenbach et al. |
| 6,559,165 | B1 | 5/2003 | Rubin et al. | 2002/0078967 | A1 | 6/2002 | Sixto et al. |
| 6,562,034 | B2 | 5/2003 | Edwards et al. | 2002/0082621 | A1 | 6/2002 | Schurr |
| 6,562,795 | B2 | 5/2003 | Ashley et al. | 2002/0138086 | A1 | 9/2002 | Sixto et al. |
| 6,569,085 | B2 | 5/2003 | Kortenbach et al. | 2002/0173786 | A1 | 11/2002 | Kortenbach et al. |
| 6,569,105 | B1 | 5/2003 | Kortenbach et al. | 2002/0193816 | A1 | 12/2002 | Laufer et al. |
| 6,572,626 | B1 | 6/2003 | Knodel et al. | 2002/0198537 | A1 | 12/2002 | Smith et al. |
| 6,575,971 | B2 | 6/2003 | Hauck et al. | 2002/0198538 | A1 | 12/2002 | Kortenbach et al. |
| 6,579,301 | B1 | 6/2003 | Bales et al. | 2002/0198539 | A1 | 12/2002 | Sixto et al. |
| 6,589,238 | B2 | 7/2003 | Edwards et al. | 2002/0198540 | A1 | 12/2002 | Smith et al. |
| 6,591,137 | B1 | 7/2003 | Fischell et al. | 2002/0198541 | A1 | 12/2002 | Smith et al. |
| 6,591,838 | B2 | 7/2003 | Durgin | 2002/0198549 | A1 | 12/2002 | Sixto et al. |
| 6,592,596 | B1 | 7/2003 | Geitz | 2003/0019905 | A1 | 1/2003 | Adams et al. |
| 6,592,609 | B1 | 7/2003 | Bonutti | 2003/0036679 | A1 | 2/2003 | Kortenbach et al. |
| 6,595,909 | B2 | 7/2003 | Silverman et al. | 2003/0065340 | A1 | 4/2003 | Geitz |
| 6,595,910 | B2 | 7/2003 | Silverman et al. | 2003/0065359 | A1 | 4/2003 | Weller et al. |
| 6,604,004 | B1 | 8/2003 | Zelickson et al. | 2003/0068326 | A1 | 4/2003 | Gevas et al. |
| 6,604,528 | B1 | 8/2003 | Duncan | 2003/0069280 | A1 | 4/2003 | Koch et al. |
| 6,605,078 | B2 | 8/2003 | Adams | 2003/0069646 | A1 | 4/2003 | Stinson |
| 6,609,140 | B1 | 8/2003 | Greene | 2003/0083241 | A1 | 5/2003 | Young |
| 6,613,047 | B2 | 9/2003 | Edwards | 2003/0086968 | A1 | 5/2003 | Gray |

| | | | | | | |
|---|---|---|---|---|---|---|
| 2003/0092699 A1 | 5/2003 | Uchida et al. | | JP | 05103241 A | 4/1993 |
| 2003/0130560 A1 | 7/2003 | Suzuki et al. | | JP | 05323412 A | 12/1993 |
| 2003/0130561 A1 | 7/2003 | Suzuki et al. | | JP | 08006102 A | 1/1996 |
| 2003/0135206 A1 | 7/2003 | Edwards et al. | | JP | 2000254143 A | 9/2000 |
| 2003/0161887 A1 | 8/2003 | Klein | | JP | 2003051982 A | 2/2003 |
| 2003/0163029 A1 | 8/2003 | Sonnenschein et al. | | JP | 2006311060 A | 11/2006 |
| 2003/0167062 A1 | 9/2003 | Gambale et al. | | WO | 8911827 | 12/1989 |
| 2003/0171645 A1 | 9/2003 | Silverman et al. | | WO | WO-8911827 | 12/1989 |
| 2003/0181929 A1 | 9/2003 | Geitz | | WO | 9627345 A2 | 9/1996 |
| 2003/0188755 A1 | 10/2003 | Milbocker | | WO | 9803151 | 1/1998 |
| 2003/0191478 A1 | 10/2003 | Kortenbach et al. | | WO | WO-9803151 | 1/1998 |
| 2003/0192558 A1 | 10/2003 | Durgin | | WO | WO 99/00059 | 1/1999 |
| 2003/0192559 A1 | 10/2003 | Durgin | | WO | WO-990059 | 1/1999 |
| 2003/0195387 A1 | 10/2003 | Kortenbach et al. | | WO | 9922649 | 5/1999 |
| 2003/0195509 A1 | 10/2003 | Edwards et al. | | WO | WO 99/22649 | 5/1999 |
| 2003/0196670 A1 | 10/2003 | Durgin | | WO | WO 9922649 | 5/1999 |
| 2003/0199731 A1 | 10/2003 | Silverman et al. | | WO | WO 99/60931 | 12/1999 |
| 2003/0208209 A1 | 11/2003 | Gambale et al. | | WO | WO 9960931 | 12/1999 |
| 2003/0208211 A1 | 11/2003 | Kortenbach | | WO | WO 0035529 | 6/2000 |
| 2003/0216754 A1 | 11/2003 | Kraemer et al. | | WO | 00/78229 | 12/2000 |
| 2003/0220657 A1 | 11/2003 | Adams | | WO | WO 00/35529 | 12/2000 |
| 2003/0220660 A1 | 11/2003 | Kortenbach et al. | | WO | WO 00/78227 | 12/2000 |
| 2003/0236535 A1 | 12/2003 | Onuki et al. | | WO | WO 0078227 | 12/2000 |
| 2003/0236536 A1 | 12/2003 | Grigoryants et al. | | WO | WO 0078229 | 12/2000 |
| 2004/0006336 A1 | 1/2004 | Swanson | | WO | 0185034 | 11/2001 |
| 2004/0006351 A1 | 1/2004 | Gannoe et al. | | WO | WO 01085034 | 11/2001 |
| 2004/0010245 A1 | 1/2004 | Cerier et al. | | WO | WO 02/24080 | 3/2002 |
| 2004/0037887 A1 | 2/2004 | Bourne et al. | | WO | WO-0224080 | 3/2002 |
| 2004/0044364 A1 | 3/2004 | DeVries et al. | | WO | 0228289 | 4/2002 |
| 2004/0059349 A1 | 3/2004 | Sixto et al. | | WO | WO-0228289 | 4/2002 |
| 2004/0059350 A1 | 3/2004 | Gordon et al. | | WO | 0240081 | 5/2002 |
| 2004/0059354 A1 | 3/2004 | Smith et al. | | WO | WO-0240081 | 5/2002 |
| 2004/0059358 A1 | 3/2004 | Kortenbach et al. | | WO | 0245603 | 6/2002 |
| 2004/0082859 A1 | 4/2004 | Schaer | | WO | WO-0245603 | 6/2002 |
| 2004/0082950 A1 | 4/2004 | Edwards et al. | | WO | WO 02/076541 | 10/2002 |
| 2004/0082963 A1 | 4/2004 | Gannoe et al. | | WO | WO-0276541 | 10/2002 |
| 2004/0116948 A1 | 6/2004 | Sixto et al. | | WO | WO 02076541 | 10/2002 |
| 2004/0133238 A1 | 7/2004 | Cerier | | WO | 02094341 | 11/2002 |
| 2004/0147943 A1 | 7/2004 | Kobayashi | | WO | WO-0294341 | 11/2002 |
| 2004/0153107 A1 | 8/2004 | Kayan et al. | | WO | WO-02094341 | 11/2002 |
| 2004/0162568 A1 | 8/2004 | Saadat et al. | | WO | 03000115 | 1/2003 |
| 2004/0176783 A1 | 9/2004 | Edoga et al. | | WO | 03004087 | 1/2003 |
| 2004/0193184 A1 | 9/2004 | Laufer et al. | | WO | 03007796 | 1/2003 |
| 2004/0193193 A1 | 9/2004 | Laufer et al. | | WO | WO-03000115 | 1/2003 |
| 2004/0193194 A1 | 9/2004 | Laufer et al. | | WO | WO-03004087 | 1/2003 |
| 2004/0194790 A1 | 10/2004 | Laufer et al. | | WO | WO-03007796 | 1/2003 |
| 2005/0033320 A1 | 2/2005 | McGuckin et al. | | WO | 03015604 | 2/2003 |
| 2005/0033328 A1 | 2/2005 | Laufer et al. | | WO | WO-03015604 | 2/2003 |
| 2005/0216036 A1 | 9/2005 | Nakao | | WO | 03030782 | 4/2003 |
| 2006/0025789 A1 | 2/2006 | Laufer et al. | | WO | WO-03030782 | 4/2003 |
| 2009/0198254 A1 | 8/2009 | Laufer et al. | | WO | 03037256 | 5/2003 |
| | | | | WO | WO-03035649 | 5/2003 |
| FOREIGN PATENT DOCUMENTS | | | | WO | WO-03037256 | 5/2003 |
| | | | | WO | 03053253 | 7/2003 |
| EP | 0480428 | 4/1992 | | WO | WO-03053253 | 7/2003 |
| EP | 0 576 265 | 12/1993 | | WO | 03072196 | 9/2003 |
| EP | 0576265 | 12/1993 | | WO | WO-03072196 | 9/2003 |
| EP | 0593920 | 4/1994 | | WO | 03082359 | 10/2003 |
| EP | 593920 A1 | 4/1994 | | WO | WO-03030804 | 10/2003 |
| EP | 0 646 356 A2 | 4/1995 | | WO | 03090633 | 11/2003 |
| EP | 0646356 | 4/1995 | | WO | 03092498 | 11/2003 |
| EP | 0 668 058 | 8/1995 | | WO | 03092509 | 11/2003 |
| EP | 9668058 | 8/1995 | | WO | 03094800 | 11/2003 |
| EP | 0743044 | 11/1996 | | WO | 03096885 | 11/2003 |
| EP | 0975263 | 2/2000 | | WO | 03096885 A2 | 11/2003 |
| EP | 0 743 044 | 4/2003 | | WO | 03098885 | 11/2003 |
| EP | 0 975 263 | 10/2003 | | WO | WO-03090633 | 11/2003 |
| FR | 2 768 324 | 3/1999 | | WO | WO-03092498 | 11/2003 |
| FR | 2768324 | 3/1999 | | WO | WO-03092509 | 11/2003 |
| GB | 2075829 | 11/1981 | | WO | WO-03094800 | 11/2003 |
| JP | 61-122852 | 6/1986 | | WO | WO-03098885 | 11/2003 |
| JP | 61122852 | 6/1986 | | WO | 03099137 | 12/2003 |
| JP | 1151461 | 6/1989 | | WO | 03099139 | 12/2003 |

| | | |
|---|---|---|
| WO | 03099140 | 12/2003 |
| WO | 03099376 | 12/2003 |
| WO | 03105917 | 12/2003 |
| WO | 2004000129 | 12/2003 |
| WO | WO-03099137 | 12/2003 |
| WO | WO-03099139 | 12/2003 |
| WO | WO-03099140 | 12/2003 |
| WO | WO-03099376 | 12/2003 |
| WO | WO-03105917 | 12/2003 |
| WO | WO-2004000129 | 12/2003 |
| WO | 2004004542 | 1/2004 |
| WO | 2004004544 | 1/2004 |
| WO | 2004006990 | 1/2004 |
| WO | WO-04004542 | 1/2004 |
| WO | WO-04004544 | 1/2004 |
| WO | 2004019787 | 3/2004 |
| WO | 2004019788 | 3/2004 |
| WO | 2004021872 | 3/2004 |
| WO | 2004021873 | 3/2004 |
| WO | 2004021894 | 3/2004 |
| WO | WO-04006990 | 3/2004 |
| WO | WO-04019787 | 3/2004 |
| WO | WO-2004019788 | 3/2004 |
| WO | WO-2004021872 | 3/2004 |
| WO | WO-2004021873 | 3/2004 |
| WO | WO-2004021894 | 3/2004 |
| WO | 2004026348 | 4/2004 |
| WO | 2004026349 | 4/2004 |
| WO | 2004026350 | 4/2004 |
| WO | WO-2004026348 | 4/2004 |
| WO | WO-2004026349 | 4/2004 |
| WO | WO-2004026350 | 4/2004 |
| WO | 2005086885 | 9/2005 |
| WO | WO-2005086885 | 9/2005 |

OTHER PUBLICATIONS

Carvalho PJPC et al., Fibrosis of gastric cardia after endoscopic sclerosis. Mechanism for control of experimental reflux? *Am Surg* Mar. 1990;56(3):163-6.
Contractor QQ et al., Endoscopic esphagitis and gastroesophageal flap valve. *J Clin Gastroenterol* Apr. 1999; 28(3):233-7.
Hill LD and Kozarek RA, The gastroesophageal flap valve. *J Clin Gastroenterol* Apr. 1999:28(3):194-7.
Hill LD et al., Antireflux surgery. A surgeon's look. *Gastroenterol Clin North Am* Sep. 1990:19(3):745-75.
Hill LD et al., The gastroesophageal flap valve: in vitro and in vivo observations. *Gastrointest Endosc* Nov. 1996;44(5):541-7.
Hill LD, Intraoperative measurement of lower esophageal sphincter pressure. *J Thorac Cardiovasc Surg* Mar. 1978;75(3):378-82.
Hill LD, Mythis of the esophagus. *J Thorac Cardivasc Surg* Jul. 1989;98(1):1-10.
Ismail T. et al., Yield pressure, anatomy of the cardia and gastro-oesophageal reflux. *Br J Surg* Jul. 1995;82(7):943-7.
Kadirkamanathan SS et al., An ambulant porcine model of acid reflux used to evaluate endoscopic gastroplasty. *Gut* Jun. 1999;44(6):782-9.
Kadirkamanathan SS et al., Antireflux operations at flexible endoscopy using endoluminal stitching techniques: an experimental study. *Gastrointest* Endosc Aug. 1996;44(2):133-43.
Mason RJ et al., A new intraluminal antigastroesophageal reflux procedure in baboons. *Gastrointest Endosc* Mar. 1997; 45(3):283-90.
McGouran RC et al., Does measurement of yield pressure at the cardia during endoscopy provide information on the function of the lower oesophageal sphincter mechanism? *Gut* Mar. 1988; 29(3):275-8.
McGouran RC et al., Is yield pressure at the cardia increased by effective fundoplication? *Gut* Oct. 1989;30(10):1309-12.
O'Connor KW et al., An experimental endoscopic technique for reversing gastroesophageal reflux in dogs by injecting inert material in the distal esophagus. *Gastrointest Endosc* Oct. 1984;30(5):275-80.
Rupp TH and Lehman GA, Endoscopic antireflux techniques. Endoluminal and lapaoscopic. *Gastrointest Endosc Clin N Am* Apr. 1994;4(2):353-68.

Shafik A., Intraesophageal Polytef injection for the treatment of reflux esophagitis. *Surg Endosc* Mar. 1996;10(3):329-31.
Slim K et al., Intraoperative esophageal manometry and fundoplications: prospective study. World J Surg Jan. 1996;20(1):55-9.
Thor KBA et al., Reappraisal of the flap valve mechanism in the gastroesophageal junction. A study of a new valvuloplasty procedure in cadavers. *Acta Chir Scand* Jan. 1987;153(1):25-8.
Boerema, M.D. , "Hiatus hernia: Repair by right-sided, subhepatic, anterior gastropexy," *Surgery*, 65:884-893 (1969).
Cecconello, "Esophagogastric Anastomosis with Valvuloplasty: An Experimental Study," *International Surgery*, 67:121-124 (1982).
Collis, M.D., "Surgical Control of Reflux in Hiatus Hernia," *The American Journal of Surgery*, 115:465-471 (1968).
Collis, M.D., "An Operation for Hiatus Hernia with Short Esophagus," *The Journal of Thoracic Surgery*, 34:768-778 (1957).
Cuschieri, et al., "Multicenter prospective evaluation of laparoscopic antireflux surgery," *Surgical Endoscopy*, 7:505-510 (1993).
DeMeester, M.D. et al., "Nissen Fundoplication for Gastroesophageal Reflux Disease," *Annals of Surgery*, 204:9-20 (1986).
Donahue, M.D., et al., "Endoscopic Control of Gastro-Esophageal Reflux: Status Report," *World Journal of Surgery*, 16:343-346 (1992).
Donahue, M.D., et al., "Endoscopic sclerosis of the gastic cardia for prevention of experimental gastroesophageal reflux," *Gastrointestinal Endoscopy*, 36:253-256 (1990).
Falk, et al., "Laparoscopic Fundoplication: A preliminary report of the technique and postoperative care," *Aust. N.Z. J. Surgery*, 62:969-972 (1992).
Hill, et al., "*Surgery for Peptic Esophageal Stricture*," 139-147.
Hill, M.D., "An Effective Operation for Hiatal Hernia: An Eight Year Appraisal," *Annals of Surgery*, 166:681-692 (1967).
Hill, et al., "The Esophagus, Medical and Surgicial Management," *WB Saunders Co.*, 135-8 (1988).
Hinder, et al. "The Surgical Option for Gastroesophageal Reflux Disease," Symposium on Gastroesophageal Reflux Disease, *AM J Med*, 103:144S-148S (1997).
Ismail, et al., "Yield Pressure: A New Concept in the Evaluation of Gerd?,"*AJG*, 91:616-617 (1996).
Jamieson, et al. ,"The development of surgery for gastro-oesophageal reflux disease," *Surgery of the Oesophagus*, 233-245 (1988).
Jamieson, et al., "Laparoscopic Nissen Fundoplication," *Annals of Surgery*, 220:137-145 (1994).
Janssen, et al., "Prospective randomized comparison of teres cardiopexy and Nissen fundoplication in the surgical therapy of gastro-oesophageal reflux disease," *Br. J.Surg.*80:875-878 (1993).
Jennings, et al., "A Novel Endoscopic Transgastric Fundoplication Procedure for Gastroesophageal Reflux: An Initial Animal Evaluation," *Journal of Laparoendoscopic Surgery*, 2:207-213 (1992).
Kahrilas, "Gastroesophageal Reflux Disease,"*JAMA*, 276:983-988 (1996).
Kraemer, M.D., et al., "Laparoscopic Hill repair," *Gastrointestinal Endoscopy*, 40:155-159 (1994).
Little, M.D., "Mechanisms of Action of Antireflux Surgery: Theory and Fact," *World Journal of Surgery*, 16:320-325 (1992).
Mason, et al., "Nissen Fundoplication Prevents Shortening of the Sphincter During Gastric Distention," *Arch Surg.*, 132:719-726 (1997).
McGouran, M.D., et al., "A laser-induced scar at the cardia increases the yield pressure of the lower esophageal sphincter," *Gastronintestinal Endoscopy*, 36:439-443 (1990).
McKernan, "Laparoscopic repair of gastroesophageal reflux disease," *Surgical Endoscopy*, 8:851-856 (1994).
Nathanson, et al., "Laparoscopic Ligamentum teres (round ligament) cardiopexy," *Br. J. Surg.*, 78:947-951 (1991).
Nissen, "Eine einfache Operation zur Beeinflussung der Refluxoesophagitis," *Journal Suisee De Medecine*, 590-592 (1956).
O'Connor, et al., "Endoscopic placement of collagen at the lower esophageal sphincter to inhibit gastroesophageal reflux: a pilot study of 10 medically intractable patients," *Gastrointestinal Endoscopy*, 34:106-112 (1988).

Pedinielli, "Traitement Chirurgical de la Herinie Hiatale Par La Technique du Collet", *Ann. Chir.*, 18:1461-1474 (1964). (English Abstract).
Polk, et al. "Hiatol Hernia and Esophagitis: A survey of indications for operation and technic and results of fundoplication," *Ann. Surg.*, 173:775-781 (1971).
Rampal, et al., "Technique Chirurgicale, Traitement des hernies hiatales et du reflux aesophagien par la cardio-pexie avec le ligament round de foie," *La Presse Medicale*, 75:617-619 (1967).
Rich, "Simple GERD Treatment Offers New Alternative,"(www.medicalpost.com website), Mar. 1999.
Singh, et al., "Evaluation of the Endoscopic Suturing System in the Treatment of GERD," *DDW*, May 16-19, 1999.
Skinner, et al., "Surgical management of esophageal reflux and hiatus hernia," *Journal of Thoracic and Cardiovascular Surgery*, 53:33-54 (1967).
Starling, et al. Assessment of the Angelchik Prosthesis for Treatment of Symptomatic Esophageal Reflux, *World J. Surg.* 11, 350-355 (1987).
Tocornal, M.D., et al., "A mucosol flap valve mechanism to prevent gastroesophageal reflux and esophagitis," *Surgery*, 64:519-523 (1968).
Wang, et al., "A new anti-flux procedure: cardiac oblique invagination," *Chung Hua Wai Ko Tsa Chih*, Feb; 33 (2) 73-5 (1995). (English Abstract).
Watson, et al., "Comparison of anterior, posterior and total fundoplication using a viscera model," *Diseases of the Esophagus*, 10: 110-114 (1997).
Westbrook, et al., "Posterior Surgical Approaches to the Rectum," *Annals of Surgery*, 195:677-691 (1982).
Bancewicz et al., "Yield pressure, anatomy of the cardia and gastro-oesophageal reflux", British Journal of Surgery, 1995, vol. 82, No. 7p. 943-947.
Hinder et al., "The surgical option for gastroesophageal reflux disease", Symposium on gastroesophageal reflux disease, Am J. Med., 103: 1445-1485, 1997.
The American Journal of Gastroenterology, vol. 91, No. 3, 1996, pp. 616-617.
Singh et al., "Evaluation of the Endoscopic Suturing System in the Treatment of the GERD", Conference Abstract for Plenary Session for Digestive Disease Week, p. 314 & A-802, May 16-19, 1999.
European Search Report mailed Sep. 2, 2004, in EP Application No. 04 07 6389.
European Search Report dated Sep. 2, 2004 in EP 04076389.
International Search Report dated Oct. 22, 2003.
Boerema MD 'Hiatus Hernia: Repair by right-sided, subhepatic, anterior gastropexy ' Surgery, 65:884-893 (1969).
Carvalho PJPC et at 'Fibrosis of gastric cardia after endoscopic sclerosis. Mechanism for control of experimental reflux? Am Surg Mar. 1990; 56(3) :163-6.
DeMeester, MD et al 'Nissen Fundoplication for Gastroesophageal Reflux Disease' Annals of Surgery 204:9-20 (1986).
Hill et at 'Surgery for Peptic Esophageal Stricture' 139-147.
Hill et at 'The Esophagus, Medical and Surgical Management' WB Saunders Co. 135-8 (1988).
Hill LD 'Myths of the esophagus' J Thorac Cardiovasc Surg July (1989)98(1):1-10.
Hill MD 'An Effective Operation for Hiatal Hernia: An Eight Year Appraisal' Annals of Surgery (1967) 166:681-692.
Kraemer, MD et al 'Laparascopic Hill repair' Gastrointestinal Endoscopy, vol. 40 No. 2 155-159 (1994).
Mason et al 'Nissen Fundoplication Prevents Shortening of the Sphincter During Gastric Distention' Arch Surg., 132:719-726 (1997).
Skinner et al 'Surgical management of esophageal reflux and hiatus hernia' Journal of Thoracic and Cardiovascular Surgery (1967) vol. 53, No. 1 pp. 33-54.
Starling et al 'Assessment of the Angelchik Prosthesis for Treatment of Symptonatic Esophageal Reflux' World J. Surg. 11, 350-355 (1987).

Kahrilas, "Gastroesophageal Reflux Disease,"JAMA, 276:983-988 (1996).
Kadirkamanathan SS et al., An ambulant procine model of acid reflux used to evaluate endoscopic gastroplasty. Gut Jun. 1999;44(6):782-8.
Mason RJ et al., A new intraluminal antigastroesphageal reflux procedure in baboons. Gastroinest Endosc Mar. 1997;45(3):283-90.
Hill LD et al., The gastroesophageal flap valve: in vitro and vivo observations. Gastrointest Endosc Nov. 1996;44(5):541-7.
Cuschieri, et al., "Multicenter prospective evaluation of laparoscopic antireflux surgery," Surgical Endoscopy, 7:505-510 (1993).
Digestive Disease Week, Orange County Convention Center, p. A-802; 314.
Donahue PE et al., Endoscopic sclerosis of the gastric cardia for prevention of experimental gastroesophageal reflux, *Gastrointest. Endosc.* May-Jun. 1990 36(3):253-6.
Hill LD and Kozarek RA, The gastroesophageal flap valve, *J. Clin. Gastroenterol* Apr. 1999 28(3): 194-7.
Hill LD et al., Antireflux surgery. A surgeon's look, *Gastroenterol Clin. North Am.*, Sep. 1990 19(3):745-75.
Hill LD, Myths of the esophagus, *J. Thorac Cardiovasc. Surg.* Jul. 1989 9S(1):1-10.
Hill, et al., "The Esophagus. Medical and Surgical Management," *WB Saunders Co.*, 135-8 (1988).
Jamieson, et al., "The development of surgery for gastro-oesophageal reflux disease." *Surgery of the Oesophagus*, 233-245 (1988).
McGouran RC and Galloway JM, A laser-induced scar at the cardia increases the yield pressure of the lower esophageal sphicter, *Gastrointest. Endosc.* 1990 Sep.-Oct. 36(5):43943.
O'Connor KW and Lehman GA, Endoscopic placement of collagen at the lower esophageal sphicter to inhibit gastroesophageal reflux: a pilot study of 10 medically intractable patients. *Gastrointest. Endosc.* Mar.-Apr. 1988 34(2):106-12.
Pedinielli, "Traitement Chirurgical de Ia Herinie Hiatale Par La Technique du Collet," *Ann. Chir.*, 18:1461-1474 (1964). (English Abstract).
Polk, et al., "Hiatol Hernia and Esophagitis: A survey of indications for operation and technic and results of fundolication," *Ann. Sur.*, 173:775-781 (1971).
Rich, "Simple GERD Treatment Offers New Alternative" (www.medicalpost.com website), Mar. 1999.
Sheik A., Intraesophageal Polytef injection for the treatment of reflux esophagitis. *Surg. Endosc.* Mar. 1996 10(3):329-31.
The Americal journal of gastroenterology, vol. 91, No. 3, 1996, pg. 616-617.
Tocornal, M.D., et al., A mucosol flap valve mechanism to prevent gastroesophageal reflux and esophagitis, *Surgery*, 64:519-523 (1968).
Eurpoean Search Report mailed Jul. 10, 2007 in EP Application No. 07075291.
Feb. 20, 2009, Office Action for U.S. Appl. No. 10/819,957.
Bancewicz et al 'Yield Pressure, Anatomy of the cervix and Gastrooesphageal Reflux' The American Journal of Gastroenterology, vol. 91, No. 3, (1996) pp. 616-617.
Digestive Disease Week, Orange County Convention Center, p. A-802; 314*.
Kadirkamanathan SS et al An ambulant procine model of acid reflux used to evaluate endoscopic gastroplasty. Gut Jun (1999); 44(6):782-8.
Polk et al 'Hiatol Hernia and Esophagitis' A survey of indications for operation and technic and results of fundoplication' presented at the Southern Surgical Association meeting held in Boca Raton, FL Dec. 7-9, (1970) pp. 775-781.
Rampal et al 'Technique Chirurgicale' LaPresse Medicale, vol. 75, No. 12 pp. 2-4.
Westbrook et al 'Posterior Surgical Approaches to the Rectum' Annals of Surgery (1982) 195:677-691.
Japanese Office Action for Application No. 2005-122394 dated May 12, 2009.

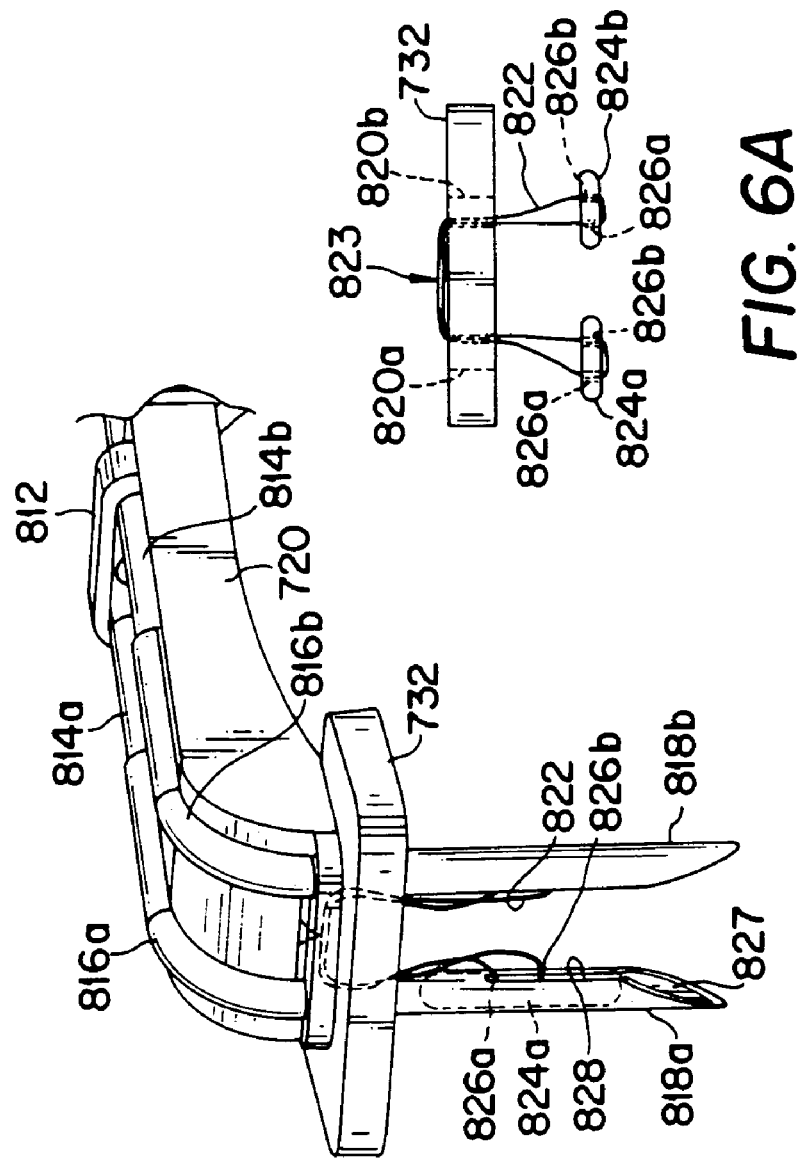
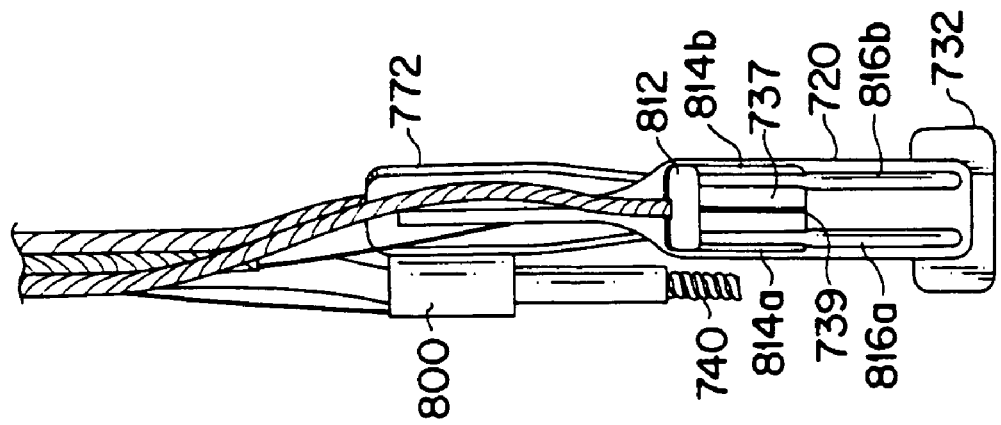

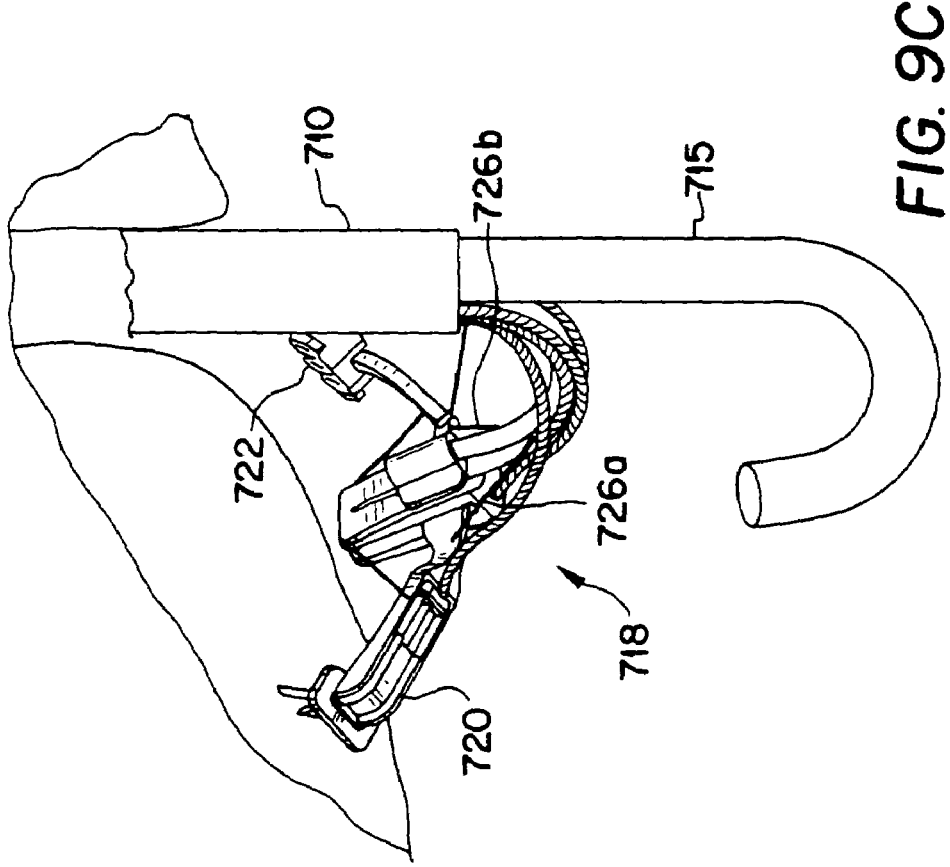
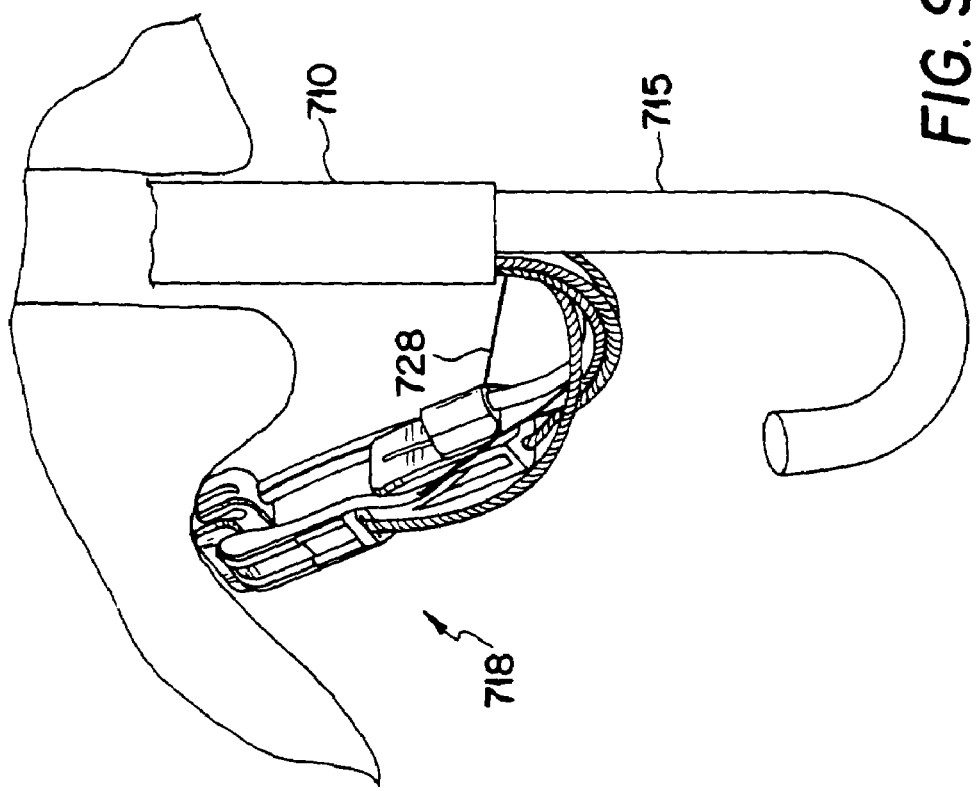

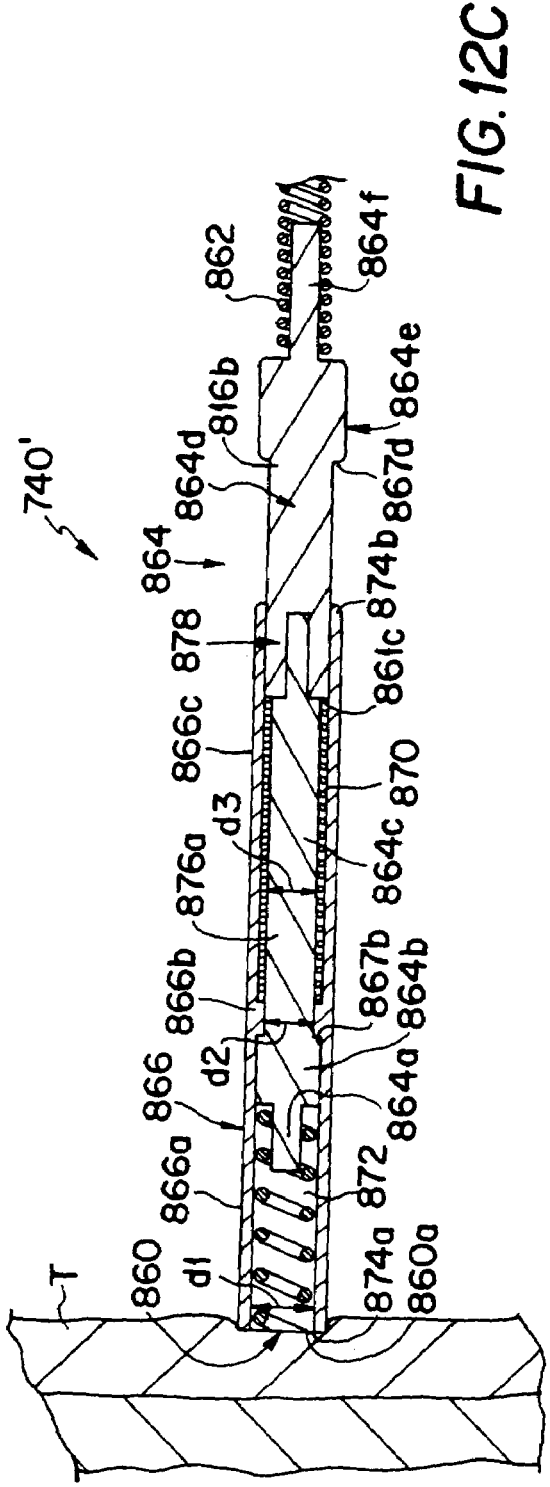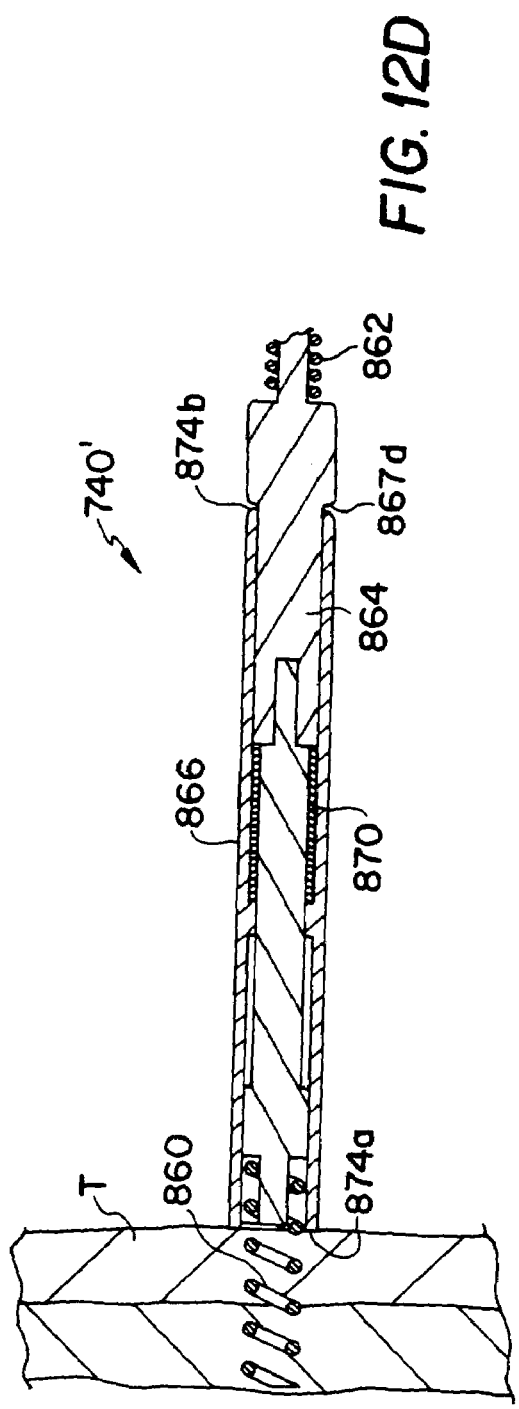

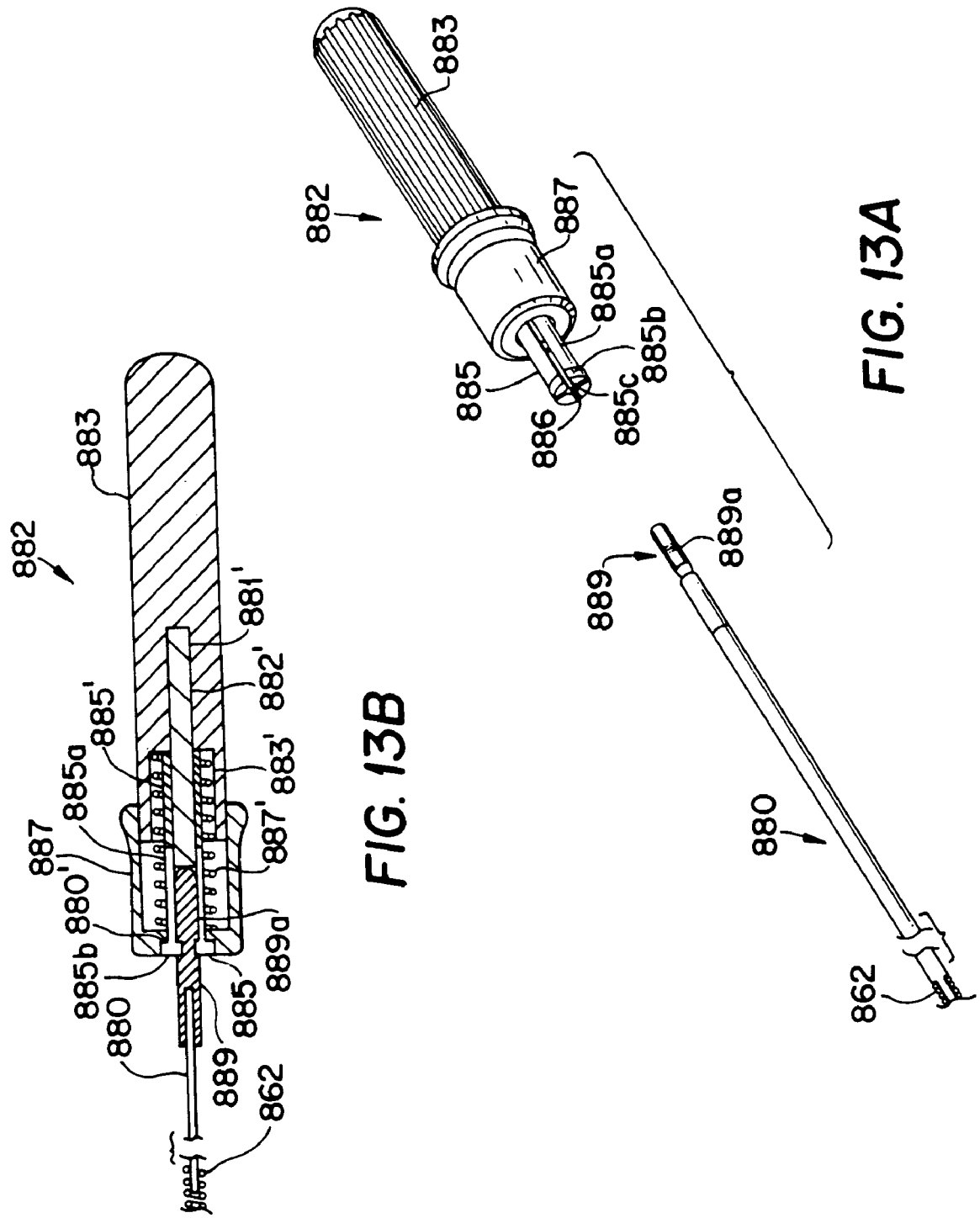

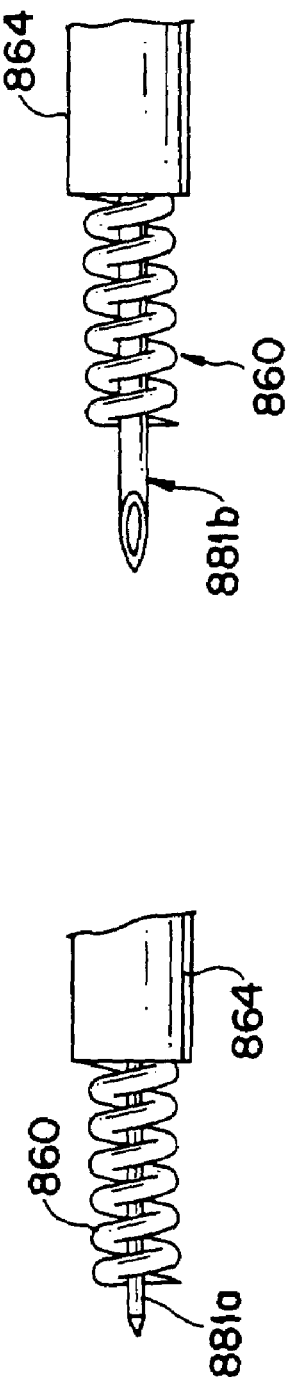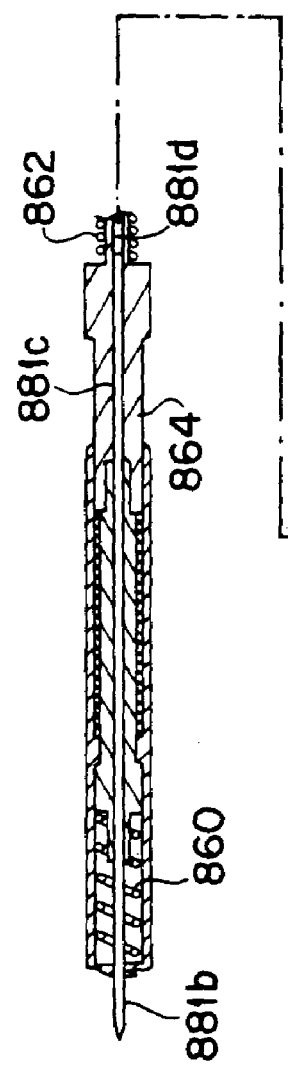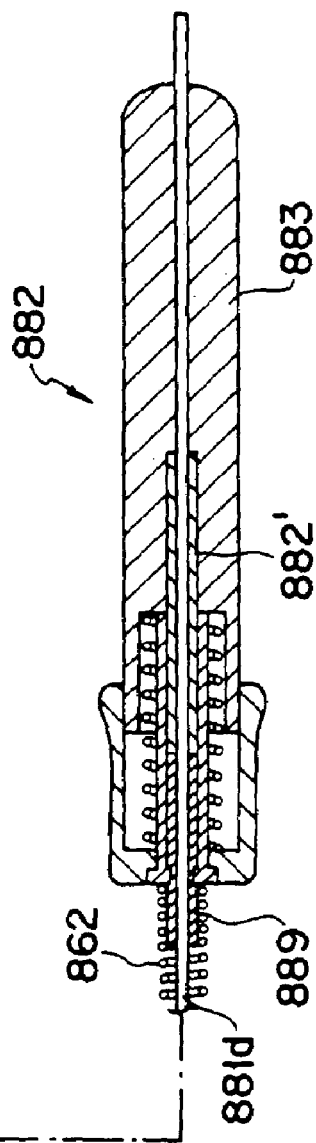

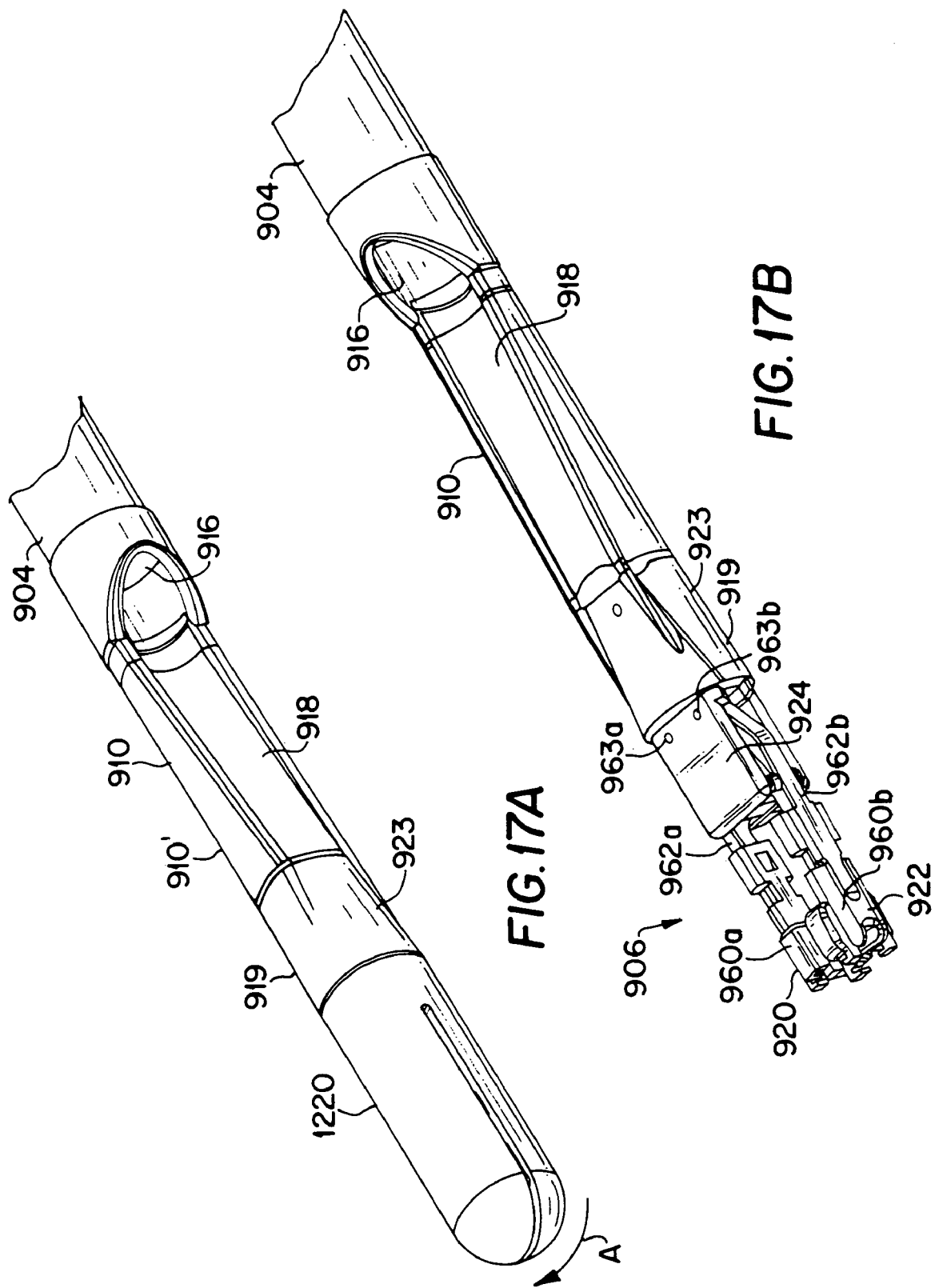

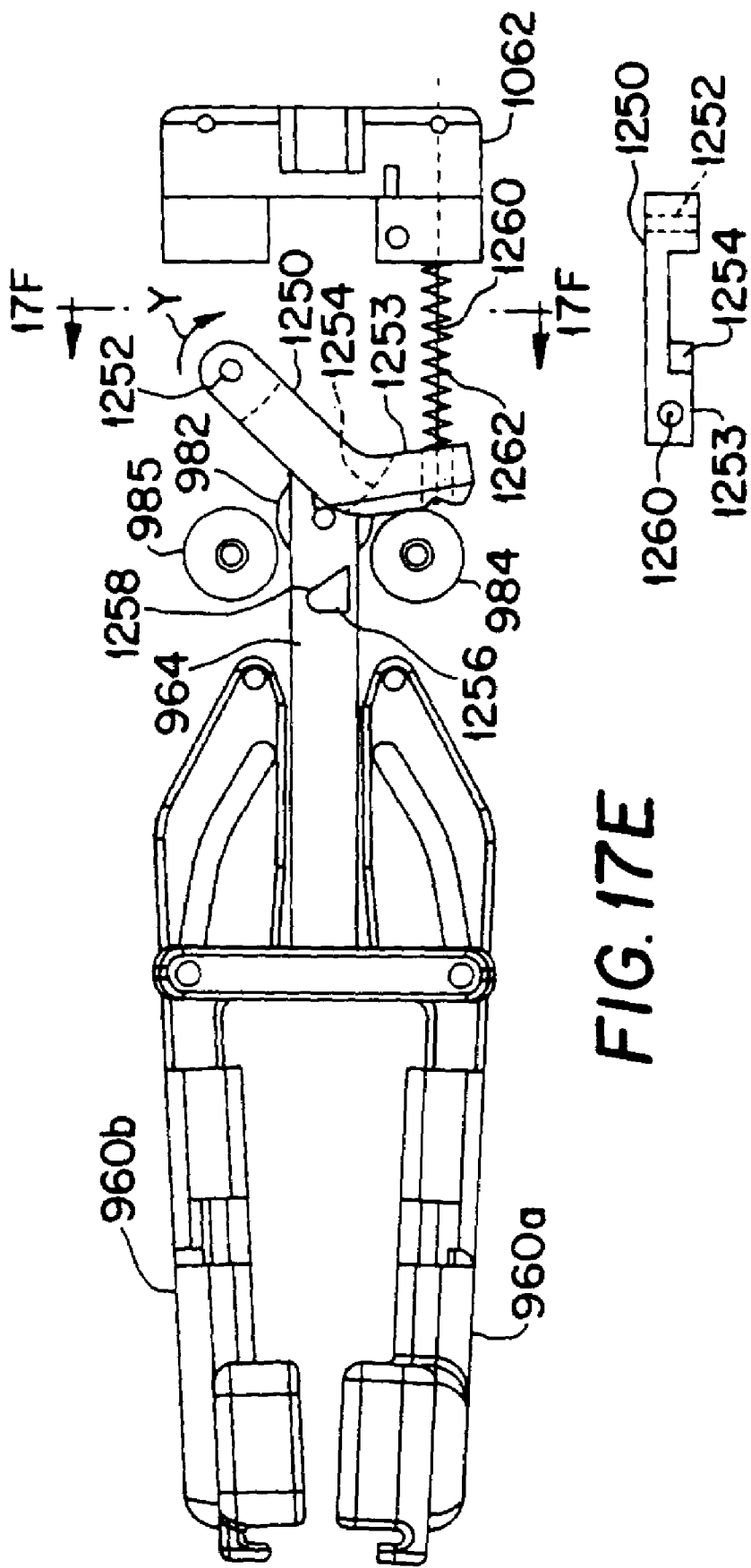

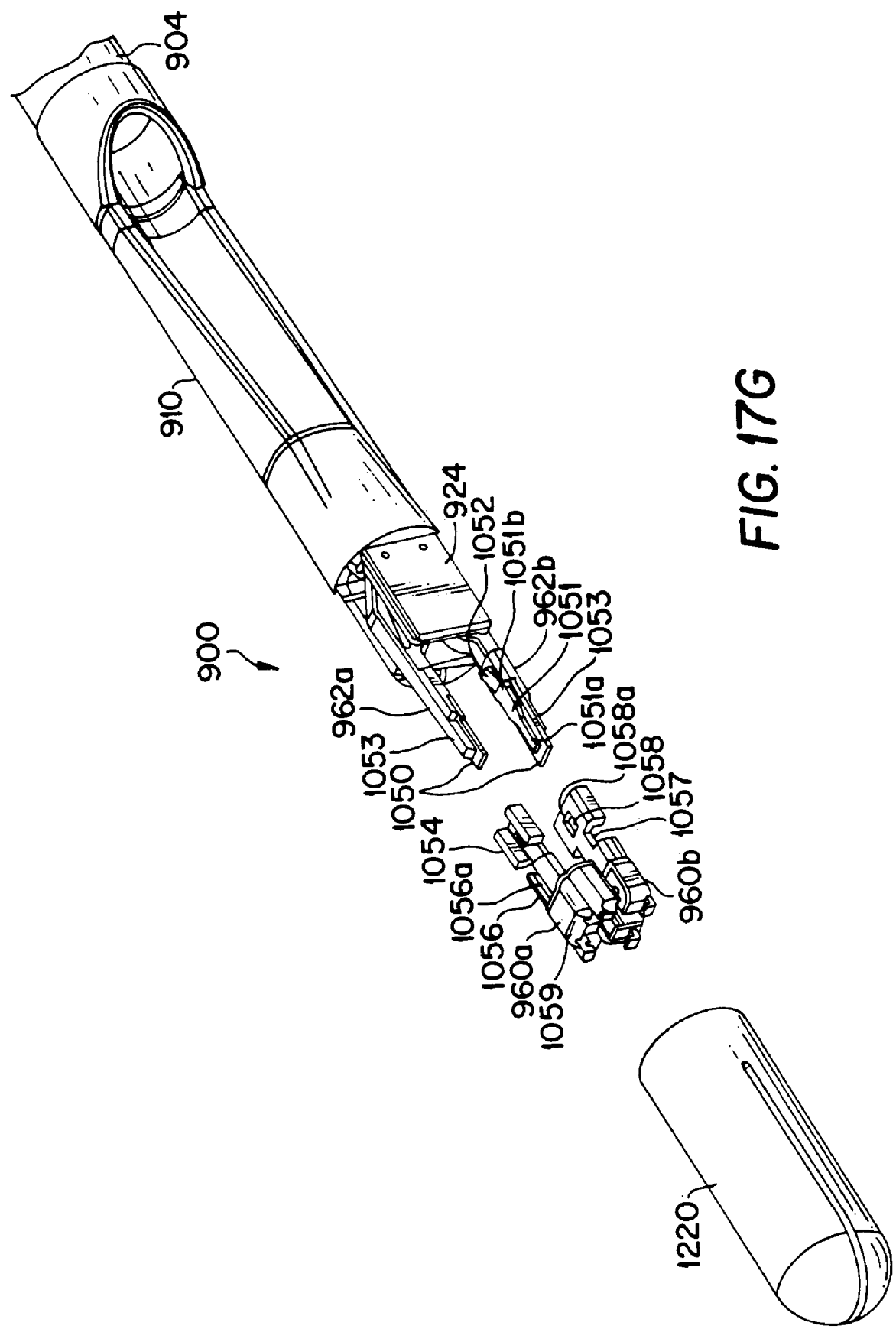

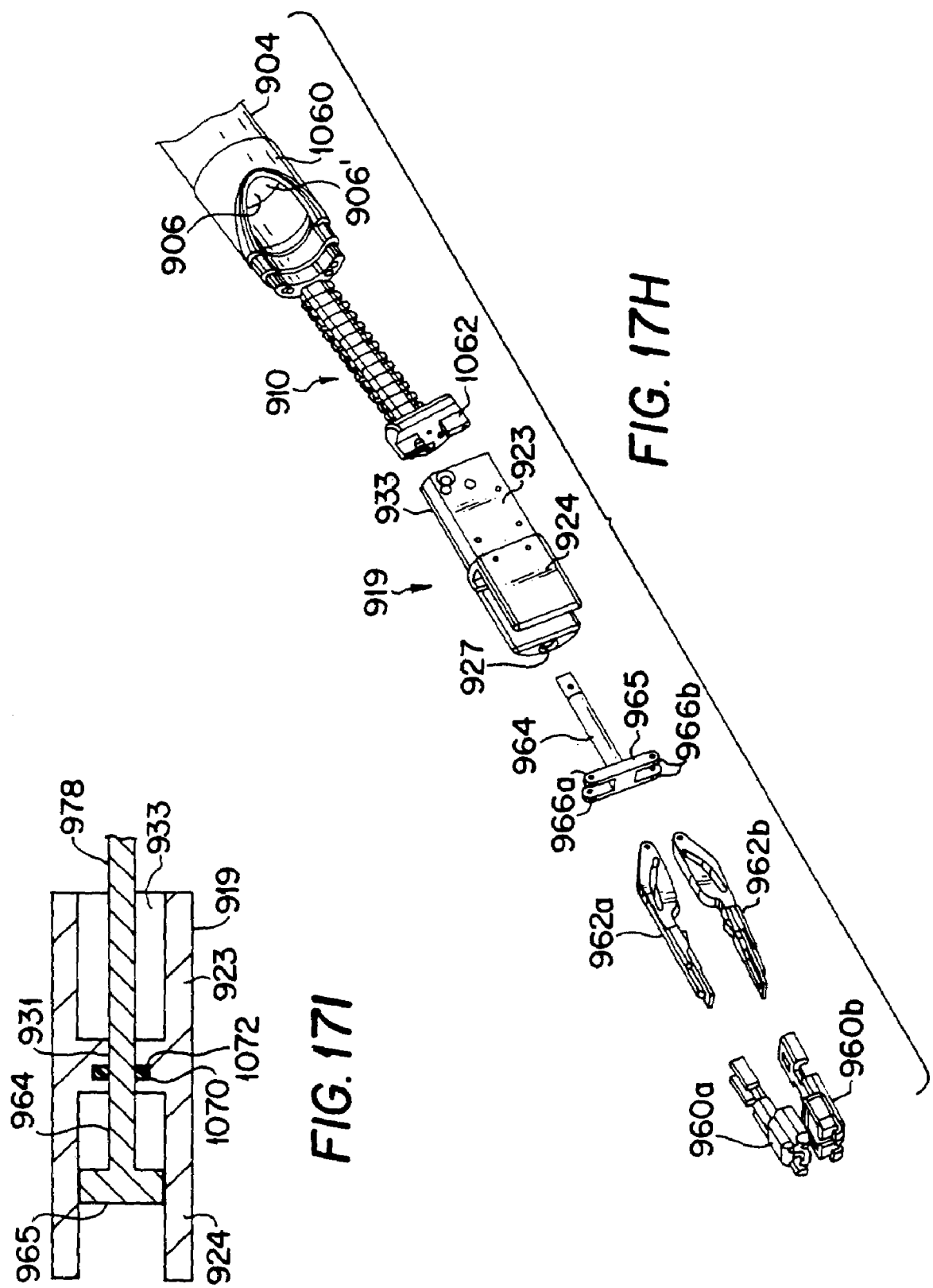

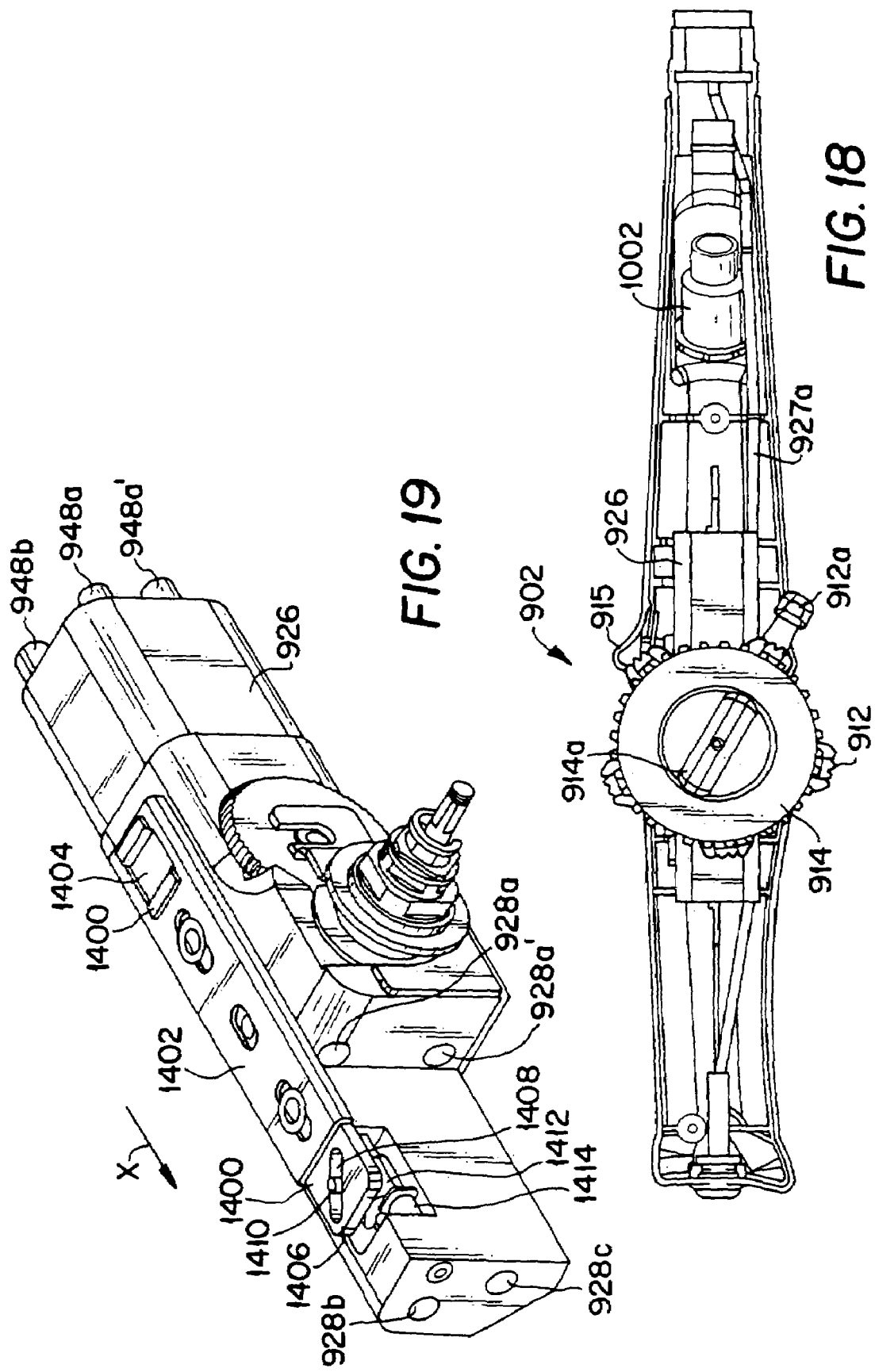

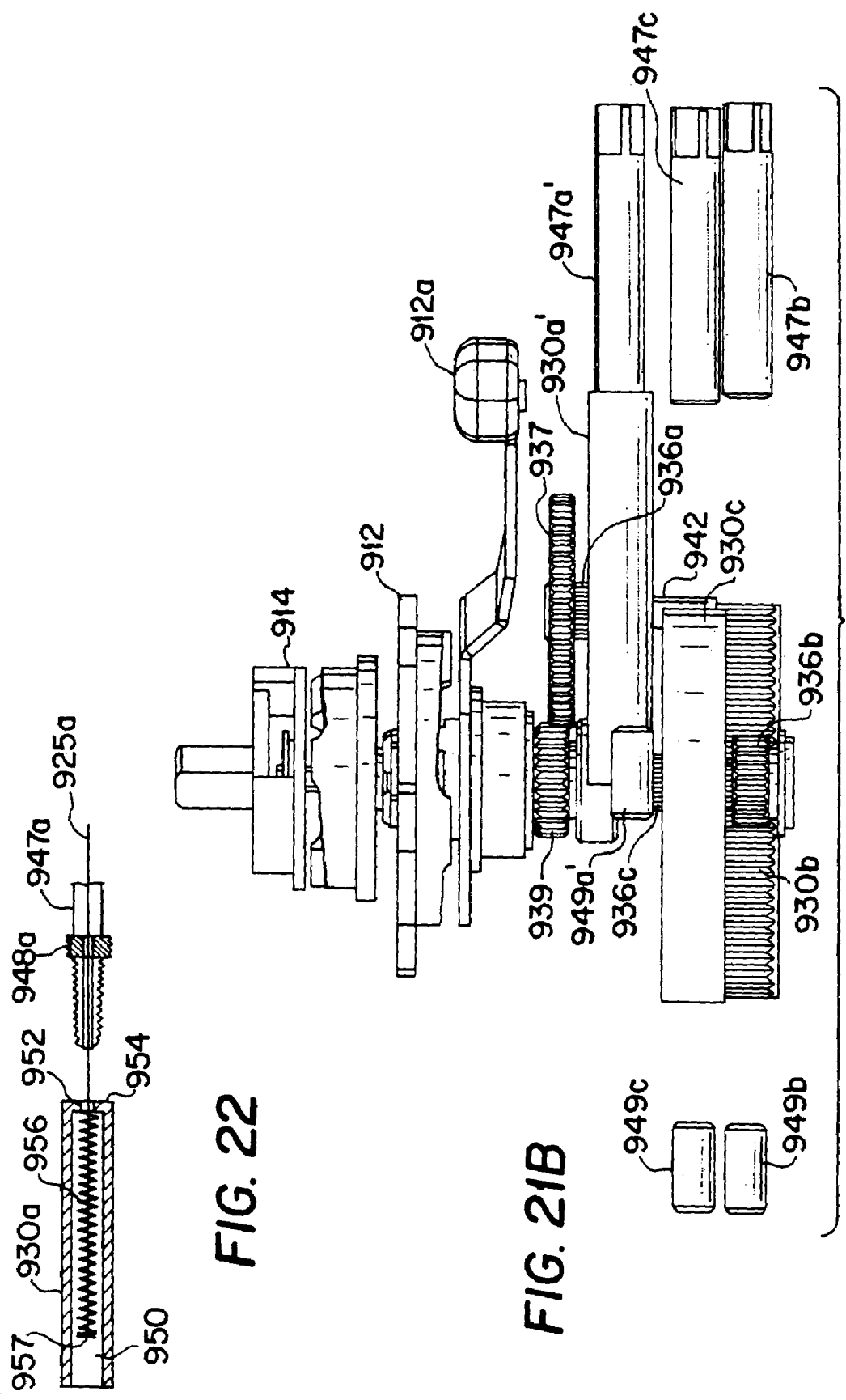

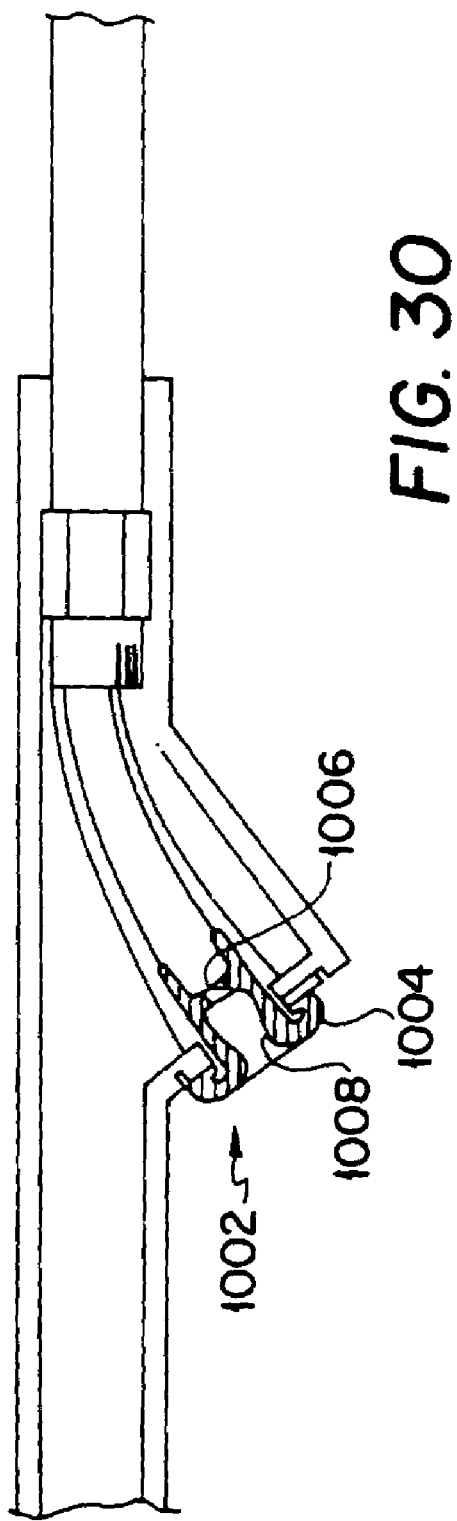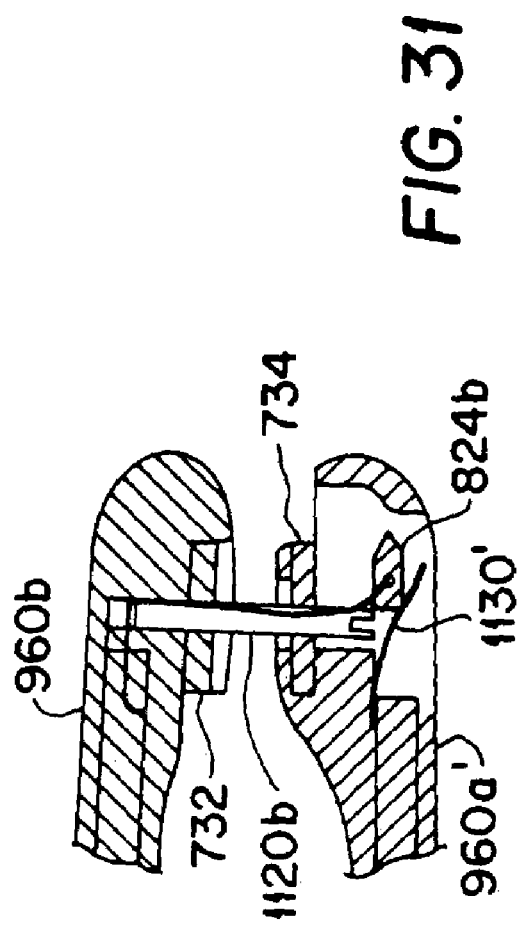

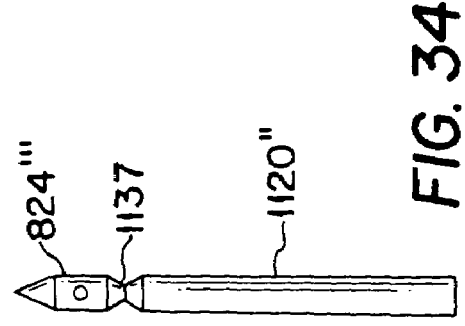
FIG. 34
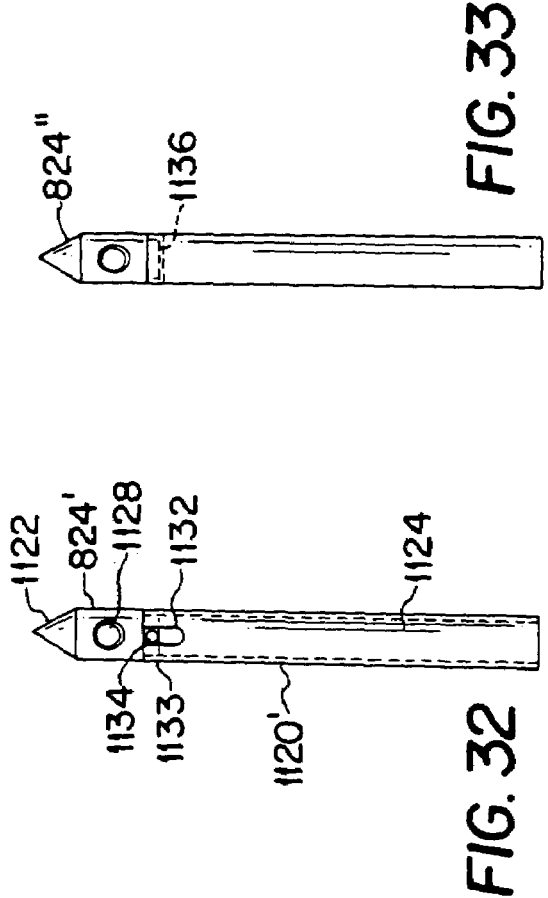
FIG. 33
FIG. 32
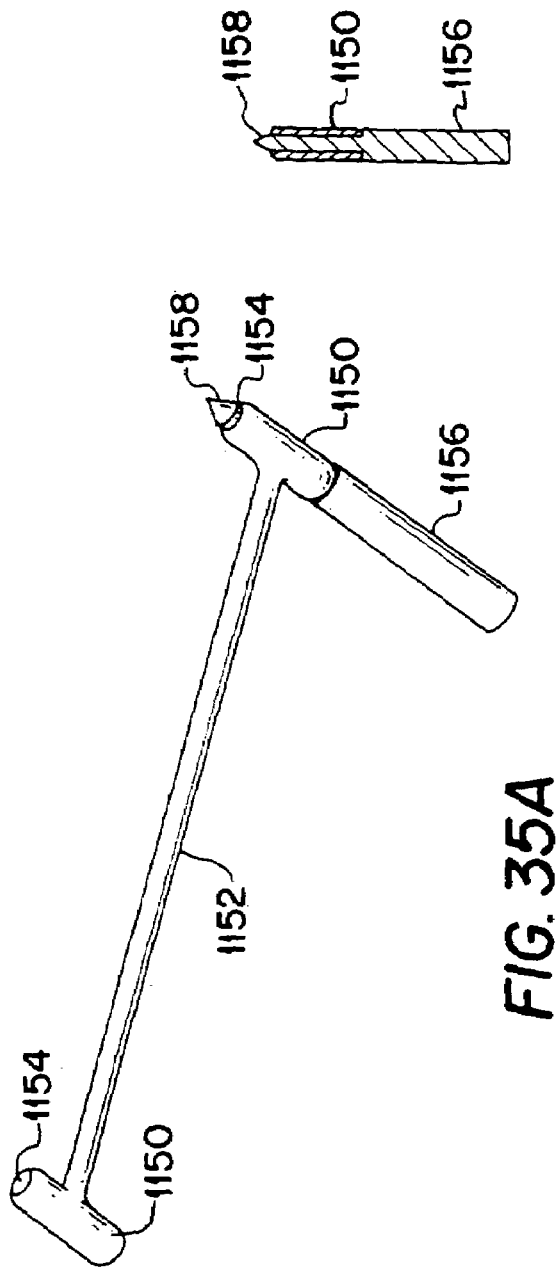
FIG. 35B
FIG. 35A

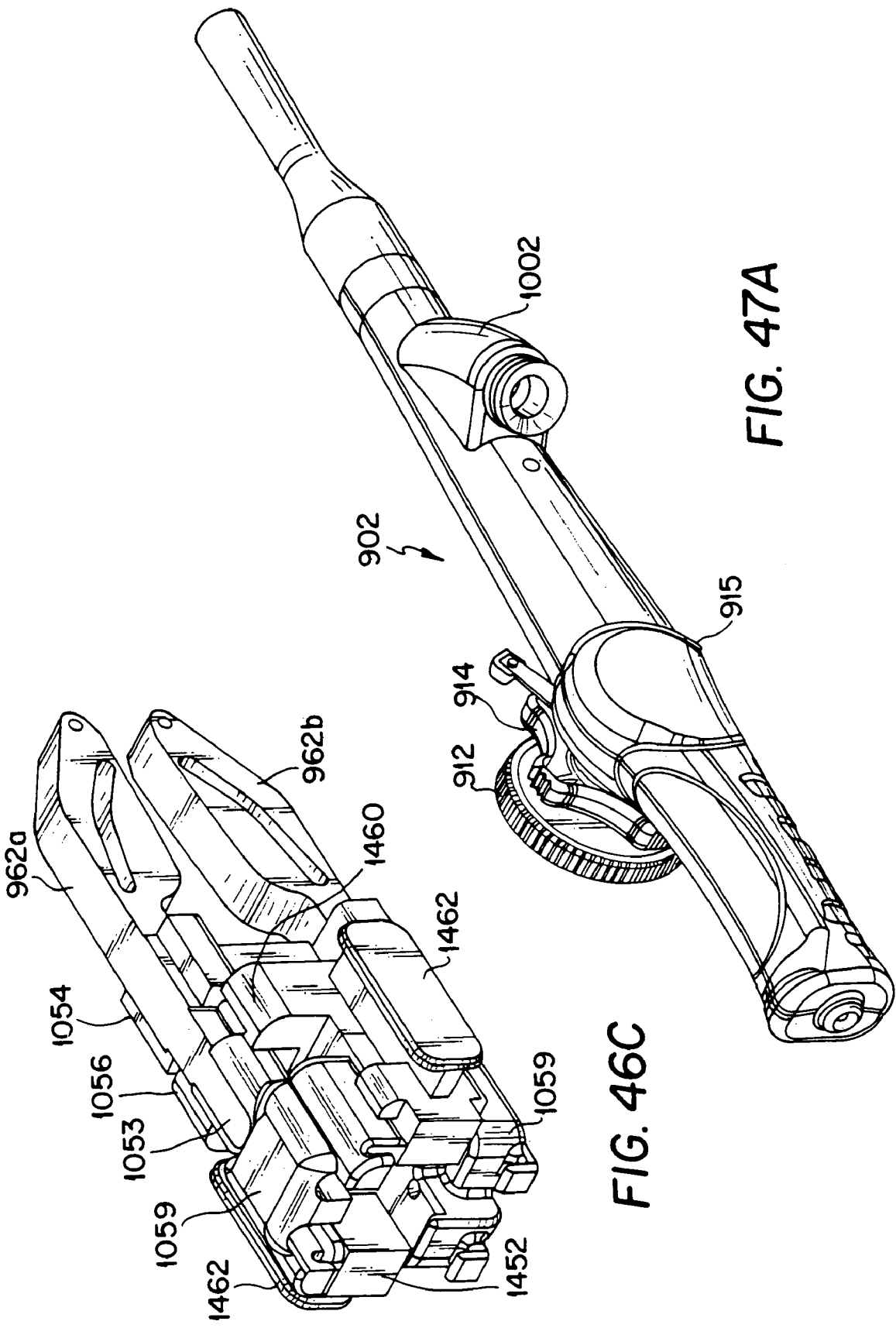

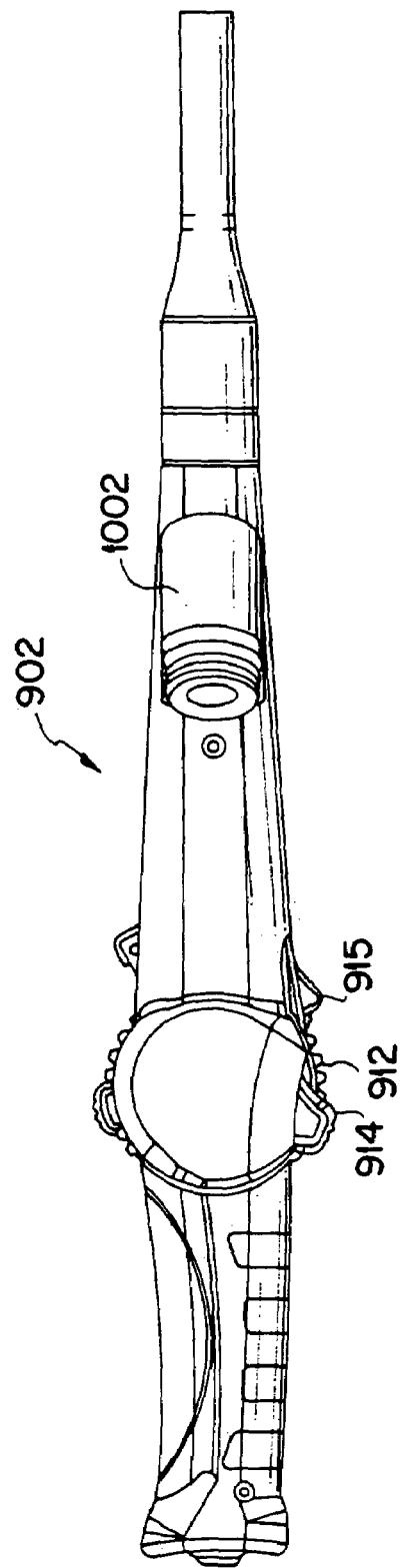
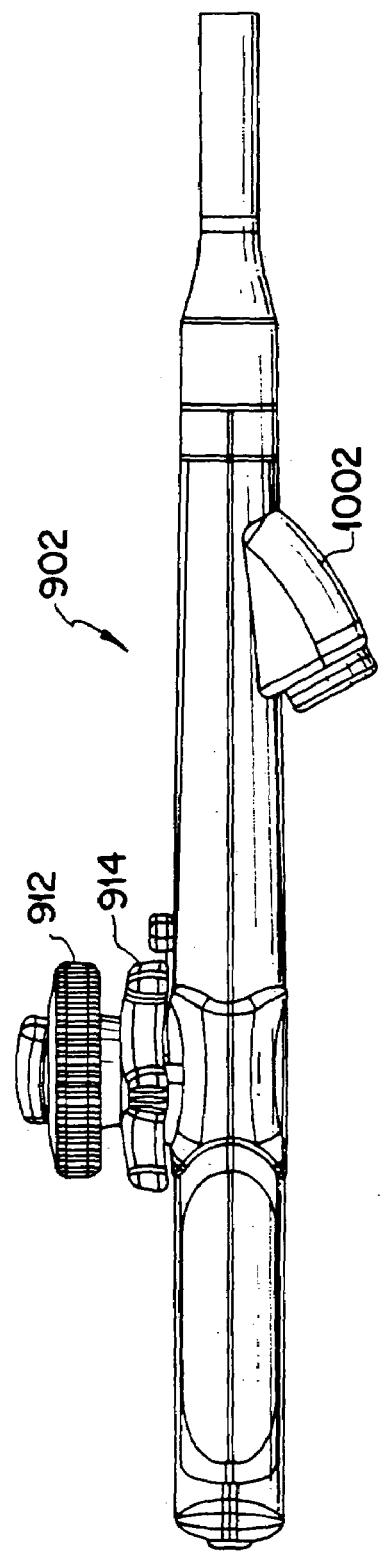
FIG. 47D
FIG. 47E

TISSUE RECONFIGURATION

CROSS REFERENCE TO RELATED APPLICATIONS

This application is a continuation of U.S. application Ser. No. 09/859,579, filed May 18, 2001, now U.S. Pat. No. 6,821,285 which is a continuation-in-part of U.S. application Ser. No. 09/574,424, filed May 19, 2000, now U.S. Pat. No. 6,494,888 which is a continuation-in-part of U.S. application Ser. No. 09/520,273, filed Mar. 7, 2000, now U.S. Pat. No. 6,663,639 and U.S. application Ser. No. 09/519,945, filed Mar. 7, 2000, now U.S. Pat. No. 6,506,196 which claim priority from U.S. Application No. 60/140,492, filed Jun. 22, 1999, all hereby incorporated by reference in their entirety.

BACKGROUND

This invention relates to methods and apparatus for reconfiguring tissue, and more particularly to reconfiguring tissue in the vicinity of the gastroesophageal junction.

Gastroesophageal reflux disease (GERD) is a common upper-gastrointestinal disorder in which acidic contents of the stomach flow inappropriately from the stomach into the esophagus. Backflow of gastric contents into the esophagus results when gastric pressure is sufficient to overcome the resistance to flow that normally exists at the gastroesophageal junction (GEJ) or when gravity acting on the contents is sufficient to cause flow through the GEJ. Medication, open surgical procedures, minimally invasive surgical techniques, and endoscopic techniques are known for treating GERD.

SUMMARY

According to one aspect of the invention, a medical instrument for engaging tissue includes a flexible shaft, a tissue piercing coil at a distal portion of the shaft, and a member positioned over the shaft. The member and the coil are coupled for relative movement.

Embodiments of this aspect of the invention may include one or more of the following features. The member is biased, e.g., by a spring, in a distal direction. The shaft includes a length of coil. The shaft coil and the tissue piercing coil are wound in opposite directions.

According to another aspect of the invention, a medical instrument for engaging tissue includes a flexible shaft, a tissue piercing member at a distal portion of the shaft, and a tissue stabilizer coupled to the shaft for movement relative to the tissue piercing member. The tissue stabilizer is biased in a distal direction such that as the tissue piercing member enters tissue, the tissue stabilizer is urged against a surface of the tissue.

According to another aspect of the invention, a medical instrument for engaging tissue includes a tissue piercing coil, and a tissue stabilizer coupled to the coil for movement relative to the coil. The tissue stabilizer is biased in a distal direction such that as the coil enters tissue, the tissue stabilizer is urged against a surface of the tissue.

According to another aspect of the invention, a method of treatment includes advancing a flexible shaft to a treatment site, and piercing tissue with a coil portion of the shaft.

According to another aspect of the invention, a method of treatment includes advancing a flexible shaft to a treatment site, piercing tissue with a member located at a distal portion of the shaft, and stabilizing tissue being pierced by contacting a surface of the tissue with a tissue stabilizer biased in a distal direction such that as the tissue piercing member enters tissue, the tissue stabilizer is urged against the surface of the tissue.

According to another aspect of the invention, a method of treatment includes piercing tissue with a coil, and stabilizing tissue being pierced by contacting a surface of the tissue with a tissue stabilizer biased in a distal direction such that as the coil enters tissue, the tissue stabilizer is urged against the surface of the tissue.

According to another aspect of the invention, a medical instrument for reconfiguring tissue includes a flexible shaft defining a lumen housing actuating controls, and a distal actuating assembly. The distal actuating assembly includes a sealing portion configured to substantially seal the shaft lumen from contact with bodily fluids, and a tissue manipulator located distal of the sealing portion. The actuating member is coupled to the tissue manipulator such that the tissue manipulator is actuatable to deploy an implant located distal of the sealing portion.

Embodiments of this aspect of the invention may include one or more of the following features. The distal actuating assembly includes an implant located distal of the sealing portion. The sealing portion includes a cover over a section of the assembly. The sealing portion includes a seal surrounding an actuating member extending through the seal.

According to another aspect of the invention, a medical device includes first and second members and each member includes a body having a first attachment portion and a second attachment portion. The first attachment portion includes a member with a side wall defining a slot and a mating contour having a straight, proximal edge for releasably attaching the body to a distal portion of a medical instrument such that the body can be exchanged with a replacement body. The second portion is configured to releasably receive an implant.

Embodiments of this aspect of the invention may include one or more of the following features. The first attachment portion includes a flexing section between the side wall and the mating contour. The second portion includes tubes configured to pass through tissue.

According to another aspect of the invention, a medical device includes an implant including a suture, and first and second members configured to releasably attach to a distal portion of a medical instrument such that the members can be exchanged with replacement members. At least one of the members is configured to releasably receive the implant for delivery of the implant to a treatment site.

According to another aspect of the invention, a cartridge assembly includes first and second members configured for releasable attachment to a medical instrument, and a holder configured to receive the first and second members and to be released from the first and second members upon action of the first and second members attaching to the medical instrument.

The instrument and method of the invention advantageously provide an endoscopic approach to treating GERD that does not require the surgical formation of portals to access the GEJ. The procedure can be performed as an outpatient procedure done under sedation, without general anesthesia being required. The procedure can be performed by gastroenterologists rather than a surgeon, and takes less time, has fewer complications and side-effects and has lower overall procedure costs than surgical methods. The procedure recreates or augments the natural anatomy, and is easily reversible. The procedure creates a gastric plication without the need for the operator to tie knots.

Of particular advantage is that portions of the instrument that engage tissue can be provided sterile, while the remainder of the instrument only need be disinfected between procedures. In addition, a tissue engagement member of the instrument provides a safe and reliable means for remotely retracting tissue.

Other features, objects, and advantages of the invention will be apparent from the following detailed description, and from the claims.

DESCRIPTION OF DRAWINGS

FIG. 5 is a side view of the distal end of the instrument, turned 90 degrees relative to FIG. 4A;

FIG. 6A is an illustration of a first part of the tissue fixation device of FIG. 2;

FIG. 6B is an illustration of the first jaw member with the first part of the tissue fixation device mounted to the jaw member;

FIGS. 9A-9F show the instrument of FIG. 1 in use;

FIG. 12C is a cross-sectional view of the tissue engaging member of FIG. 12A;

FIG. 12D is a cross-sectional view of the tissue engaging member of FIG. 12A shown piercing tissue;

FIG. 13A is an isometric view of a proximal end the tissue engaging member of FIG. 12A and a torque generator;

FIG. 13B is a cross-sectional view of the torque generator of FIG. 13A;

FIG. 14A is an illustration of an alternative tissue engaging member;

FIG. 14B is an illustration of an alternative tissue engaging member including a tissue bulking needle;

FIG. 14C is a further illustration of the tissue engaging member of FIG. 14B;

FIG. 17A is an isometric view of the distal end portion of the instrument of FIG. 16A FIG. 17B shows the distal end portion of the instrument with a hood member removed;

FIGS. 17C-17E are side views of an end effector of the instrument of FIG. 16A;

FIG. 17F is a side view of a lock arm taken along lines 17F-17F in FIG. 17E;

FIG. 17G is an illustration of disposable components of the instrument of FIG. 16A;

FIG. 17H is an exploded view of the instrument of FIG. 16A;

FIG. 17I is a cross-sectional view of a coupling member of the end effector;

FIG. 18 is a side view of a handle of the instrument of FIG. 16A, shown with a cover removed;

FIG. 19 is an isometric view of a gearbox located in the handle of FIG. 18;

FIGS. 21A and 21B are end and side views, respectively, of the mechanism of FIG. 20;

FIG. 22 is a cross-sectional view of a rack of the mechanism of FIG. 20;

FIG. 30 is an illustration of a seal on the handle of FIG. 18;

FIG. 31 is an illustration of an alternative deployment mechanism;

FIGS. 32-34 are illustrations of alternative means for coupling the implant bar to the tube of the jaw member;

FIG. 35A is an isometric view and FIG. 35B is a cross-sectional view of an alternative tissue fixation device;

FIGS. 36A-40 are illustrations of alternative means for providing an atraumatic distal end on the instrument of FIG. 16A;

FIGS. 46A-46C are illustrations of a cartridge assembly to which the disposable cartridges of FIG. 17F are mounted for handling and attachment to the instrument; and FIGS. 47A-47F are isometric, four side views, and an end view, respectively, of the handle of FIG. 18.

DETAILED DESCRIPTION

Figure 1:
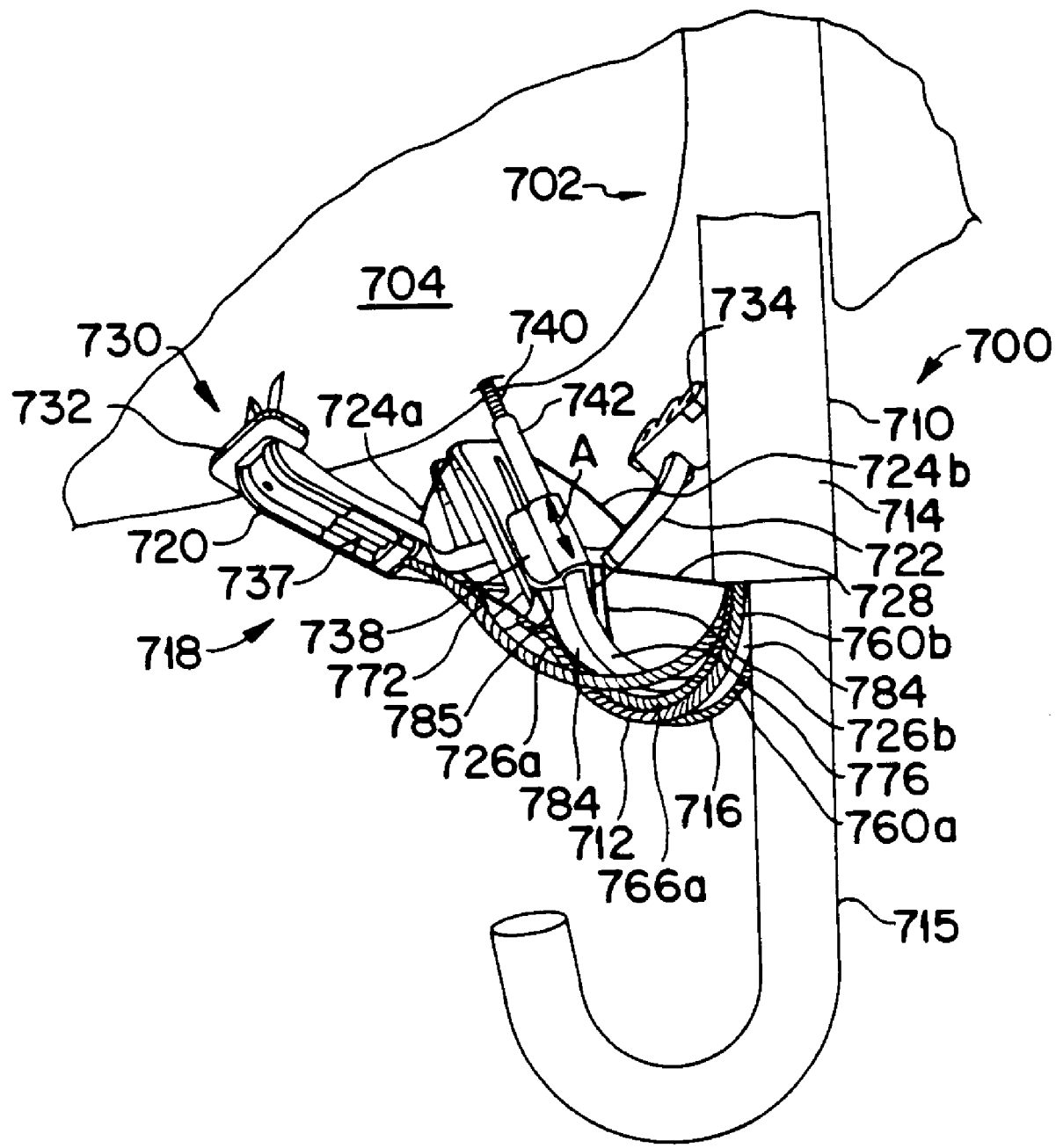
FIG. 1 is a diagrammatic representation of an instrument in use to reconfigure tissue in the vicinity of the gastroesophageal junction of the stomach.

Referring to FIG. 1, an instrument 700 for reconfiguring stomach tissue, e.g., stomach tissue in the vicinity of the gastroesophageal junction (GEJ) 702, such as tissue 704 of the lesser curvature of the stomach or any portion of the stomach within about 2 cm of the GEJ, is shown. The GEJ is the region of transition from the esophagus and the stomach. The lesser curvature of the stomach is a portion of the stomach located beyond the GEJ. Instrument 700 includes an elongated shaft 710 dimensioned to permit transoral access to the stomach, and a tissue manipulator 712 for manipulating stomach tissue. Positioned within a lumen 714 defined by shaft 710 is a standard GI endoscope 715 providing visual guidance of the reconfiguring procedure. Instrument 700 is particularly adapted for treating GERD. Using instrument 700, as described below, a bulge, plication or tissue wrap is formed in the vicinity of gastroesophageal junction 702 to reduce reflux of stomach fluids into the esophagus.

Figures 2, 3A:
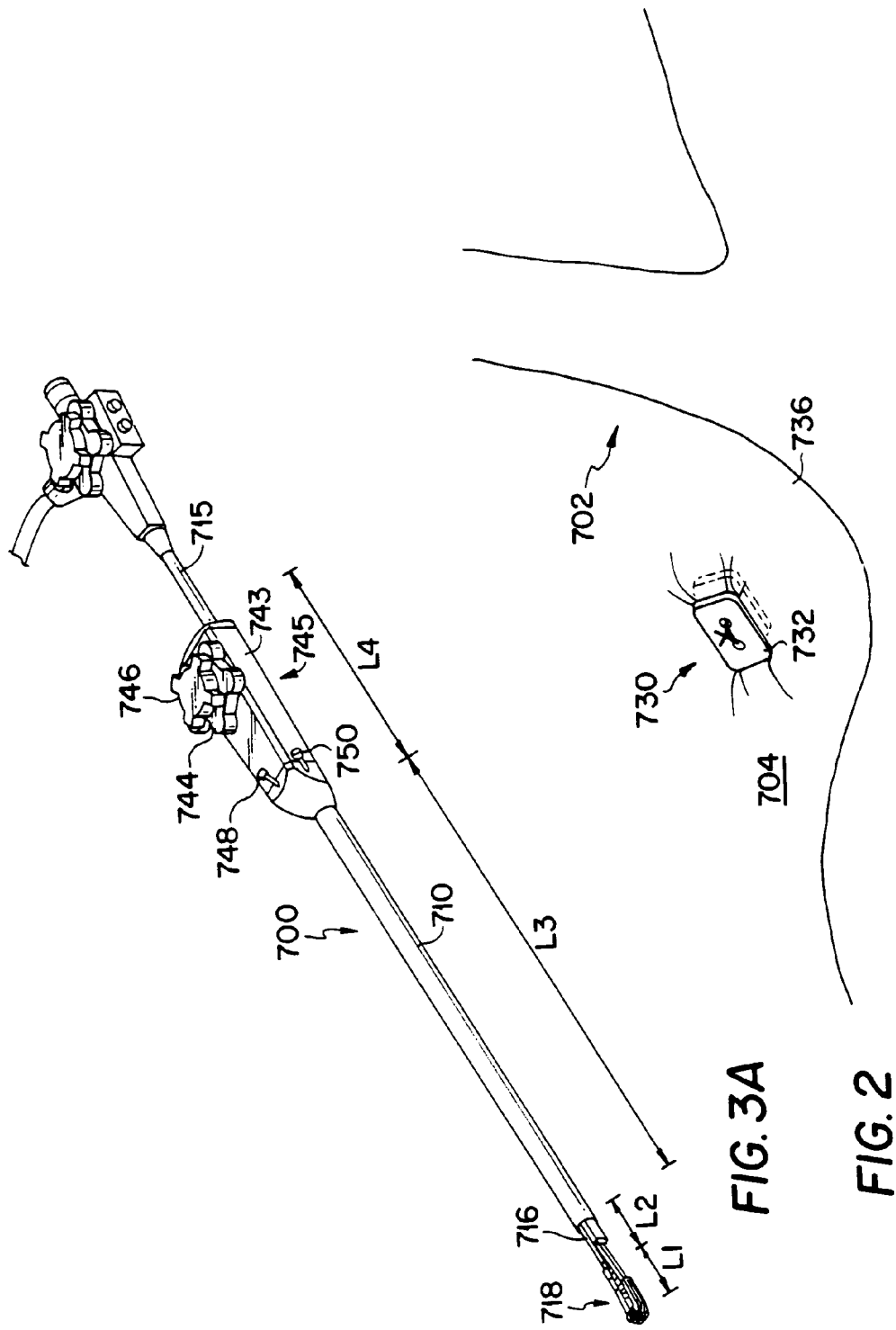
FIG. 2 shows a tissue fixation device deployed by the instrument of FIG. 1 in use to secure a bulge formed in the tissue.
FIG. 3A is an illustration of the instrument of FIG. 1.

Tissue manipulator 712 has an elongated cable assembly 716 housed within lumen 714 of shaft 710, and a distal end effector 718 actuated to perform the various steps in the tissue reconfiguring procedure by cable assembly 716. End effector 718 includes first and second jaw members 720, 722 which engage tissue 704. Cable assembly 716 includes first and second cable pairs 724a, 724b, and 726a, 726b for moving jaws 720, 722 relatively toward and away from one another, respectively, in a first plane, and a third cable 728 for moving end effector 718 relative to shaft 710 in a second plane generally transverse to, and preferably perpendicular to, the first plane, as described further below. During insertion into the stomach, end effector 718 is aligned with shaft 710 (as shown in FIG. 3A). Once positioned in the stomach, cable 728 is actuated to articulate end effector 718 out of alignment with shaft 710 (as shown in FIG. 1).

Cable assembly 716 includes a spring beam 784, formed from, e.g., stainless steel or Nitinol, extending into shaft 710. End effector 718 is attached to beam 784 at a distal end 785 of beam 784. Beam 784, in its rest state, is biased toward a straight alignment. Pulling cable 728 bends beam 784. When cable 728 is released, beam 784 returns toward the straight alignment.

Referring also to FIG. 2, mounted to first jaw 720 is a first part 732 of a tissue securement member, e.g., a fixation device 730, and mounted to second jaw 722 is a second part 734 of tissue fixation device 730. As described further below, after jaws 720, 722 engage tissue 704 and manipulate the tissue in a wrapping action to create a bulge 736 in, e.g., the lesser curvature of the stomach, tissue fixation device 730 is deployed to secure the engaged tissue together. Cable assembly 716 includes a fourth cable 737 for deploying fixation device 730, as described further below.

End effector 718 further includes a tube 738 and a third tissue engaging member, e.g., a coil 740, received within tube 738, for purposes described below. Coil 740 is housed within an overtube 742, and coil 740 and overtube 742 can be moved axially proximally and distally relative to jaws 720, 722, along the axis, A, of cable assembly 716. Coil 740 can be rotatably advanced into tissue.

Figure 3B:
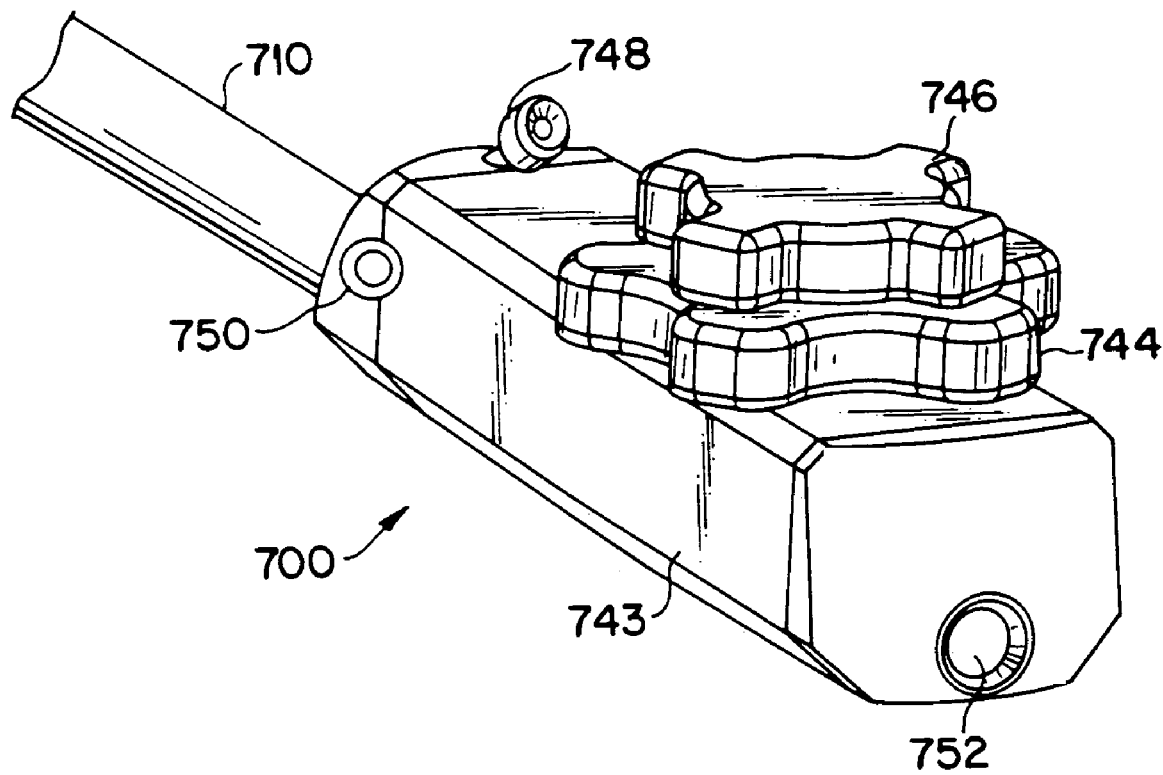
FIG. 3B shows a proximal end of the instrument.

Referring to FIG. 3A, instrument 700 has, at its proximal end 745, a handle 743 with a control knob 744 for controlling cables 724a, 724b, 726a, 726b to close and open jaws 720, 722, and a control knob 746 for controlling cable 728 to move end effector 718. Handle 743 includes a port 748 through which coil 740 and overtube 742 can be introduced into shaft lumen 714, and a pull-knob 750 for deploying tissue fixation device 730, as described below. As shown in FIG. 3B, handle 743 defines a channel 752 through which endoscope 715 is introduced into shaft lumen 714.

Figure 3C:
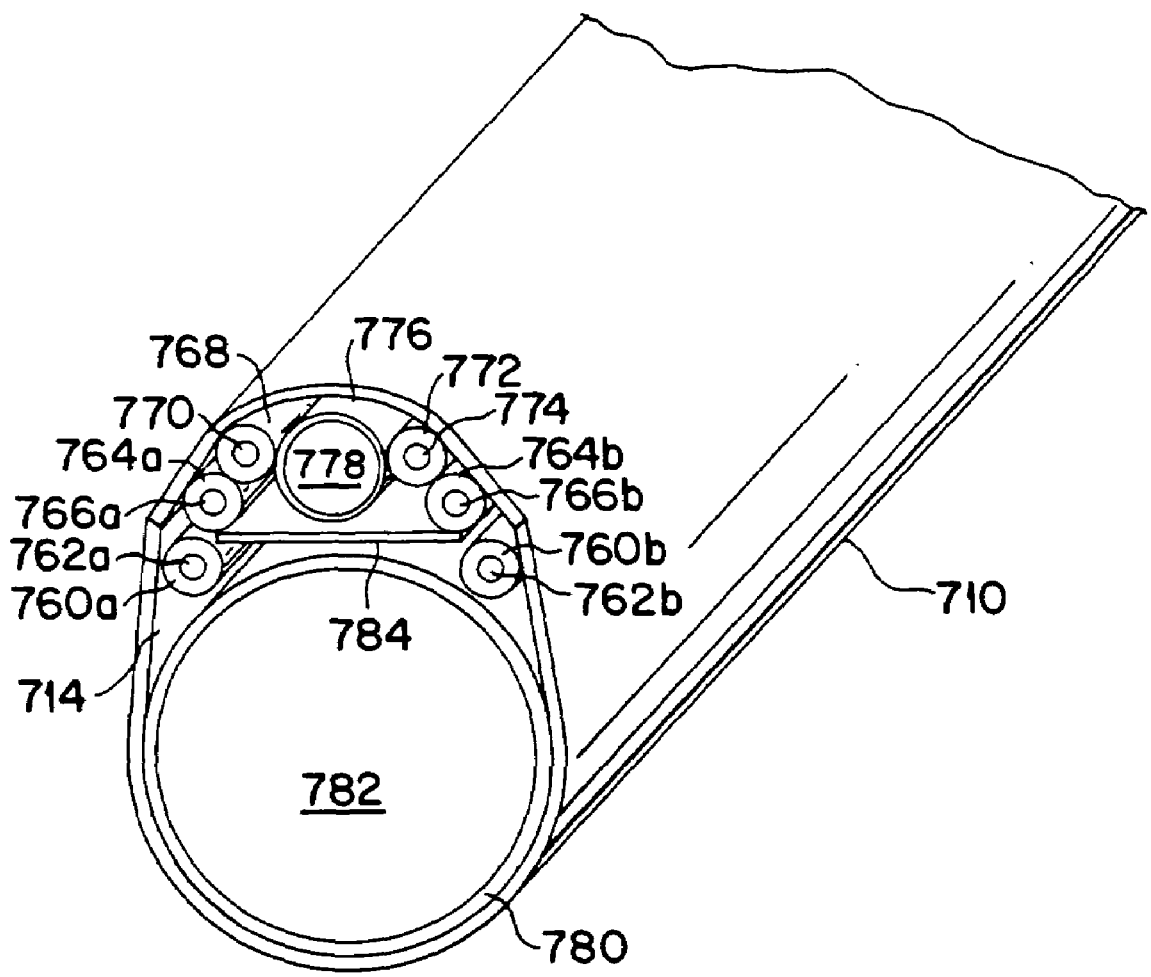
FIG. 3C shows the working channels in a shaft of the instrument.
Figure 3D:
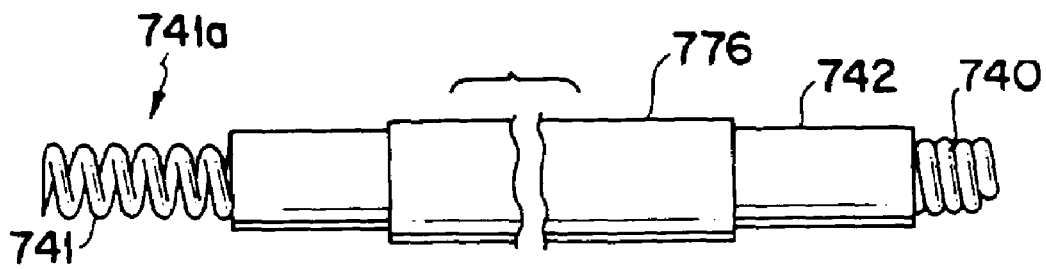
FIG. 3D is an illustration of a coil assembly of the instrument.

Referring to FIGS. 1 and 3C, which shows the working channels in shaft 710 for receiving the various cables, overtube 742 and endoscope 715, within lumen 714 of shaft 710 are cable housings 760a, 760b defining channels 762a, 762b in which cables 724a, 724b for closing jaws 720, 722 are received, and cable housings 764a, 764b defining channels 766a, 766b in which cables 726a, 726b for opening jaws 720, 722 are received. Within lumen 714 are also a cable housing 768 defining a channel 770 in which cable 728 for bending end effector 718 is received, and a cable housing 772 defining a channel 774 in which cable 737 for deploying fixation device 730 is received. Coil 740 and overtube 742 are received in a channel 778 defined in a coil housing 776 in lumen 714. Housing 776 extends from port 748 to tube 738. As shown in FIG. 3D, coil 740 has a tissue penetrating tip 741 and a distal section 740a having a looser wound coil than the remainder of coil 740. Endoscope 715 is received in a channel 782 defined in an endoscope housing 780 in lumen 715.

Spring beam 784 is located generally between cable housing 776 and endoscope housing 780, and extends about 4 inches into shaft 710 from the distal end of the shaft where beam 784 is mounted to shaft 710 by, e.g., silicone adhesive/sealant. The various cable housings and spring beam 784 do not move relative to shaft 710 and handle 743. It is the movement of the cables within the cable housings that actuate end effector 718. Shaft 710 is preferably formed from, e.g., heat-shrink tubing.

Referring again to FIG. 3A, end effector 718 has a length, L1, of about 2 inches, cable assembly 716 extends axially by a length, L2, of about 2.5 inches from shaft 710, shaft 710 has a length, L3, of about 23.5 inches, and handle 743 has a length, L4, of about 5 inches. Cable assembly 716, spring beam 784, and shaft 710 have the necessary flexibility to permit transoral placement of instrument 700 into the stomach. The length, L1, of relatively rigid end effector 718 is minimized to ensure the necessary flexibility of instrument 700 is maintained. The distance that cable assembly 716 extends axially from shaft 710 is selected to cantilever beam 784 permitting the desired bending of end effector 718 relative to shaft 710 to position jaws 720, 722 against the inner surface of the stomach in the vicinity of the GEJ.

Distal end effector 718 is sized to fit through a 12-16 mm diameter channel (corresponding to the diameter of the esophagus) and shaft 710 has an outer diameter of about 12 to 16 mm to enable transoral passage of instrument 700 into the stomach. Scope channel 782 has a diameter of either about 8 mm or 10 mm. An 8 mm diameter scope channel allows passage of 7.9 mm pediatric gastroscope, and a 10 mm diameter scope channel allows passage of a 9.8 mm adult gastroscope. Channel 778 has a diameter of about 2-3 mm for receiving cable 742.

Figure 4A:
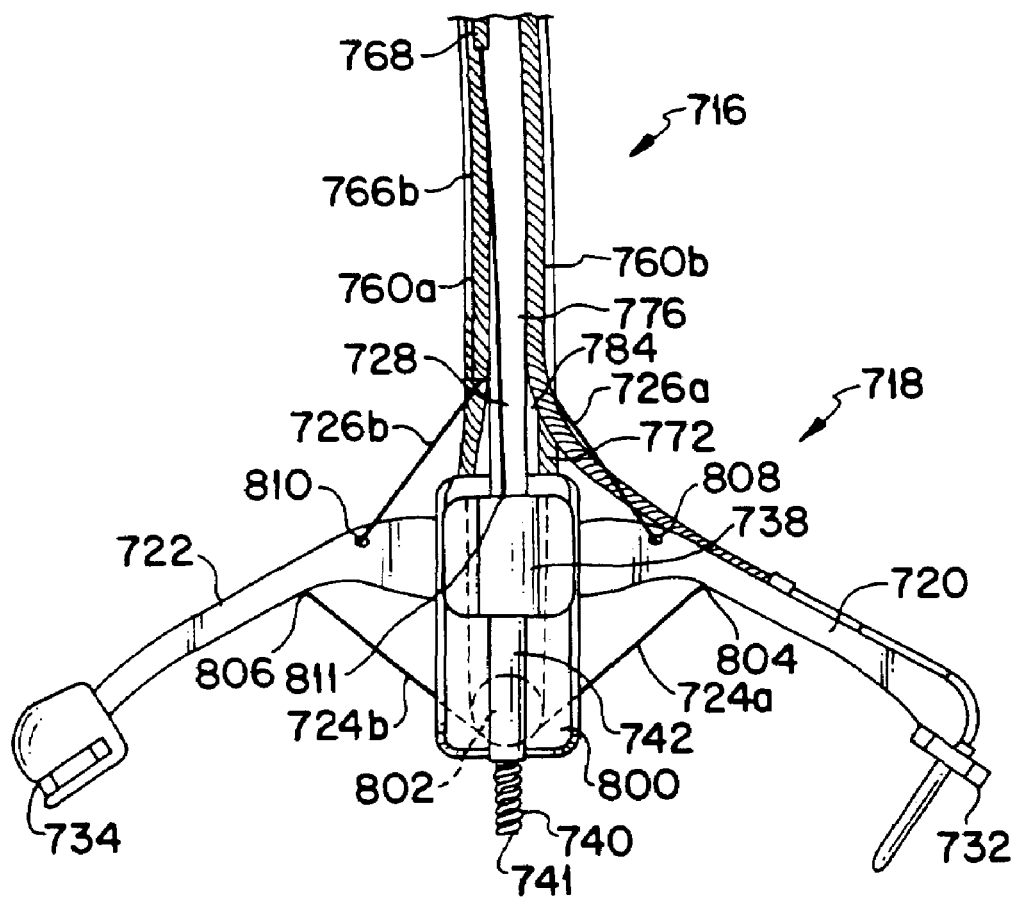
FIG. 4A is a top view of a distal end of the instrument, shown with first and second jaw members in an open position.
Figure 4B:
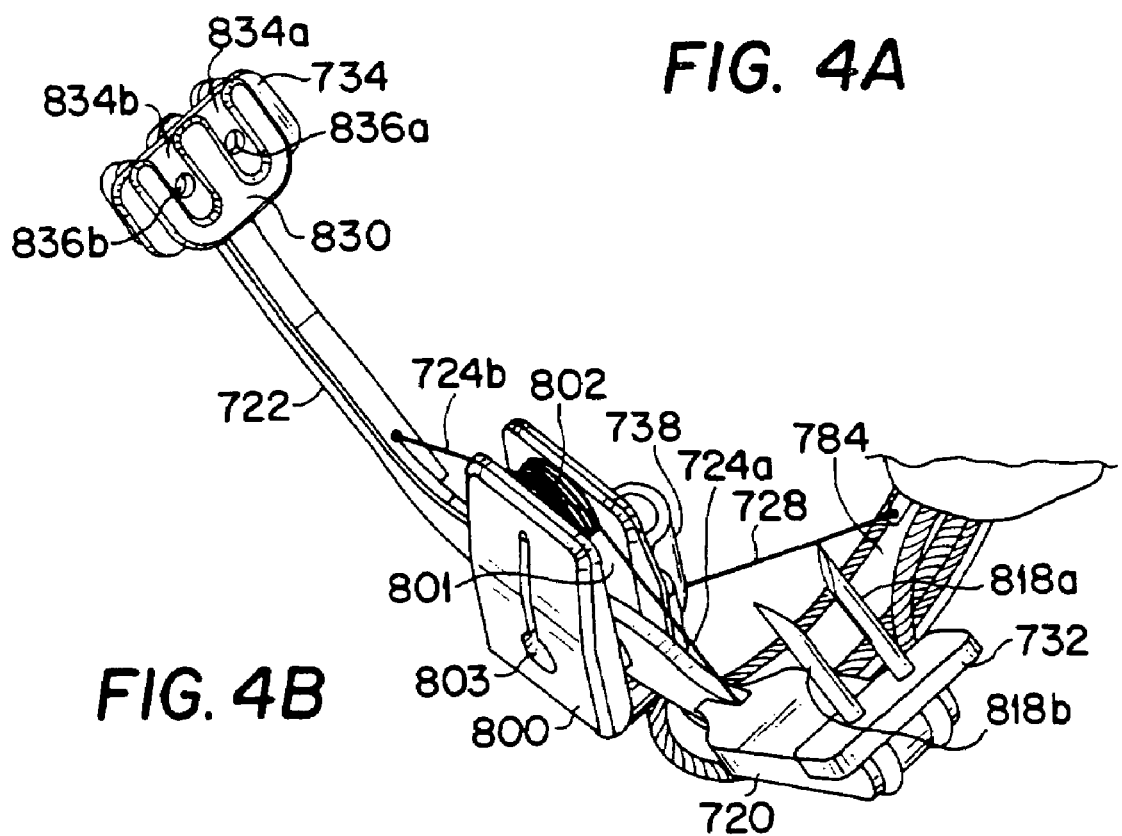
FIG. 4B shows the distal end of the instrument located off-axis relative to a shaft of the instrument.

Distal end effector 718 is shown in more detail in FIGS. 4A and 4B. End effector 718 includes a central mount 800 defining a slot 801. Spanning slot 801 and supported by mount 800 is a pin 803 to which 720, 722 are pivotally mounted. Central mount 800 also houses two pulleys 802 over which cables 724a, 724b are respectively passed for closing jaws 720, 722. Cables 724a, 724b terminate at points 804, 806 on jaws 720, 722, respectively. Cables 726a, 726b for opening jaws 720, 722 terminate at points 808, 810 on jaws 720, 722, respectively, proximal of points 804, 806. Tube 738 of end effector 718 for receiving coil 740 and overtube 742 is attached to mount 800, and cable 728 for bending end effector 718 terminates at point 811 on tube 738.

Pulling cables 724a, 724b proximally moves jaws 720, 722 toward one another generally in a first plane (in the plane of the paper in FIG. 4A). Pulling cables 726a, 726b proximally moves jaws 720, 722 away from one another generally in the first plane. Pulling cable 728 proximally bends beam 784 moving end effector 718 in a second plane (out of the plane of the paper in FIG. 4A) generally perpendicular to the first plane.

Referring also to FIG. 5, jaw 720 includes two guide tubes 816a, 816b and a slider 812 including two push rods 814a, 814b guided within tubes 816a, 816b, respectively. Slider 812 is mounted to jaw 720 to slide relative to jaw 720. Tubes 816a, 816b curve about jaw 720 to terminate in tissue penetrating tips 818a, 818b (FIG. 6B), respectively. Push rods 814a, 814b can be formed from molded plastic such as polyethylene or polypropylene or as a braided stainless steel cable to provide the flexibility to follow the curve of tubes 816a, 816b. Cable housing 772 is attached to slider 812 and cable 737 terminates at a fixed point 739 on jaw 720. Actuation of cable 737 pushes slider 812 distally, as described below.

First part 732 of tissue fixation device 730 is shown in more detail in FIGS. 6A and 6B. First part 732 of tissue fixation device 730 defines through holes 820a, 820b (FIG. 6A), and part 732 is loaded onto jaw 720 with tips 818a, 818b received in through holes 820a, 820b, respectively. Connected to part 732 with a suture 822 are two securing elements, e.g., bars 824a, 824b. Each bar 824a, 824b defines two through holes 826a, 826b. Suture 822 is threaded through holes 826a, 826b of the bars and through holes 820a, 820b of part 732, and is tied together forming a knot 823 to secure bars 824a, 824b to part 732. Tubes 818a, 818b each define a channel 827 for receiving one of bars 824a, 824b, and a slot 828 communicating with channel 827 for receiving suture 822 therethrough.

Figure 7:
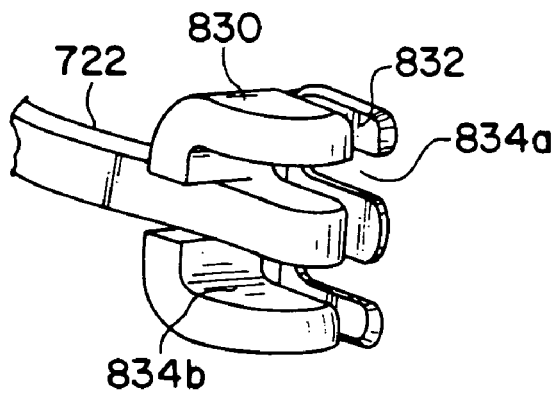
FIG. 7 is an illustration of the second jaw member.
Figure 8:
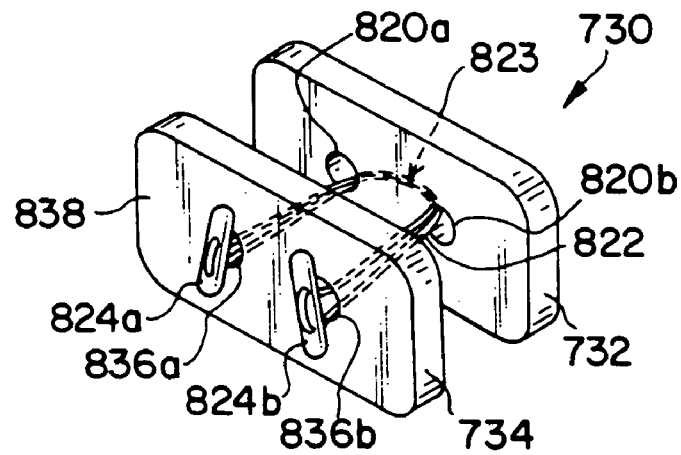
FIG. 8 is an illustration of the tissue fixation device of FIG. 2.

Referring particularly to FIGS. 4B and 7, jaw 722 has a distal member 830 defining a slot 832 for receiving second part 734 of fixation device 730, and slots 834a, 834b for receiving tissue penetrating tips 818a, 818b. Second part 734 of fixation device 730 defines through holes 836a, 836b for receiving tips 818a, 818b. When jaws 720, 722 are closed, tips 818a, 818b pass through slots 834a, 834b and holes 836a, 836b. Actuation of fixation device deployment cable 737 after closing jaws 720, 722 pushes slider 812 and push rods 814a, 814b distally, advancing bars 824a, 824b out of tissue penetrating tips 818a, 818b, and locating bars 824a, 824b on the far side 838 of second part 734 of fixation device 730, as shown in FIG. 8.

Figure 9A:
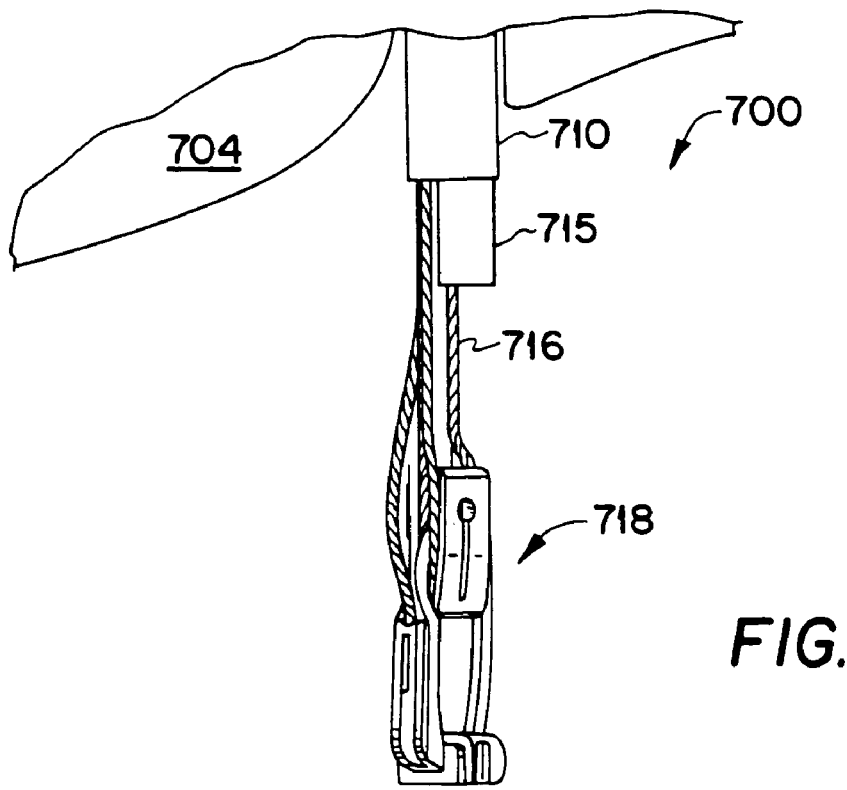

Referring to FIGS. 9A-9F, in use, under endoscopic guidance, the physician advances instrument 700 transorally to position end effector 718 in the stomach. During advancement into the stomach, end effector 718 is generally aligned along the axis of shaft 710, as shown in FIG 9A. The physician then turns control knob 746 to pull cable 728 proximally, thereby bending beam 784 moving end effector 718 out of alignment with shaft 710 to the position shown in FIG. 9B. By then turning control knob 744 to pull cables 726a, 726b, jaws 720, 722 are pivoted about pins 803 to the open position shown in FIG. 9C.

Figure 9D:
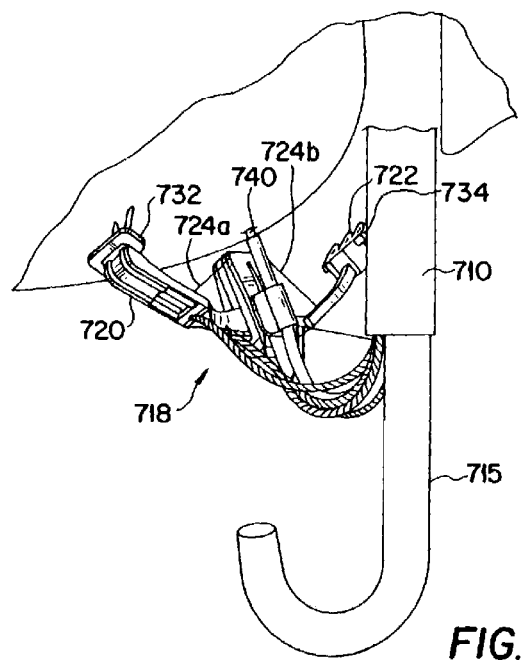
Figure 9E:
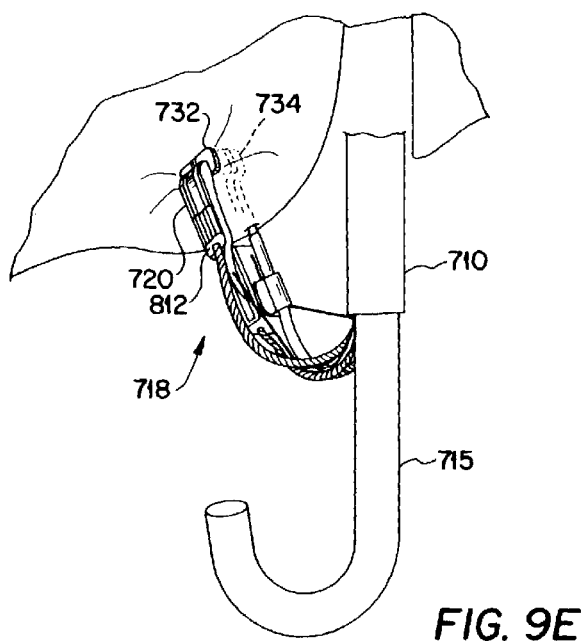

The physician then advances coil 740 and overtube 742 by pushing the coil and overtube distally in channel 778 advancing coil 740 and overtube 742 out of tube 738 and into contact with stomach tissue, preferably stomach tissue beyond the gastroesophageal junction, as shown in FIG. 1. With overtube 742 pressing against the tissue to stabilize the tissue, the physician rotates coil 740 while applying slight distal pressure to advance the coil into the tissue, as shown in FIG. 9D. Coil 740 and overtube 742 are then pulled proximally to pull tissue between jaws 720, 722. Jaws 720, 722 are then closed by turning control knob 744 to pull cables 724a, 724b proximally, as shown in FIG. 9E. The turning of the control knob can also be the action that pulls coil 740 and overtube 742 proximally, ensuring that coil 740 and overtube 742 are positioned out of the way of the closing of the jaws. A lockout can be incorporated to prevent the jaws from closing if coil 740 and overtube 742 are not in their proximal position.

Figure 9F:
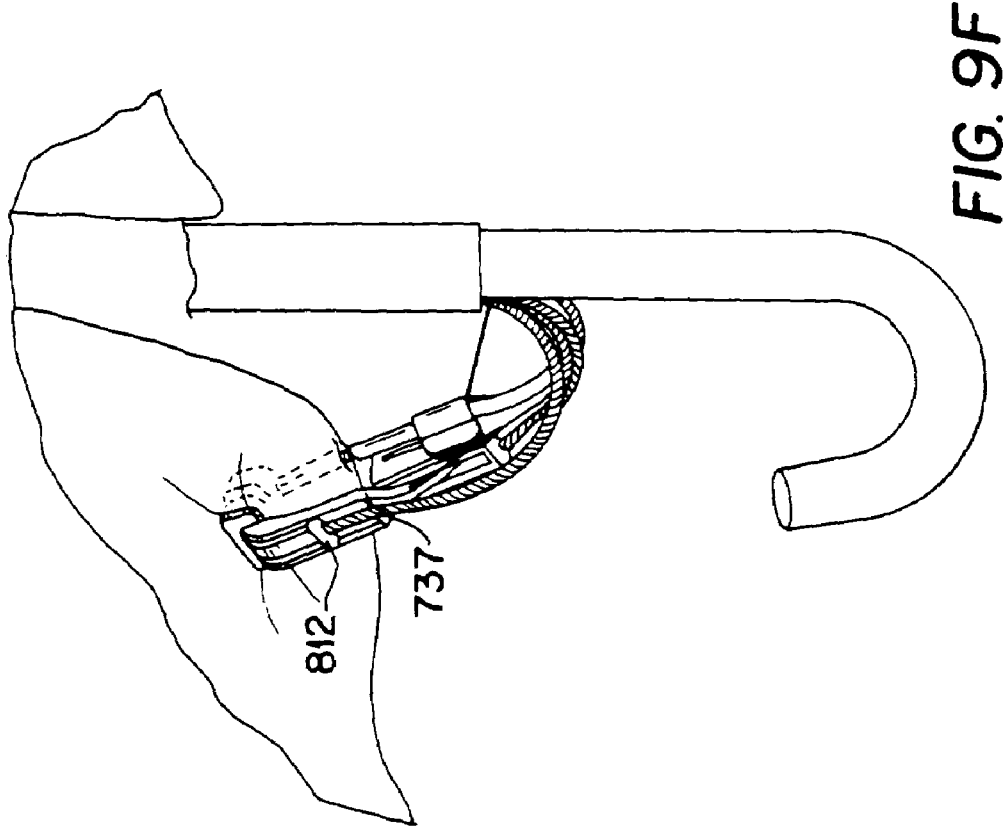

The closing of the jaws places parts 732, 734 of fixation device 730 in contact with two tissue sections, e.g., against two spaced tissue surfaces in the stomach, and causes tissue penetrating tips 818a, 818b to penetrate through the tissue and into holes 836a, 836b in second part 734 of fixation device 730. To deploy fixation device 730, the physician pulls cable 737 proximally removing slack from cable 737. Because cable housing 772 is of fixed length and is nonmovably attached to the handle, removing slack from cable 737 causes cable housing 772 to move distally, advancing slider 812 to push t-bars 824a, 824b out of tissue penetrating tips 818a, 818b, as shown in FIG. 9F.

Figure 10:
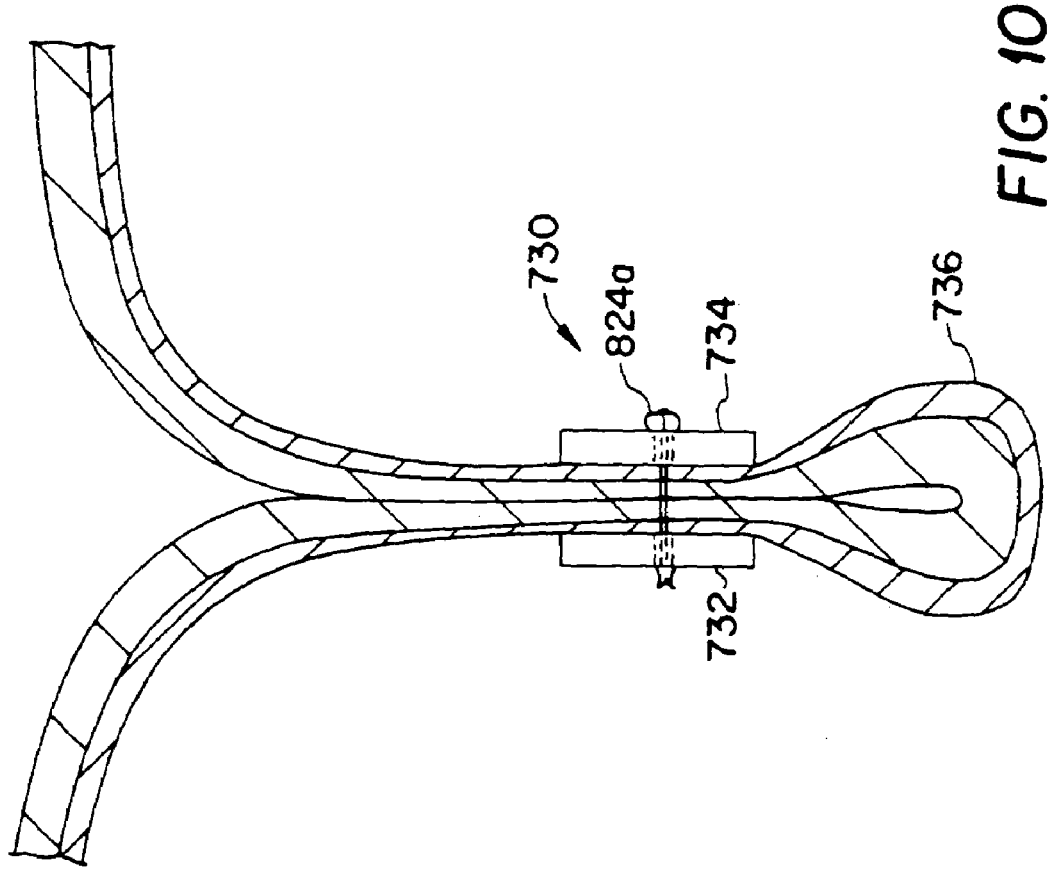
FIG. 10 is an illustration of tissue secured with the tissue fixation device of FIG. 2.

The physician then opens the jaws, disengages jaw 722 from second part 734, returns the distal end effector to its original position generally aligned with shaft 710, closes the jaws and removes instrument 700. FIG. 10 shows a cross-section of the tissue with fixation device 730 in place securing bulge 736.

Other embodiments are within the scope of the following claims.

For example, rather than a coil 740, alternative tissue penetrating or grasping elements such as a T-bar suture or two small grasping jaws can be employed. Instrument 700 can be used without the third tissue engaging member.

Figure 11A:
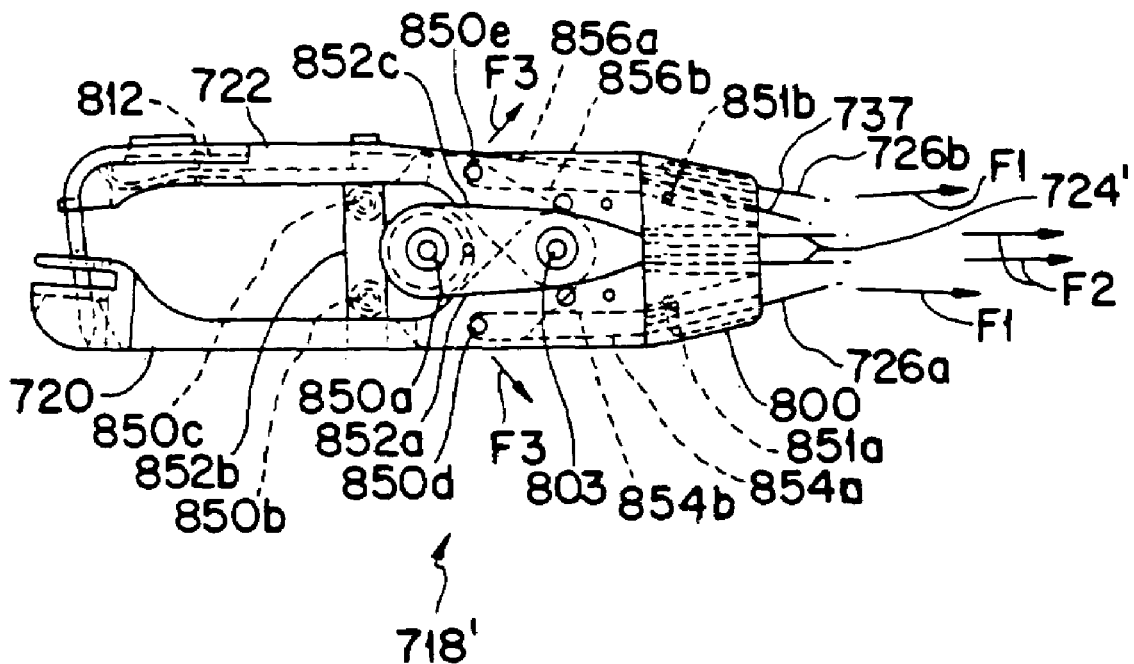
FIGS. 11A and 11B are illustrations of an alternative cable routing for an end effector.
Figure 11B:
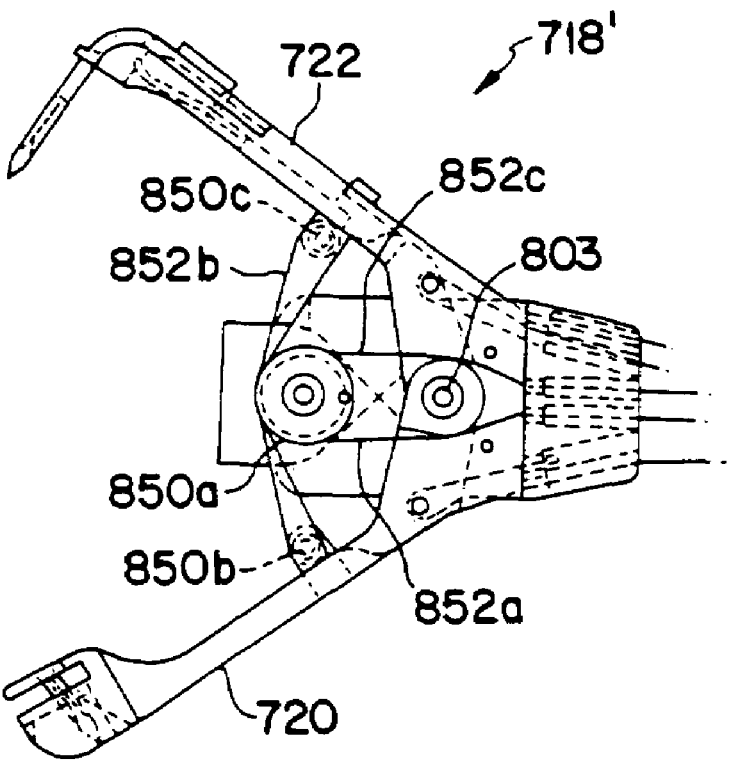

Referring to FIGS. 11A and 11B, an end effector 718' includes an alternative cable routing for actuating jaws 720, 722. End effector 718' includes cables 726a, 726b for opening jaws 720, 722, a single cable 724' for closing jaws 720, 722, and cable 737 for advancing slider 812. End effector 718' also includes pivot 803 and a series of pulleys 850a, 850b, 850c, 850d, and 850e around which the cables are routed.

Cable 724' has a first portion 852a that is routed under (as viewed in FIGS. 11A and 11B) pulley 850a and over pulley 850c; a second portion 852b that extends between pulleys 850c and 850b; and a third portion 852c routed under pulley 850b and over pulley 850a. Cable 726a has a first portion 854a that extends to pulley 850d and a second portion 854b that extends between pulley 850d and anchor 851a fixed to central mount 800. Cable 726b has a first portion 856a that extends to pulley 850e and a second portion 856b that extends between pulley 850d and anchor 851b fixed to central mount 800.

To open jaws 720 and 722, the user applies a tensile force F1 to cables 726a and 726b (by turning control knob 744). The tensile force F1 draws the first portions 854a and 856a of cables 726a and 726b proximally in the same direction as force F1 and draws the second portions 854b and 856b of cables 726a and 726b distally around respective pulleys 850e and 850d. Turning knob 744 also produces slack in cable 724'. A net force F3 results and draws jaws 720, 722 open.

To close jaws 720, 722, the user applies a tensile force F2 to portions 852a and 852b of cable 724' (by turning control knob 744 in the opposite direction, which also relieves tension in cables 726a, 726b). The tensile force F2 acts to shorten portion 852b of cable 724', thereby drawing pulleys 850c and 850b together and jaws 720, 722 closed.

Figure 12A:
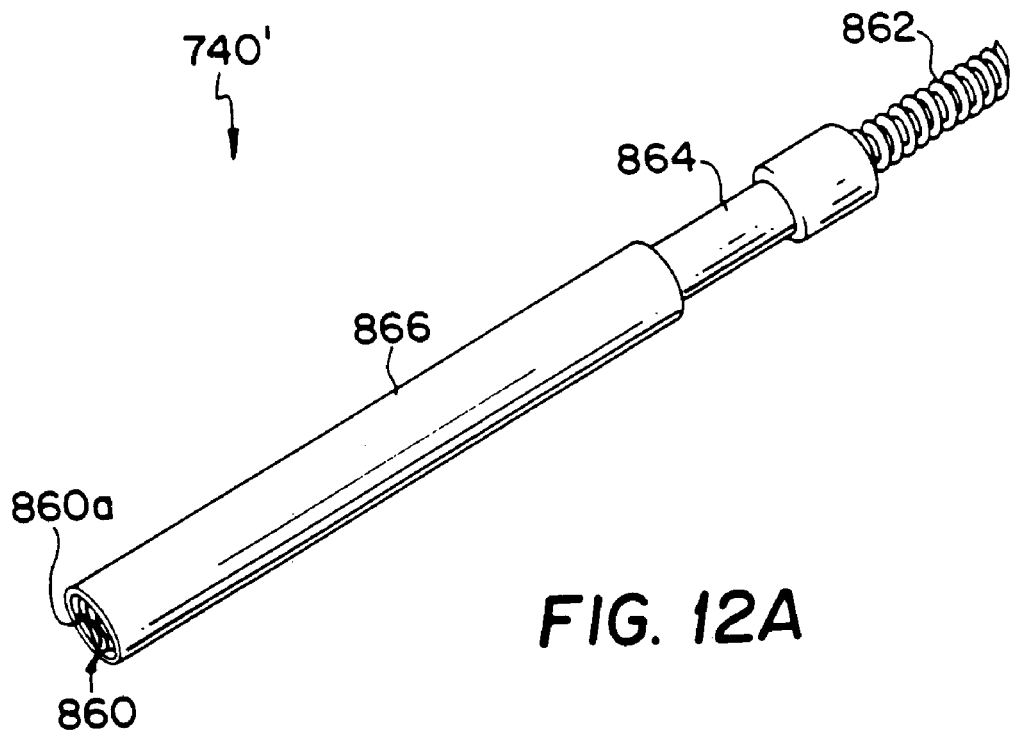
FIG. 12A is an isometric view of a tissue engaging member.

Referring to FIG. 12A, in an alternative embodiment, a third tissue engagement member 740' includes a tissue-engaging coil 860 with a tissue piercing end 860a, a helical drive shaft 862, and a coupling member 864 for translating a torque applied by drive shaft 862 to coil 860. Helical drive shaft 862 is preferably wound in a direction opposite that of tissue engaging coil 860, for reasons described below. Positioned over and axially movable relative to coupling member 864 is a sprung sheath 866. Tissue engagement member 740' can be used alone or can replace tissue engagement member 740 of FIG. 1. Coil 860 has, e.g., six loops with a pitch of 1½ mm from loop-to-loop and a diameter of 2 mm. Other configurations can be used, e.g., one loop and greater with the number of loops times the pitch corresponding to the desired penetration depth into the tissue.

Figure 12B:
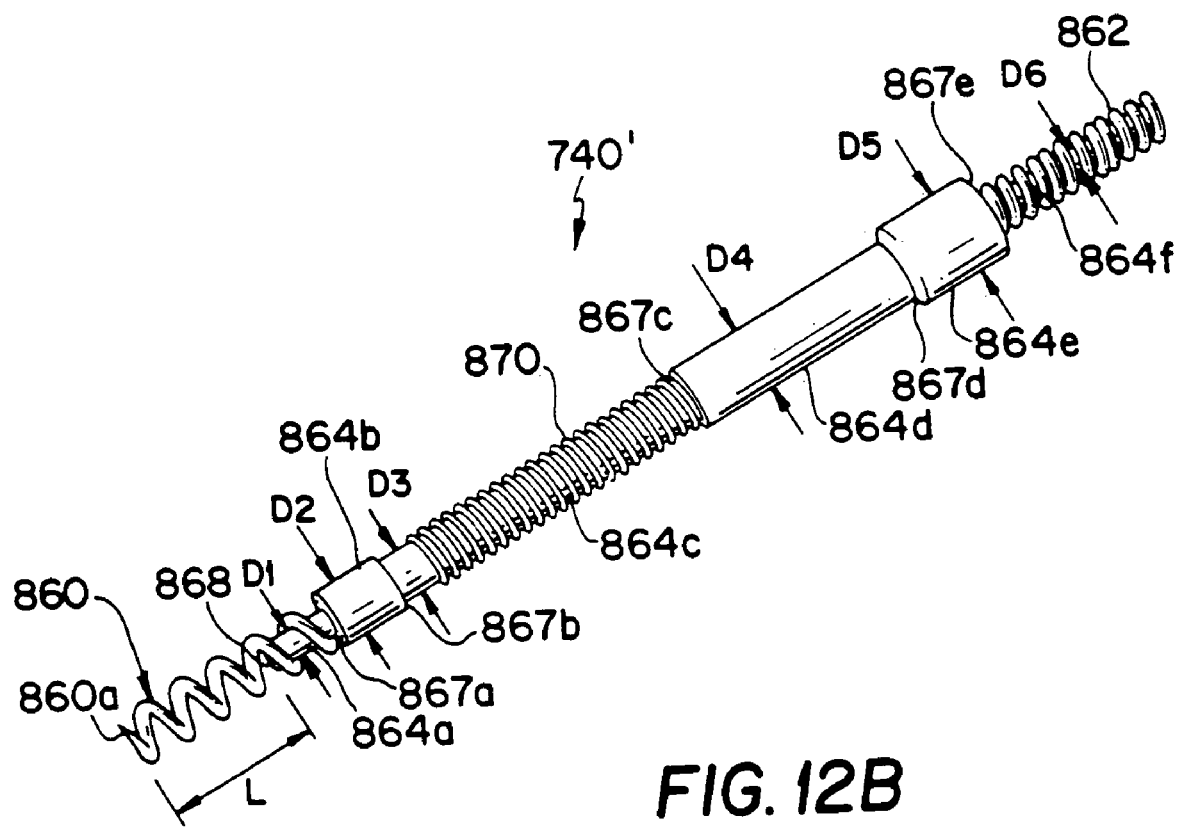
FIG. 12B is an isometric view of the tissue engaging member of FIG. 12A shown with an outer sheath removed.

Referring to FIG. 12B, in which tissue engagement member 740' is shown without spring sheath 866, coupling member 864 includes a first, distal-most section 864a with a diameter, D1; a second section 864b with a diameter D2 larger than D1; a third section 864c with a diameter D3 between D1 and D2; a fourth section 864d with a diameter D4 about equal to D2; a fifth section 864e with a diameter D5 larger than D4; and a proximal-most section 864f having a diameter D6 about equal to D1. Diameters D1-D1 are, for example, about 0.04", 0.09", 0.06", 0.09", 0.12" and 0.04", respectively. Defined between sections 864a and 864b is a shelf 867a; defined between sections 864b and 864c is a shelf 867b; defined between sections 864c and 864d is a shelf 867c; defined between sections 864d and 864e is a shelf 867d; and defined between sections 864e and 864f is a shelf 867e. Drive shaft 862 is received over coupling member section 864f and coil 860 is received over coupling member section 864a. Drive shaft 862 and coil 869 are attached to coupling member 864 by, for example, soldering. Coil 860 has a coil length, L, of, for example, about 0.25", extending beyond the distal end 868 of section 864a. Positioned on coupling member section 864c between shelves 867b and 867c is a spring 870 that biases sprung sheath 866 distally.

Referring to FIG. 12C, sprung sheath 866 defines a lumen 872 and has a first section 866a with an inner diameter d1, a second hub section 866b with an inner diameter d2 less than d1, and a third section 866c with an inner diameter d3 about equal to d1. Coil 860 is received within lumen 872 in sheath section 866a. Spring 870 is located within lumen 872 radially between coupling member section 864c and section 866c of sheath 866 and axially between hub 866b and shelf 867c. Sheath hub 866b is biased against shelf 867b by spring 870. The spacing between coupling member shelf 867d and a proximal end 874b of sheath 866 permits axial, proximal movement of sheath 866 against the action of spring 870.

To facilitate assembly of tissue engaging member 740', coupling member 864 is formed from two parts 876a, 876b having mating fingers 878 joined, for example, by compression fitting. This configuration permits sheath 866 to be slid over part 876a prior to joining part 876b to 876a.

Referring also to FIG. 12D, in operation, the user places distal end 874a of sheath 866 against tissue T to be pierced to stabilize the tissue. The user then applies distal and rotational forces to drive shaft 862, which causes coupling member 864 and coil 860 to move distally and rotate into the tissue, for example, the mucosal layer of tissue. As coil 860 advances into the tissue, distal end 874a of sheath 866 remains on the surface of the tissue, spring 870 is compressed, and shelf 867d advances toward sheath proximal end 874b. When coil 860 has been anchored in the tissue, for example, the muscle layer of tissue underlying the mucosal layer (which takes about 3 or 4 turns of the coil into the tissue), the user can manipulate the tissue with tissue engaging member 740'. By engaging multiple layers of tissue, member 740' provides a secure grasp on the tissue.

Sprung sheath 866 acts to stabilize both the tissue and coil 860 when coil 860 is advanced into the tissue. Sheath 866 compresses the tissue, facilitating initial penetration of the coil into the tissue, and helps keep the tissue from twisting as the coil rotates. Furthermore, the coil 860 tends to want to go off-axis as it rotates into the tissue. Sprung is sheath 866 provides enough force against the tissue and has enough friction against the tissue surface to limit movement of sheath 866 as coil 860 is advanced into the tissue. This counteracts the tendency of the coil to want to go off-axis.

Due to the opposed winding of drive shaft 862 and coil 860, the rotational force applied to drive shaft 862 causes a decrease in the diameter of drive shaft 862 upon encountering torsional resistance. This decrease in the diameter of drive shaft 862 limits contact of drive shaft 862 with the wall of an associated working channel in which drive shaft 862 is located and thus possible jamming in the working channel.

Referring to FIGS. 13A and 13B, to apply the distally and rotationally directed forces to drive shaft 862, a torque generator 882 held by the user and a drive rod 880 releasably attached to torque generator 882 and extending through handle 743 are coupled to drive shaft 862. Drive rod 880 runs a majority of the length of instrument 700 to provide high torque, with drive shaft 862 extending in the area of the retroflex region to provide high flexibility. Drive rod 880 and drive shaft 862 are coupled, e.g., by soldering. Torque generator 882 includes a handle 883, a collet 885, and a spring loaded cap 887. Collet 885 includes a circumferential section 885' and four legs 885a extending from section 885', each with an enlarged end 885b. Each leg 885a has a flat, inner facing surface 885c that together define a square opening 886. Drive rod 880 has a coupling member 889 with four flat sides 889a. Coupling member 889 is received within opening 886 with flat sides 889a aligned with surfaces 885c such that when closed, torque generator 882 and drive rod 880 are rotationally locked.

Handle 883 defines a bore 881' in which a pin 882' is received, and a larger diameter bore 883' in which pin 882', collet 885 and a spring 887' are received. Cap 887 is biased distally by spring 887'. Pin 882' is press fit into bore 881' and into circumferential section 885' of collet 885. To attach drive rod 880 to torque generator 882, cap 887 is moved proximally against the force of spring 887', which allows legs 885a to be flexed outward permitting coupling member 889 to be positioned in opening 886. The user releases cap 887, and spring 887' acts to move cap 887 distally closing legs 885a around coupling member 889. Distal motion of cap 887 is limited by contact of a shelf 880' of cap 887 against enlarged leg ends 885b.

Tissue engaging member 740' is preferably a single use disposable product supplied sterile to the user. Member 740' can be loaded into the instrument from the distal end of the instrument and then attached to torque generator 882. This preserves the sterility of the distal end of member 740'.

Referring to FIG. 14A, in an alternative embodiment, rather than stabilizing tissue with sprung sheath 866 of FIG. 12A, positioned within coil 860 is a solid needle 881a. Needle 881a extends from coupling member 864. Needle 881a facilitates the initial engagement of coil 860 with the tissue, and is particularly applicable to situations in which coil 860 approaches the tissue surface at an angle. Referring to FIGS. 14B and 14C, rather than a solid needle, positioned within coil 860 and extending to the proximal end of the tissue engagement member is a matter injector needle 881b, which can be advanced through coil 860. Matter injector needle 881b has a metal tip 881c on a flexible, plastic tube 881d. Coupling member 864, coupling member 889, pin 882', and hand grip 883 define aligned through bores that slidably receive needle 881b. Needle 881b replaces drive rod 880, and drive shaft 862 extends the length of the instrument.

Matter injector needle 881b can be used in "bulking" procedures to augment tissue in a selected region by injecting a biocompatible material, such as described, e.g., in U.S. Pat. No. 5,336,263 to Ersek et al., hereby incorporated by reference in its entirety. In use, coil 860 acts to anchor needle 881*b* in the tissue to counteract pressure created by the material injection, which would tend to push needle 881*b* out of the tissue. For matter injection, the tissue engaging instrument can be used through a working channel of an endoscope, or in conjunction with instrument 700. Alternatively, the wire forming coil 860 can define a lumen and matter injected through the wire lumen.

Figure 15A:
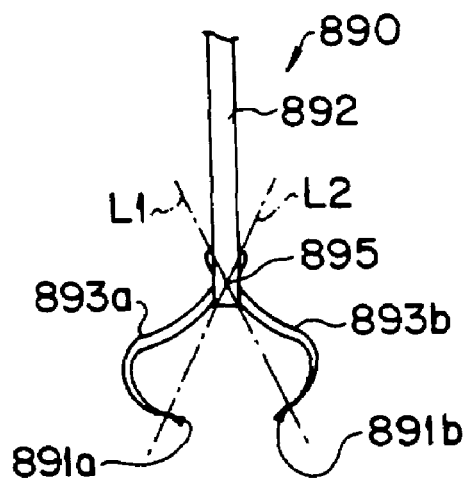
FIGS. 15A-15D are illustrations of an additional alternative tissue engaging member.
Figure 15B:
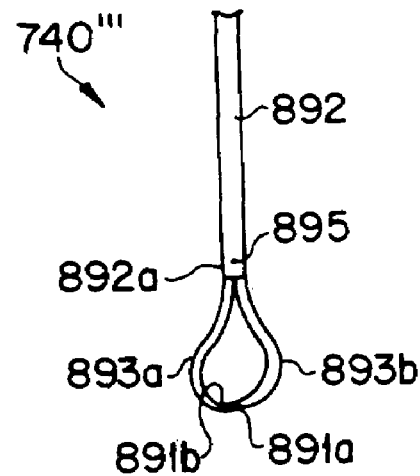

Referring to FIGS. 15A and 15B, an alternative third tissue engagement member 740''' includes an elongate member 892 that passes through a working channel of instrument 700 and a pair of pincers 893*a* and 893*b* pivotably mounted at a pivot 895 to the distal end 892*a* of elongate member 892. Pincers 893*a* and 893*b* each include a respective pincer tip 891*a* and 891*b* suitable for piercing tissue. Pincers 893*a* and 893*b* are actuated, e.g., by one or more guidewires (not shown), as is described, e.g., in U.S. Pat. No. 5,613,499 to Palmer et al., hereby incorporated by reference in its entirety.

Pincers 893*a* and 893*b* are generally arcuate in shape with pincer tips 891*a* and 891*b* oriented substantially normal to lines L1, L2 defined by pivot point 895 and the end of each respective pincer tip. Pincers 893*a* and 893*b* are made from a rigid, sterilizable material capable of maintaining pincer tips 891*a* and 891*b* suitable for puncturing tissue and withstanding at least short term exposure to operating environments such as the stomach. As such, pincers 893*a* and 893*b* can be made from metals such as stainless steel and Co—Cr alloys.

Figure 15C:
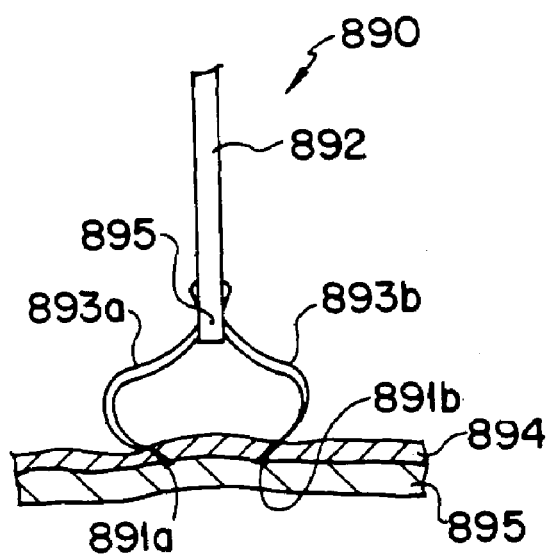
Figure 15D:
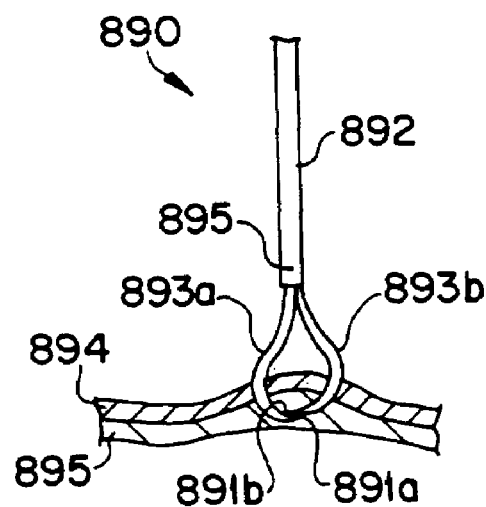

Referring to FIGS. 15C and 15D, in operation, with pincers 893*a* and 893*b* in their opened position, the user advances tissue engagement member 740''' into contact with a tissue surface such as a mucosal layer 894 on a muscle layer 895 in the stomach. The user then closes pincers 893*a* and 893*b* such that the pincer tips 891*a* and 891*b* penetrate through the mucosal layer 894 and into muscle layer 895. Once the pincer tips 891*a* and 891*b* have been drawn together, the user retracts the pincers 893*a* and 893*b* from the engaged tissue using the elongate member 892. Plication and/or bulking of the retracted tissue can follow as described elsewhere herein.

Due to the arcuate shape of pincers 893*a* and 893*b*, the initial closing of the pincers results in substantially distal translation of pincer tips 891*a*, 891*b*, with further closing of the pincers resulting in substantially transverse motion of pincer tips 891*a*, 891*b*. This distributes the retraction load applied by the pincers 893*a* and 893*b* for plication over a relatively large area of tissue, limiting the possibility of tearing the tissue during retraction.

Figure 16A:
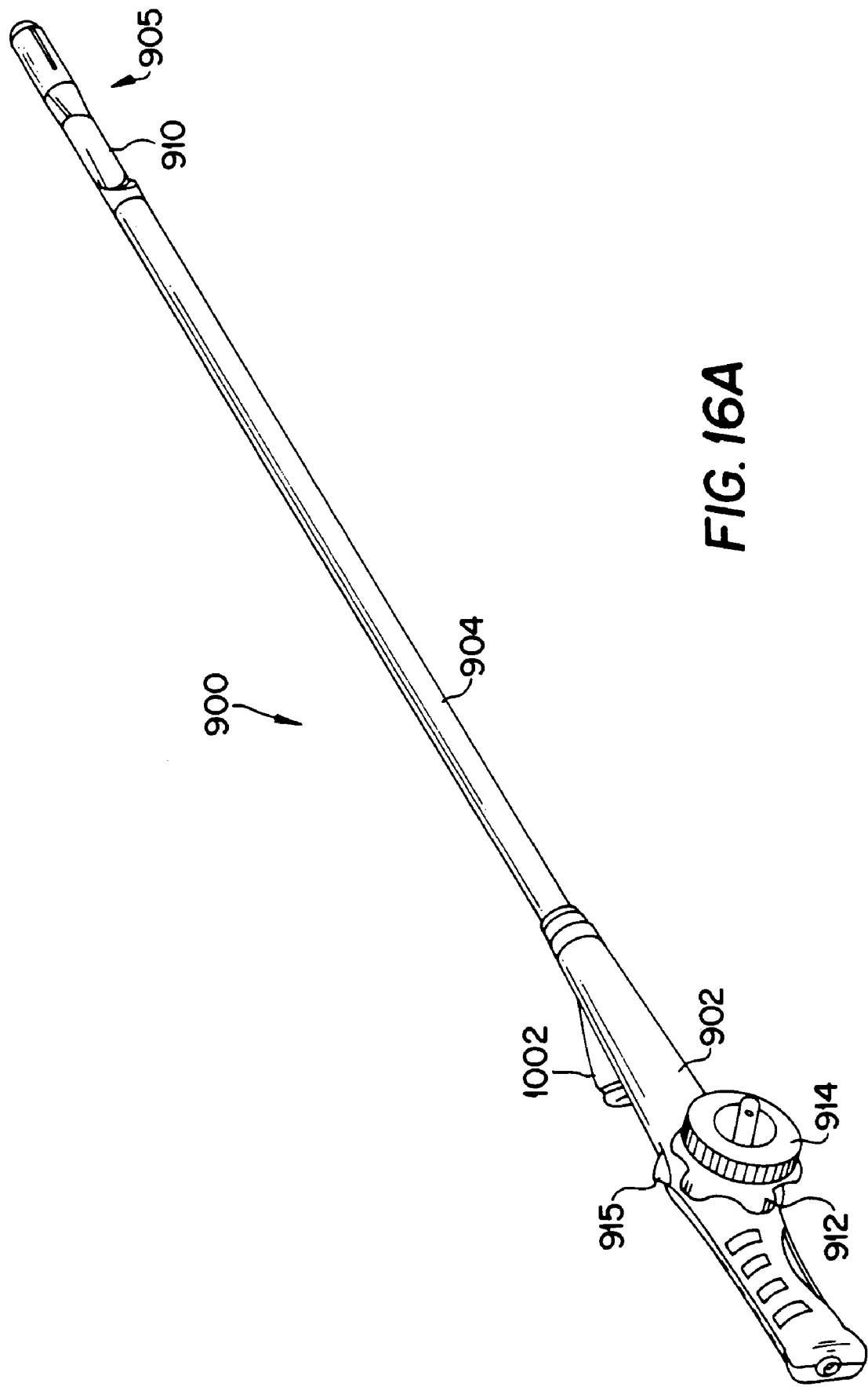
FIG. 16A is an isometric view of an instrument for reconfiguring tissue.
Figure 16B:
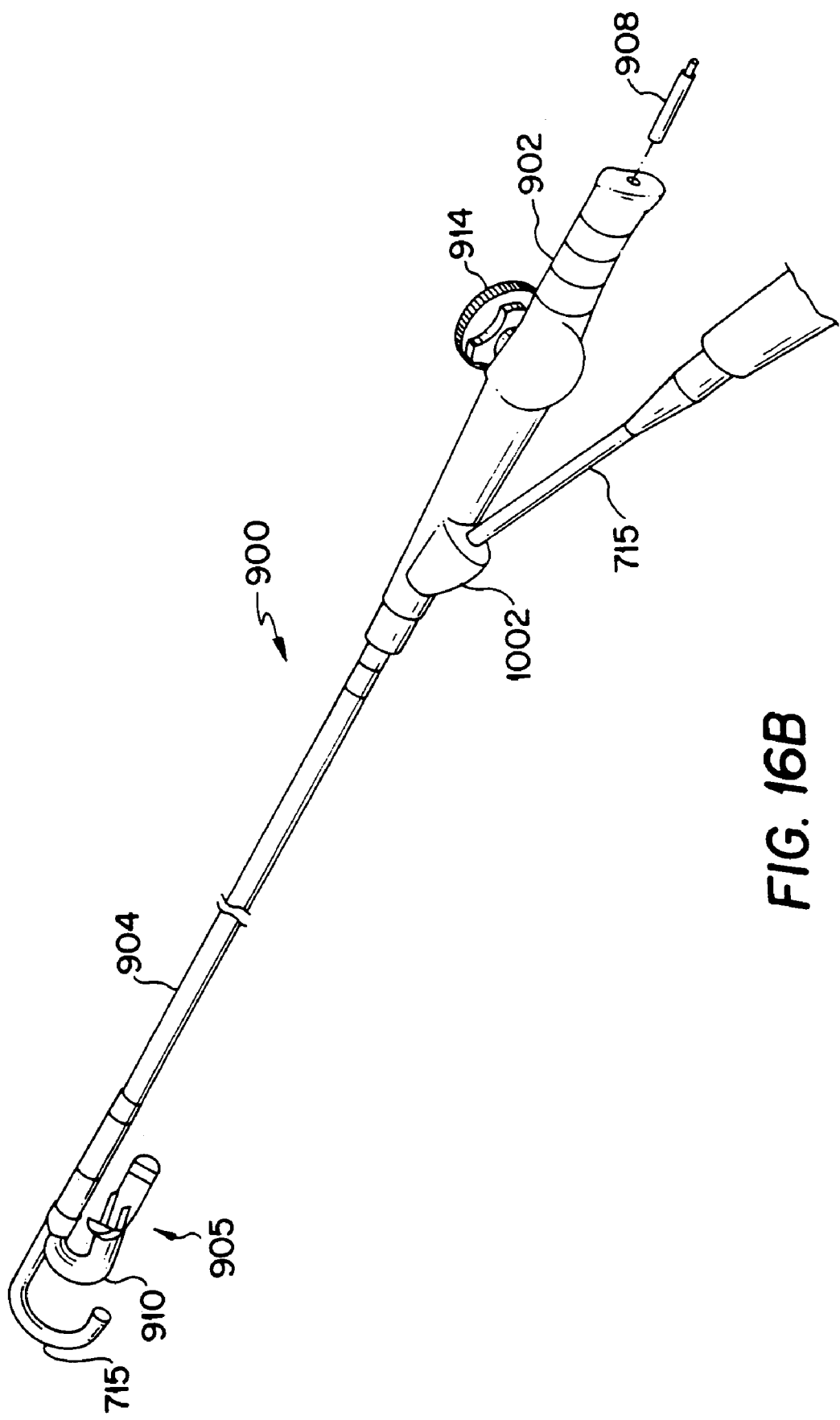
FIG. 16B shown the instrument of FIG. 16A receiving a gastroscope.

Referring to FIGS. 16A and 16B, in accordance with another embodiment of the invention, an instrument 900 for reconfiguring stomach tissue includes a handle 902, an elongated instrument shaft 904, and a distal actuating assembly 905. As discussed below, the configuration of assembly 905, and the means of attachment of assembly 905 to instrument shaft 904, substantially seals a lumen of shaft 904 that houses the actuating cables from contact with bodily fluids. As a result, only a disposable portion of assembly 905 need be supplied to the user in a sterile condition. The remainder of the instrument can simply be disinfected by manual cleaning and soaking in a disinfecting solution between procedures.

As in embodiments discussed above, instrument 900 receives gastroscope 715 and a tissue engagement member 908 (such as coil 740 or 740' described above). Assembly 905 includes a retroflex portion 910 that is manipulated by the user to orient assembly 905 (as shown in FIG. 16B). Handle 902 includes control knobs 912, 914 that actuate assembly 905, and a switch 915 that disengages a lock mechanism, as described below.

Referring to FIGS. 17A and 17B, shaft 904 defines a lumen 916 through which the end of gastroscope 715 protrudes. Retroflex portion 910 has a sloping curved wall section 918 against which the end of gastroscope 715 is received. When flexed, retroflex portion 910 is bent in a direction away from section 918 (arrow A). Assembly 905 further includes a coupling member 919 and an end effector 906. Coupling member 919 includes a first portion 923 that attaches to retroflex portion 910, and a mount 924 to which end effector 906 is pivotally mounted. End effector 906 includes jaw members 920, 922, each of which includes a tissue manipulating cartridge 960*a*, 960*b*, respectively, releasably mounted to a respective actuating arm 962*a*, 962*b*.

Covering retroflex portion 910 and coupling member portion 923 is a cover 910', and covering mount 924 and end effector 906 is a hood 1220, discussed further below. Hood 1220 provides an atraumatic distal end for transoral placement of instrument 900, and cover 910' seals retroflex portion 910 and coupling member portion 923 from contact with bodily fluids.

In use, with gastroscope 715 in instrument lumen 916 and the end of the gastroscope residing in section 918, the user advances instrument 900 transorally into the stomach. Once in the stomach, gastroscope 715 is independently manipulated to obtain the desired view. The user flexes instrument 900 (as shown in FIG. 16B), opens jaws 920, 922, advances the tissue engagement member into engagement with the tissue to stabilize the tissue, closes jaws 920, 922 such that cartridges 960*a*, 960*b* manipulate the tissue into a bulge, and deploys an implant, as described further below.

Figure 17C:
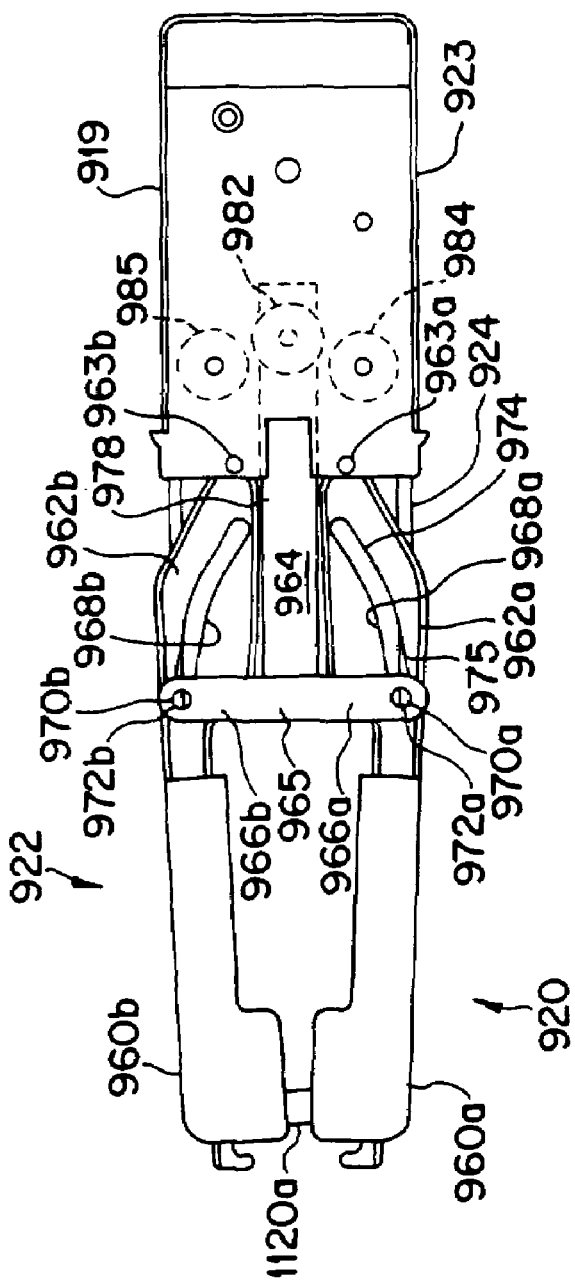

Referring to FIG. 17C (coupling member 919 has been partially removed from FIG. 17C for clarity), actuating arms 962*a*, 962*b* are pivotally coupled to mount 924 at pivots 963*a*, 963*b*, respectively. A pair of cables, discussed below, for opening and closing jaws 920, 922 are coupled to the jaws via a yoke 964. Yoke 964 has a generally H-shaped section 965 with two legs 966*a* straddling arm 962*a*, and two legs 966*b* straddling arm 962*b*. Each arm 962*a*, 962*b* defines a slot 968*a*, 968*b*, and each leg 966*a*, 966*b* defines a through hole 970*a*, 970*b*. Received within slot 968*a* and holes 970*a* is a pin 972*a*, and received within slot 968*b* and holes 970*b* is a pin 972*b*. Slots 968*a*, 968*b* each have first and second sections 974, 975. Slot sections 974 are orientated at a greater angle relative to the axis of the instrument than that of slot sections 975, for purposes described below. Yoke 964 includes a post 978 extending proximally from section 965. Post 978 extends into coupling member 980. Mounted to post 978 is a first pulley 982, and mounted to coupling member 980 are two pulleys 984, 985, which a jaw closing cable is routed over, as described below.

Figure 17D:
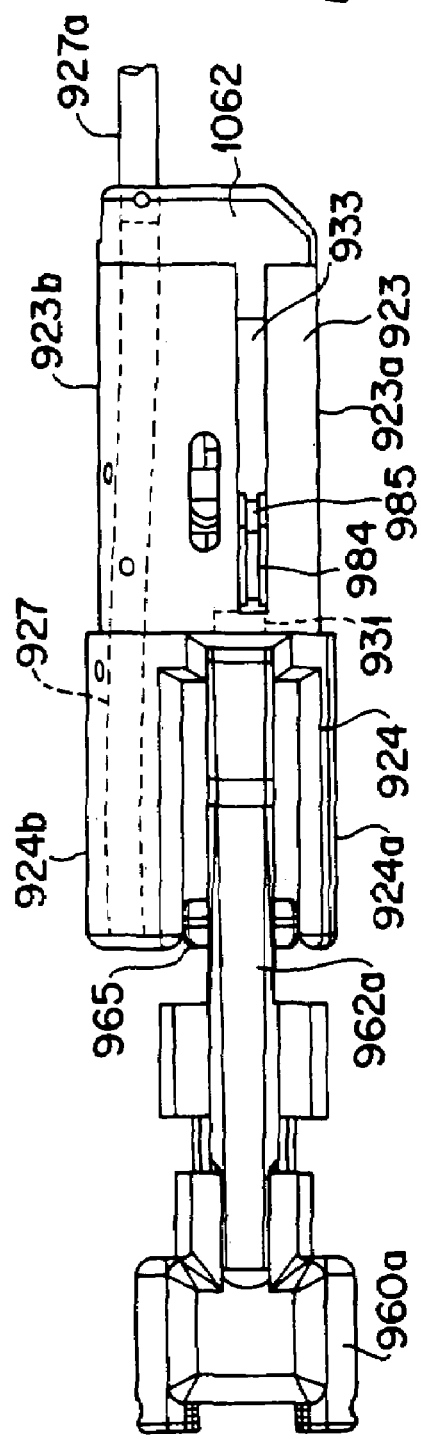

Portion 923 and mount 924 of coupling member 919 have flat sides 923*a*, 924*a* and rounded sides 923*b*, 924*b*, as shown in FIG. 17D. Rounded sides 923*b*, 924*b* define a through bore 927 for passage of the tissue engagement member. Mount 923 also defines a through bore 931 through which yoke 964 extends.

Referring to FIGS. 17E and 17F, located in portion 923 is a lock arm 1250 pivotally mounted at 1252. Lock arm 1250 has a ridge 1253 with curved wall 1254 and yoke 964 defines a notch 1256 with a correspondingly shaped curved wall 1258. After a predetermined amount of distal travel of yoke 964, curved wall 1254 of ridge 1253 engages with curved wall 1258 of notch 1256 to limit further distal travel of yoke 964. Lock arm 1250 is biased by a compression spring 1262 to rotate clockwise about pivot 1252 (arrow Y) such that when notch 1256 passes under lock arm 1250, lock arm 1250 is rotated under the force of spring 1262 to engage curved walls 1254, 1258. Attached to lock arm 1250 is a cable 1260 for moving arm 1260 out of engagement with yoke 964 to allow further distal travel of yoke 964.

FIG. 17G illustrates the replaceable nature of cartridges 960a, 960b. Arms 962a, 962b each include a flat, rectangular member 1050 and a clip 1052. Member 1050 has formations 1051, 1053 extending from either side of member 1050. Formations 1051 have a thin distal section 1051a that slopes to a wider proximal section 1051b, for purposes described below with reference to FIGS. 46. Cartridges 960a, 960b each include a first pair of side walls 1054, a second pair of side walls 1056 defining slots 1056a, an opening 1058, and a head 1059. Opening 1058 is rectangular in shape, here shown square, though other shapes are suitable that have a mating contour with a flat proximal edge 1058a. Instead of an opening 1058, an indentation in the cartridge that corresponds to the shape of clip 1052 can be employed. Side walls 1054, 1056 are separated by a thin section 1057 which allows the cartridge to flex.

To attach cartridges 960a, 960b to arms 962a, 962b, respectively, the cartridge is slid over the arm with side walls 1054 aligning the cartridge to the arm. Rectangular member 1050 is received in slots 1056a while the cartridge flexes over clip 1052 such that clip 1052 is received within opening 1058 to lock the cartridge to the arm. To remove the cartridge, the user pushes on side walls 1054 to flex the cartridge away from clip 1052, and the cartridge is then slid off the arm.

Referring to the exploded view of FIG. 17H, retroflex portion 910 has a proximal mount 1060 that is, e.g., glued onto the end of shaft 904, and a distal mount 1062 that is received within a slot 933 in mount 923. Mounts 1062, 923 are attached, e.g., by screws. Mount 1062 is preferably metal and coupling member 919 is preferably plastic.

Referring to FIG. 17I, the only member of instrument 900 that extends from retroflex region 910 through the sealed section formed by cover 910' is yoke 964. To limit access of bodily fluids to retroflex portion 910, coupling member portion 923 defines a space 1070 in which an o-ring 1072 is positioned to seal off through bore 931.

Figure 20:
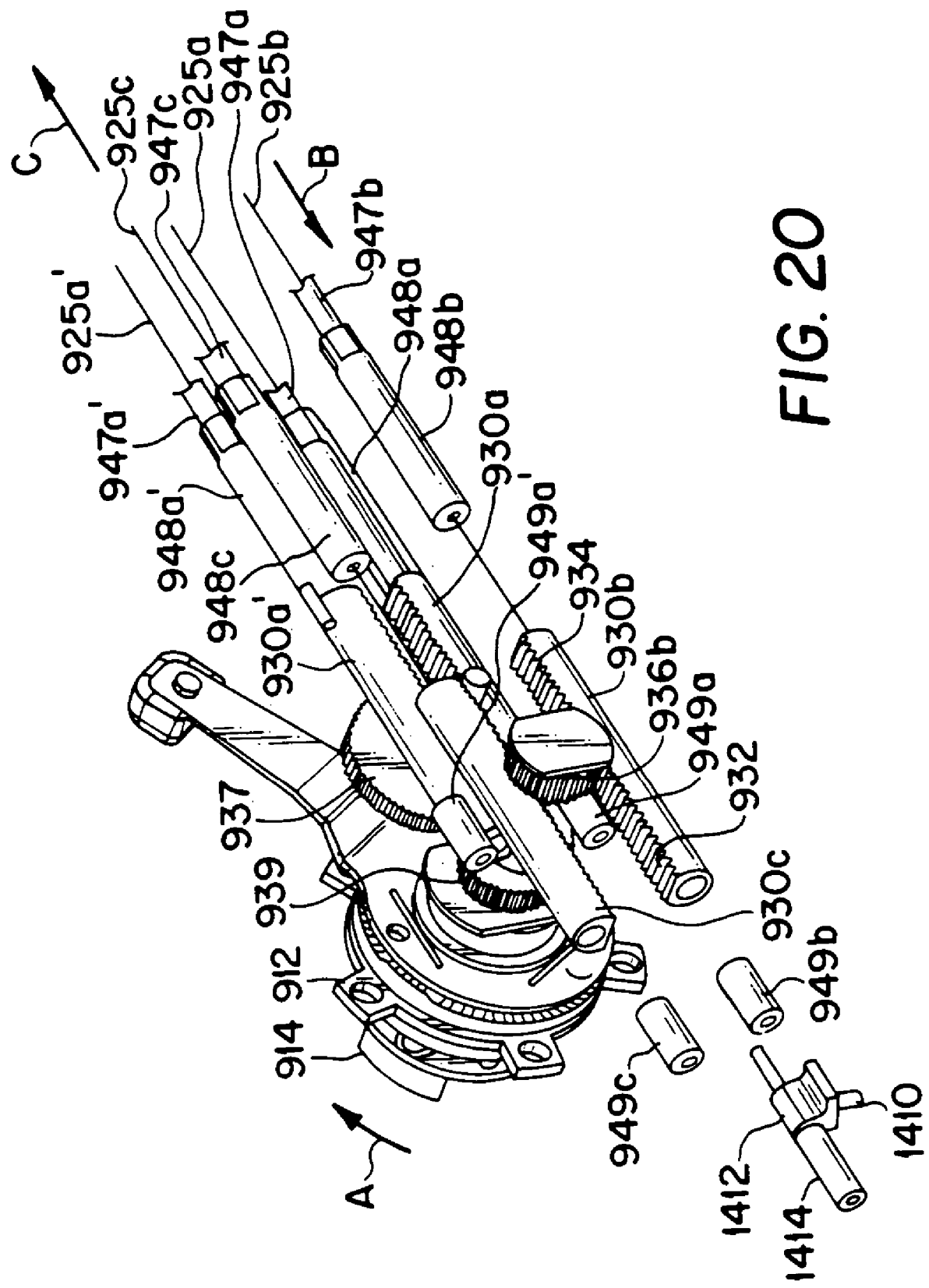
FIG. 20 is an illustration of the mechanism inside the gearbox of FIG. 19.
Figure 21A:
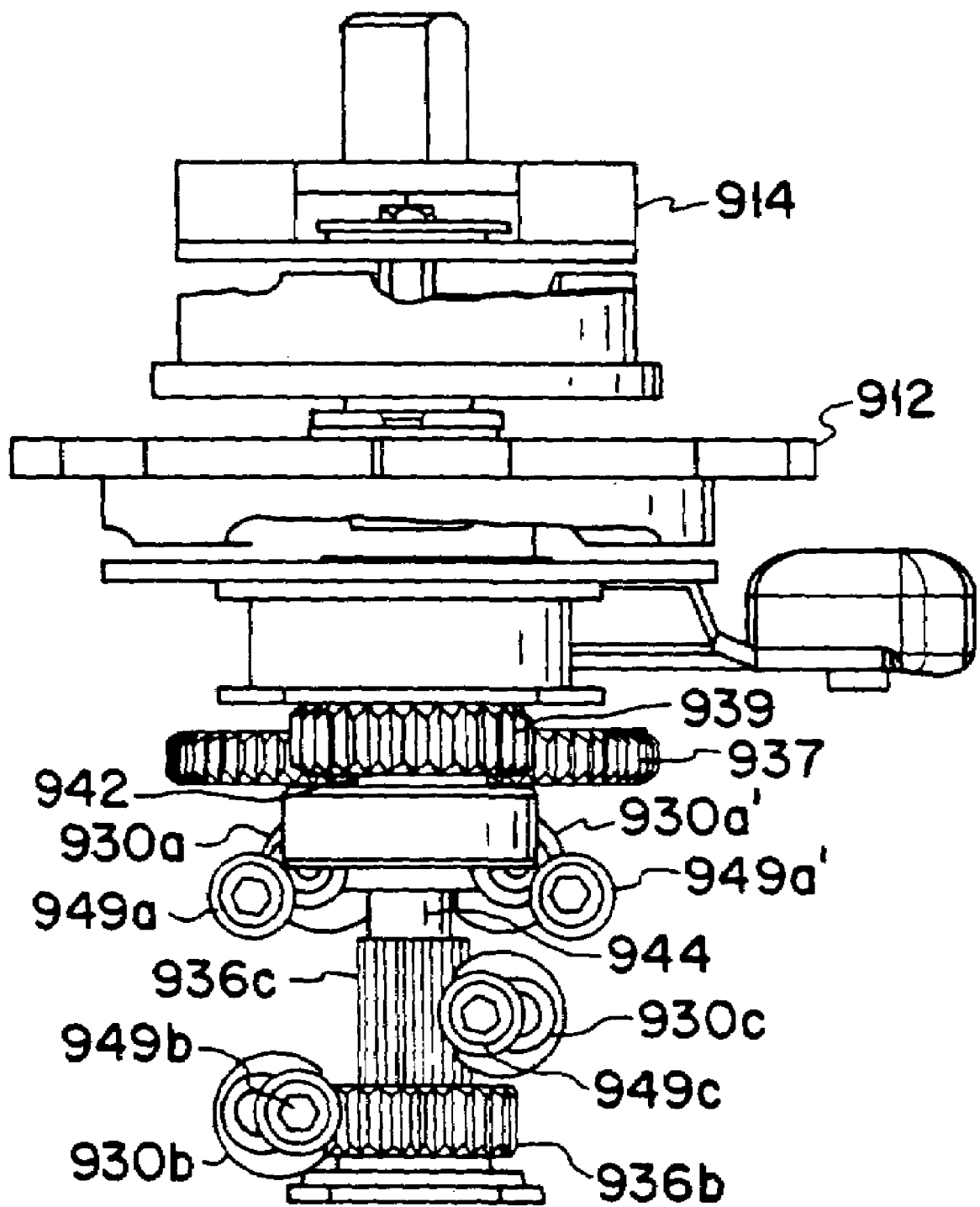

Referring to FIGS. 18-20, to control retroflex portion 910 and end effector 906, knobs 912, 914 interface with a series of cables 925a, 925a', 925b, 925c (FIG. 20) through a gear block mount 926 located in handle 902. Block mount 926 defines through bores 928a, 928a', 928b, 928c within each of which a rack 930a, 930a', 930b, 930c, respectively, is located. Each rack 930a, 930a', 930b, 930c is connected to a respective cable 925a, 925a', 925b, 925c, as described below, and has a flat side 932 defining teeth 934. Referring particularly to FIGS. 21A and 21B, associated with racks 930a, 930a' is a pinion 936a, and associated with each rack 930b, 930c is a respective pinion 936b, 936c. Racks 930a, 930a' are on opposite sides of pinion 936a, and racks 930b, 930c are on opposite sides of pinions 936b, 936c. Pinion 936c is preferably twice the diameter of pinion 936b, for reasons discussed below. Pinion 936a is driven by a reduction gear set 937, 939. Gear 939 is mounted to a shaft 942 that is integral with retroflex knob 912. Pinions 936b, 936c are mounted to a shaft 944 that is integral with jaw actuating knob 914, and passes through shaft 942.

To manipulate retroflex portion 910, the user turns knob 912, which causes shaft 942 and pinion 936a to turn. Since racks 930a, 930a' are on opposite sides of shaft 946, rotation of pinion 936a causes opposed linear motion of racks 930a, 930a', which moves cables 925a, 925a' to flex and straighten retroflex portion 910, as described further below. To manipulate the jaws, the user turns knob 914, which causes shaft 946 and pinions 936b, 936c to rotate. Since racks 930b, 930c are on opposite sides of shaft 946, rotation of pinions 936b, 936c causes opposed linear motion of racks 930b, 930c, which moves cables 925b, 925c to open and close the jaws, as described further below. Associated with knob 912 is a tension adjustment knob 912a, and associated with knot 914 is a tension adjustment lever 914a, as is well known in the art.

Referring to FIGS. 20 and 22, mounted over each cable 925a, 925a', 925b, 925c is a cable housing 947a, 947a', 947b, 947c, respectively, and a cable housing adjustment screw 948a, 948a', 948b, 948c, respectively. Cable housing adjustment screws 948a, 948a', 948b, 948c are threadably received within respective block through bores 928a, 928a', 928b, 928c (as shown in FIG. 19). Rotation of screws 948a, 948a', 948b, 948c translates cable housings 947a, 947a', 947b, 947c distally and proximally along respective cables 925a, 925a', 925b, 925c to provide an optimal working length for transmitting actuating forces. Cables 925a, 925a', 925b, 925c move freely through their respective housings and screws.

On the opposite side of racks 930a, 930a', 930b, 930c from screws 948a, 948a', 948b, 948c are stops 949a, 949a', 949b, 949c received within respective block through bores 928a, 928a', 928b, 928c. Stops 949a, 949a', 949b, 949c limit the travel of racks 930a, 930a', 930b, 930c, respectively.

Referring particularly to FIG. 22, cable 925a is received within a bore 950 defined in rack 930a. Cable 925a extends through a hole 952 defined in an end wall 954 of rack 930a into bore 950. Located within bore 950 is a spring 956. Cable 925a extends through spring 956 and has an enlarged terminal end 957 that maintains the position of cable 925a relative to spring 956. Spring 956 acts to continually exert a slight tensile force upon cable 925a to keep the cable taught. Cables 925b, 925c are likewise coupled to racks 930b, 930c, respectively.

Figure 23A:
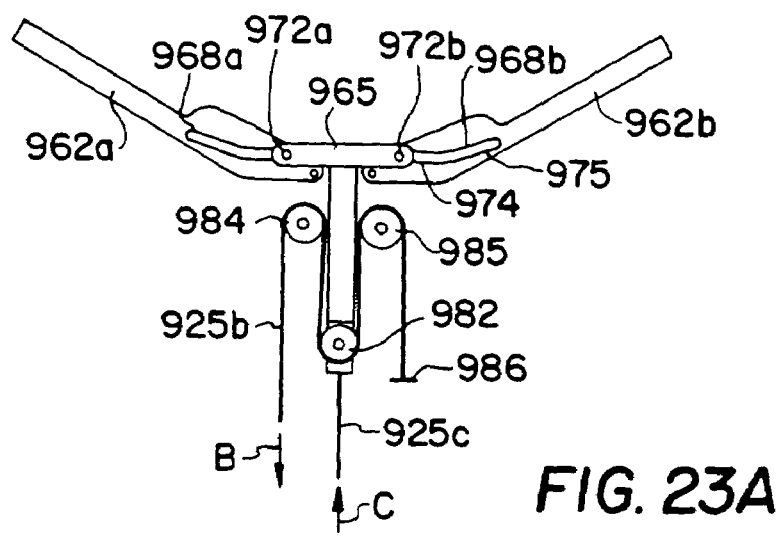
FIGS. 23A-23D illustrate the closing of jaw members of the end effector.

Referring again to FIG. 19, attached to block mount 926 is a slide lever 1400 mounted within a bracket 1402. Switch 915 is received within an opening 1404 in lever 1400 such that movement of switch 915 moves lever 1400. Lever end 1406 defines a diagonal slot 1408 in which a pin 1410 is received. Pin 1410 is attached to a stop member 1412 that contacts a stop 1414 after jaw closing rack 930b has traveled a pre-set distance. Movement of lever 1400 in the direction of arrow X causes pin 1410 and stop member 1412 to rotate about the axis of stop member 1412, disengaging stop member 1412 from stop 1414 to allow further movement of rack 930b. Cable 1260 attached to lock arm 1250 is attached at its opposite end to switch 915. When switch 915 is moved in the direction of arrow X, cable 1260 moves lock arm 1250 to disengage lock arm 1250 (FIG. 17E) from yoke 964 (discussed further below with reference to FIG. 23). Bracket 1402 can be adjusted to fine tune the positioning of switch 915 relative to pin 1410 and lock arm 1250.

As shown in FIGS. 23A-23D, jaw closing cable 925b is wound around pulleys 984 and 982, and terminates at a fixed point 986 connected to distal mount 1062 (FIG. 17G). Jaw opening cable 935c is connected in a fixed relationship to post 978. To close jaws 920, 922, the user turns knob 914 in the direction of arrow, A (FIG. 20), which moves cable 925b in the direction of arrow, B, and permits slack in cable 925c allowing yoke 965 to move distally, in the direction of arrow, C. Due to the 2:1 ratio between pinions 936b and 936c, cable 925b moves twice the distance of cable 925c. (This is required due to the routing of cable 925b around pulleys 982, 984.) Pins 972a, 972b slide along slots 968a, 968b causing jaws 920, 922 to close. To open the jaws, the user turns knob 914 in the direction opposite arrow, A, which tensions cable 925c and permits slack in cable 925b. The tension on cable 925c moves yoke 964 proximally, arrow, E, opening jaws 920, 922.

Figures 23B, 23C, 23D:
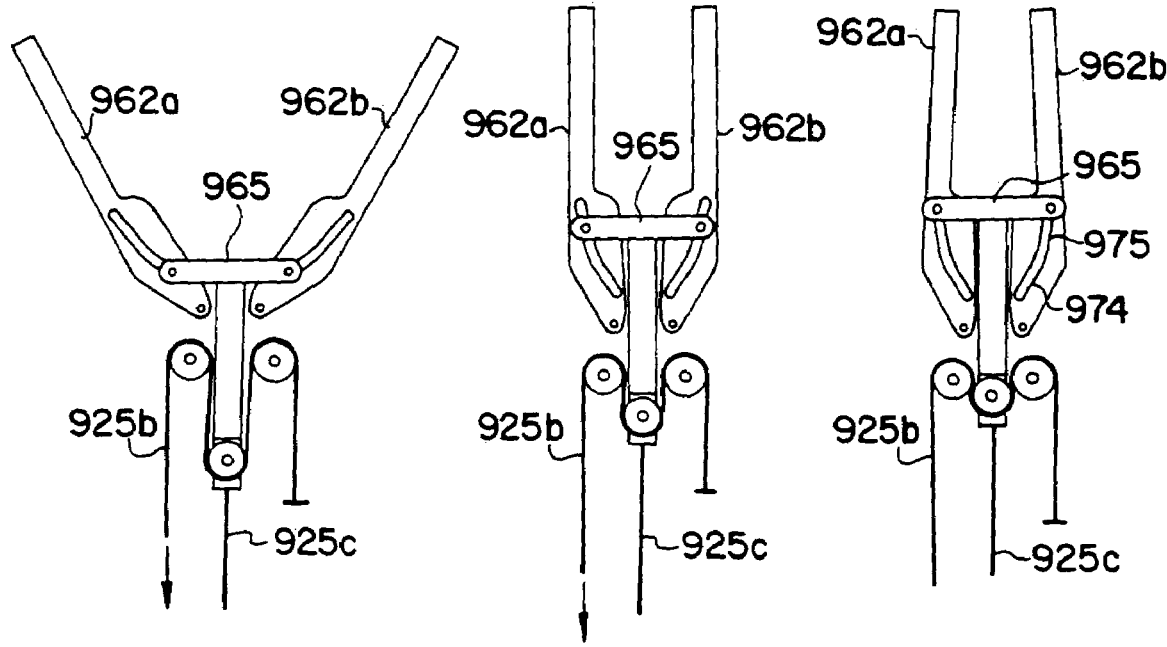
Figure 24A:
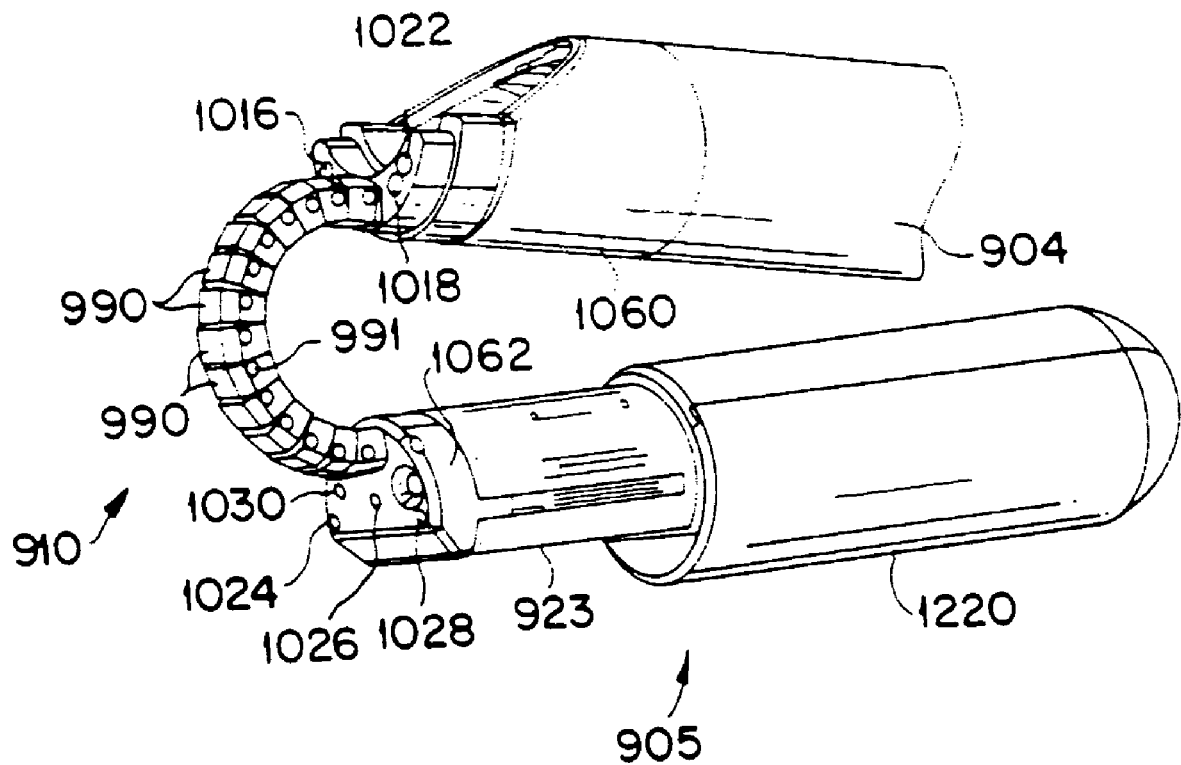
FIG. 24A is an illustration of the distal end portion in a flexed position.
Figure 24B:
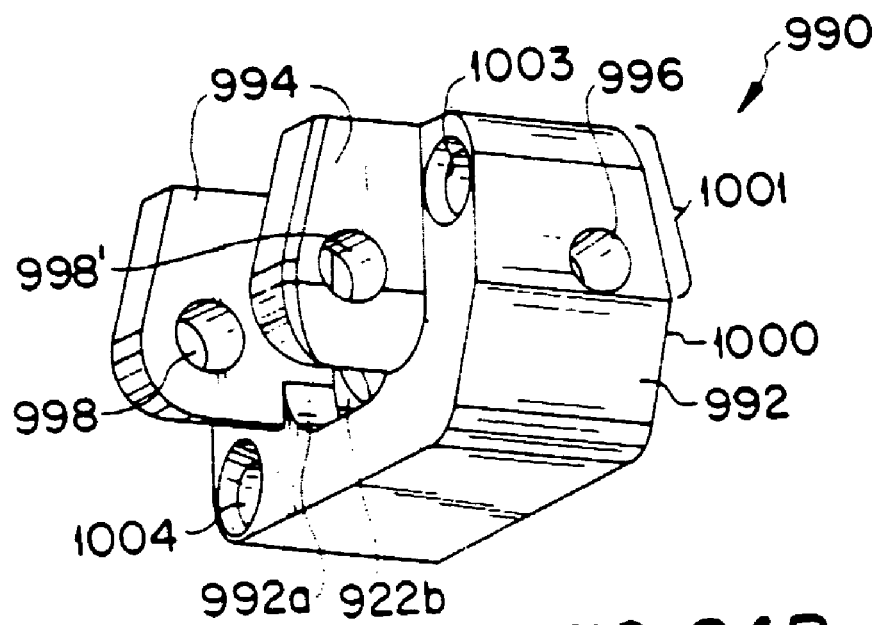
FIG. 24B is an isometric view of a link of a retroflex portion of the distal end portion.
Figure 24C:
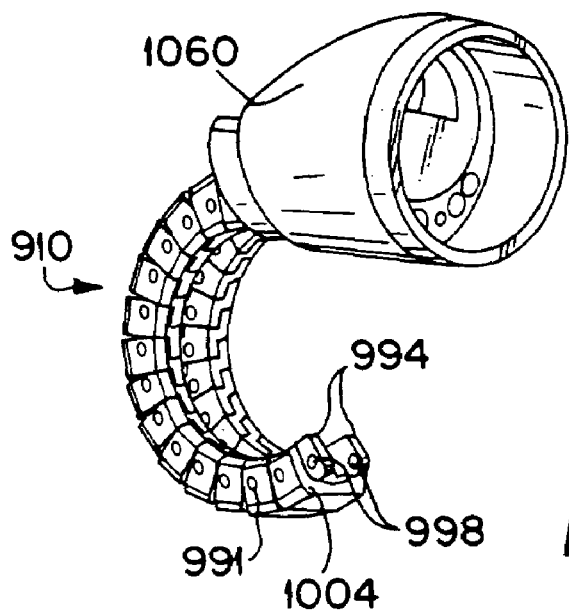
FIGS. 24C and 24D show the retroflex portion flexed and straight, respectively.
Figure 24D:
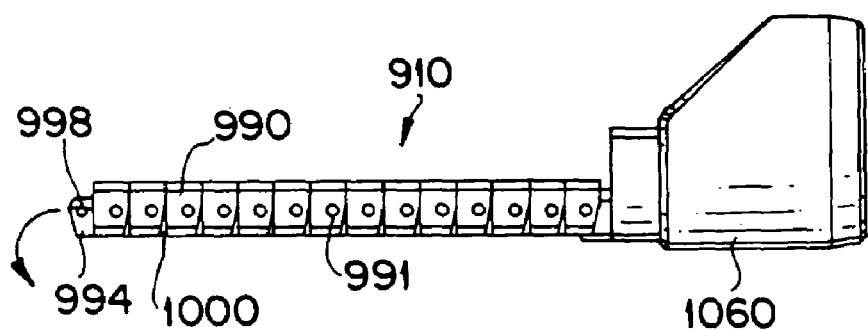

Due to the orientation of slot sections 974, 975, during the initial stage of jaw closing (FIG. 23B) when the yoke is sliding along slot section 974, there is a greater ratio of jaw closing for the distance the piston moves than during the later stage (FIG. 23C) when the yoke is sliding along slot section 975. There provides faster jaw closing with lower mechanical advantage when less closing force is needed (because the jaws are not yet contacting the tissue), and slower jaw closing with higher mechanical advantage when more closing force is needed as the jaws grasp the tissue and pierce through the tissue. After the jaws have reached the position of FIG. 23C, pin hits stop in handle and lock arm notch 1254 and yoke notch 1256 engage to limit further closing of the jaws. The user then pushes switch 915 proximally to move stop member out of the way and to disengage lock arm 1250 from yoke 964, this permits knob 914 to be further turned to completely close the jaws and deploy the implant (FIG. 23D).

Referring to FIGS. 24A-24D, retroflex portion 910 includes a series of links 990 that are hinged together with pins 991. Each link 990 includes a generally U-shaped body 992 with a first section 992a defining a U-shaped opening and second section 992b defining a larger U-shaped opening. Extending from body 992 are two mating prongs 994. Body 992 defines two transverse holes 996 (only one hole 996 being shown in FIG. 24B), and each prong 994 defines a transverse hole 998. When two links 990 are mated, prongs 994 lie within the U-shaped opening defined by section 992b. Holes 996, 998 are aligned, and pin 991 is passed through holes 996, 998 to join the two links. Body 992 has a side wall 1000 with a portion 1001 of the side wall set at an angle to allow the joined links to flex. Links 990 also define axial holes 1003, 1004 for receiving cables 924a, 924a'. Cables 924a, 924a' terminate on mount 1062. Pulling cable 924a flexes portion 910, and pulling cable 924a' straightens portion 910. Cover 910' (FIG. 17A) covers the links.

Figure 25:
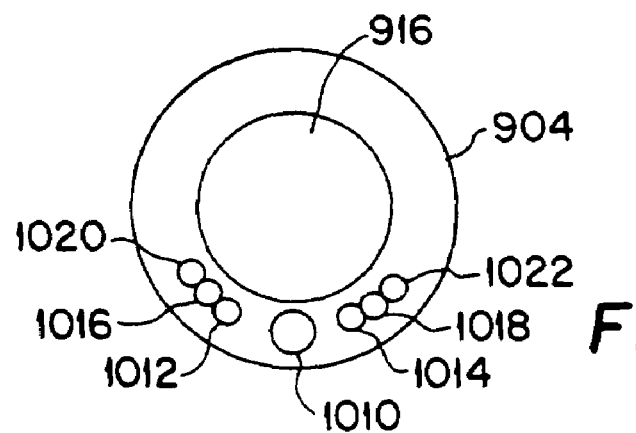
FIG. 25 is a cross-sectional view of a shaft of the instrument of FIG. 16A.

Referring also to FIG. 25, in addition to lumen 916 for receiving gastroscope 715, shaft 904 and mount 1060 define a lumen 1010 for receiving tissue engaging member 908, a lumen 1012 for receiving flexing cable 924a, a lumen 1014 for receiving straightening cable 924a', a lumen 1016 for receiving closing cable 925b, a lumen 1018 for receiving opening cable 925c, a lumen 1020 for receiving locking cable 1260, and an extra lumen 1022 if needed. Mount 1062 includes holes 1024 and 1026 for passage of cables 925b, 925c, respectively, a hole 1028 at which the end of closing cable 925b terminates, and a hole 1030 for passage of locking cable 1260.

Tissue engaging member 908 is located in the U-shaped openings defined by U-shaped bodies 992 in retroflex portion 910. Pins 991 are centered along the central axis of tissue engaging member 908 such that when flexed, tissue engaging member 908 is flexed along is central axis. Tissue engaging member 908 is surrounded by a sheath 927a (FIGS. 17D and 18). Sheath 927a runs from handle inlet 1002 to the proximal end of through bore 927 in coupling member 919. Sheath 927a is sealed at one end to handle 902 and at the other end to coupling member 919. This effectively seals the remainder of the instrument from contact with fluid that enters tissue engaging member 908. Shaft lumen 906 likewise is lined with a sheath 906' that seals the remainder of the instrument from contact with bodily fluids that enter lumen 906.

Figure 26:
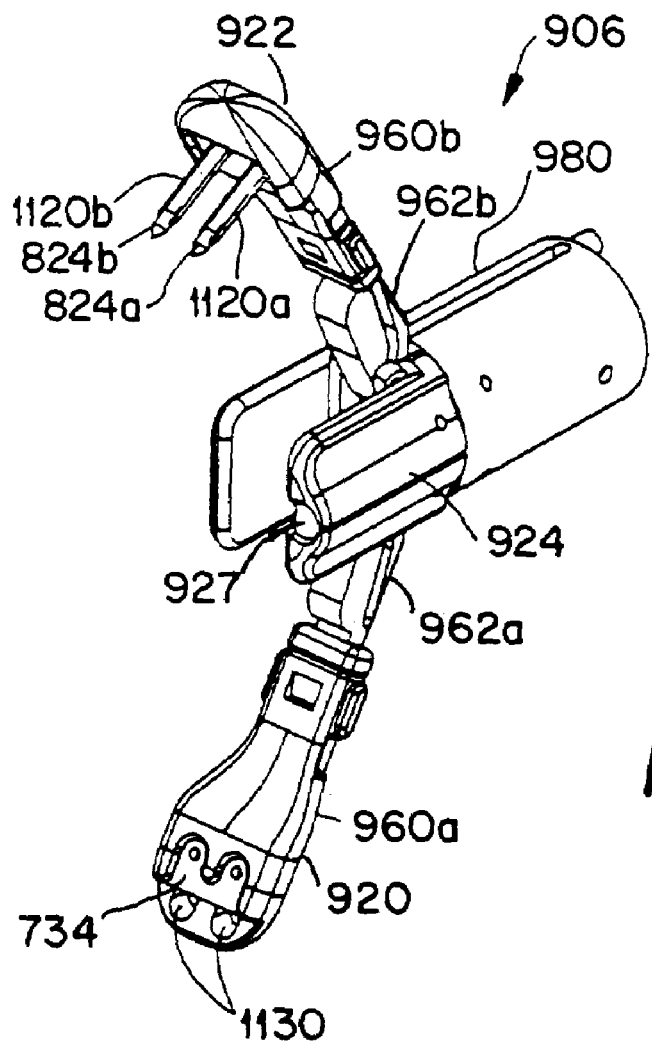
FIG. 26 is an isometric view of the distal end portion with the jaw members open.
Figure 27:
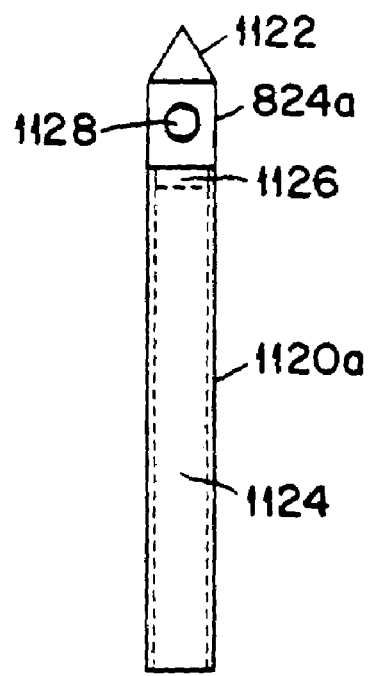
FIG. 27 is an illustration of an implant bar of a tissue fixation device shown coupled to a tube of the jaw member.

Referring to FIGS. 26 and 27, end effector 906 is configured for deployment of a tissue fixation member upon closing of jaws 920, 922 without requiring further actuation. Cartridge 960b of jaw 922 includes tissue passing tubes 1120a, 1120b. Removably coupled to each tube 1120a, 1120b is a tissue fixation bar 824a, 824b having a pointed tip 1122 for penetrating tissue. Each tube 1120a, 1120b defines a through bore 1124, and each bar 824a, 824b has a hub 1126 that fits within bore 1124. Tubes 1120a, 1120b and bars 824a, 824b have the same outer diameter for ease of penetrating tissue. Bars 824a, 824b each define a through hole 1128 for receiving, for example, a suture (not shown), which is passed through both holes and tied off to itself. Bars 824a, 824b can be coupled to tubes 1120a, 1120b, respectively by a press fit, crimp, or spot laser welding. Crimping can be done around the entire perimeter of the bar, at two (opposing) sides of the bar, or at a single point along the perimeter of the bar.

Figure 28A:
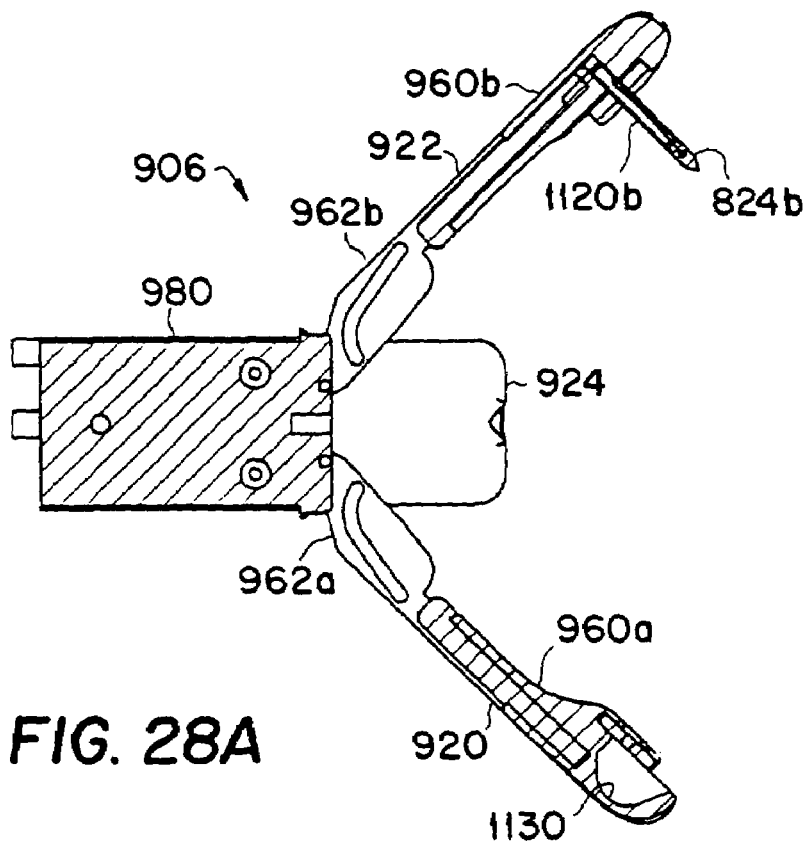
FIGS. 28A-28C illustrate deployment of the implant bar of FIG. 27.
Figure 28B:
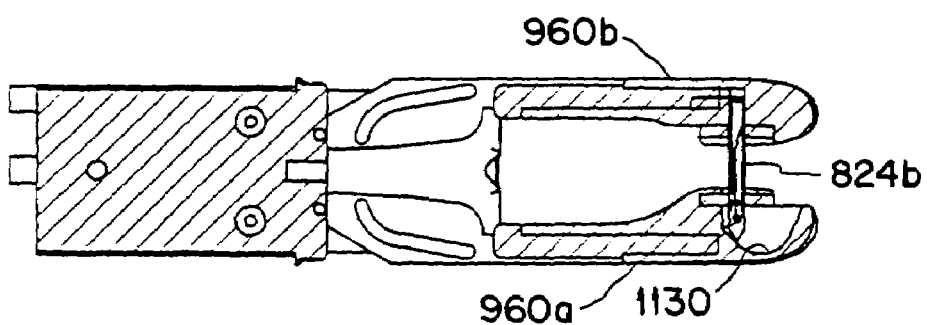
Figure 28C:
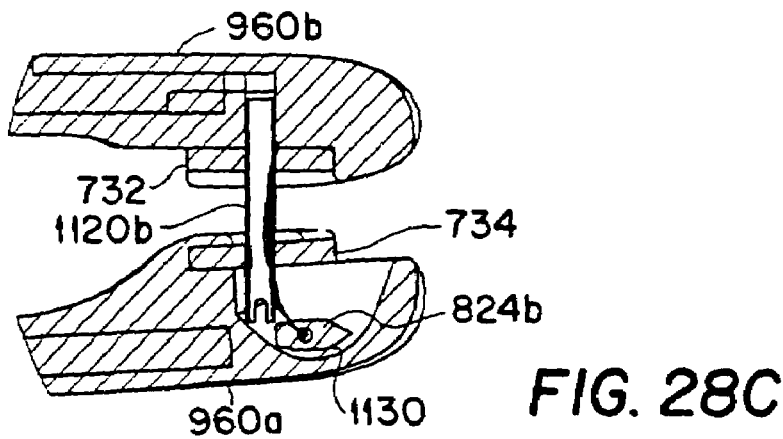

Bars 824a, 824b are configured to detach from tubes 1120a, 1120b under the force applied by the closing of jaws 920, 922. Referring to FIGS. 26 and 28A-28C, cartridge 960a defines two arcuate walls 1130 against which bars 824a, 824b are positioned upon closing of jaws 920, 922. As shown in FIG. 28C, upon closure of jaws 920, 922, the arcuate walls 1130 apply a lateral force (i.e., substantially normal to the long axis of the tubes) to bars 824a, 824b, which causes the bars to be released from the respective tubes. When jaws 920, 922 are opened, and instrument 900 pulled proximally, bars 824a, 824b and parts 732, 734 (discussed above with reference to FIG. 8) of the tissue fixation member are released from jaws 920, 922.

Figure 29A:
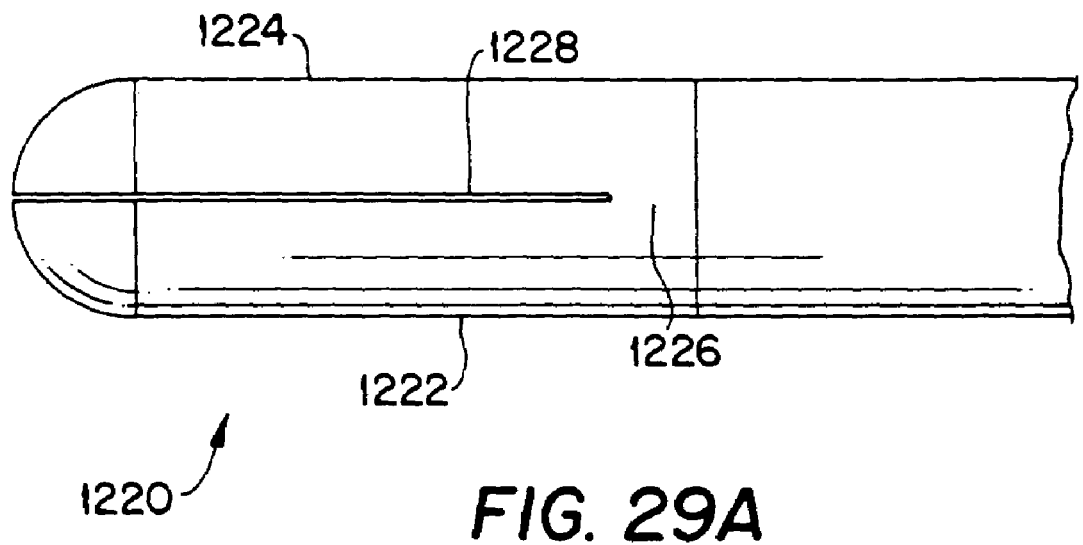
FIGS. 29A and 29B are illustrations of the hood member with the jaw members closed and open, respectively.
Figure 29B:
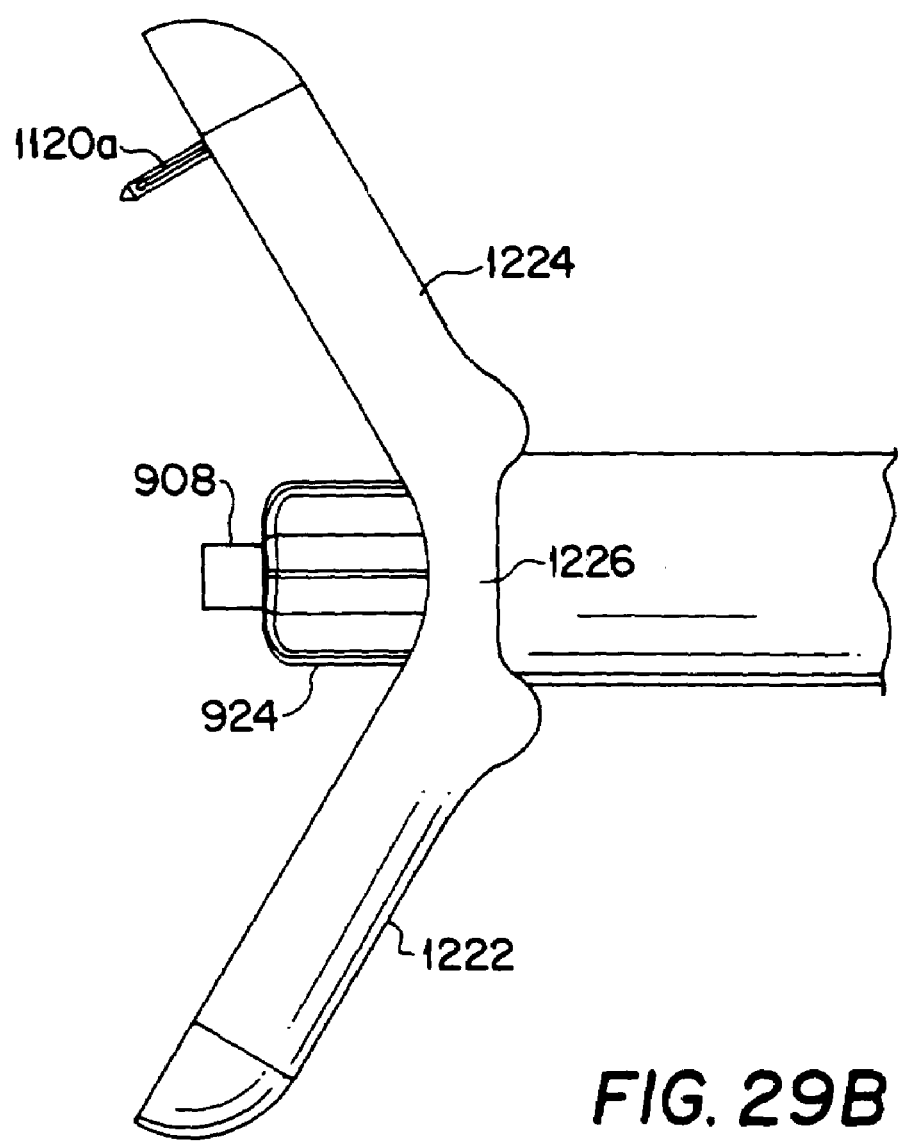

Referring to FIGS. 29A and 29B, jaws 920, 922 are covered with hood 1220 formed from halves 1222 and 1224 connected at a region 1226 and defining a seam 1228 therebetween. Each half 1222, 1224 covers a respective jaw 920, 922. When the jaws are closed, as shown in FIG. 29A, hood 1220 provides an atraumatic distal end for delivery through the esophagus. When the jaws are opened, as shown in FIG. 29B, halves 1222, 1224 separate at seam 1228. Hood 1220 limits trauma to the tissue during transoral insertion of the instrument and eliminates the need for an outer sheath extending the length of the instrument.

Referring to FIG. 30, handle 902 defines an inlet 1002 through which gastroscope 715 is introduced. Located at inlet 1002 is a seal 1004 for providing a hermetic seal between handle 902 and gastroscope 715. Seal 1004 has a sealing area 1006 of restricted diameter, and an alignment area 1008 of restricted diameter spaced about 10 mm from area 1006. Area 1006 has a diameter of about 9 mm, which is about the same or slightly smaller than (about 90% of) the diameter of gastroscope 715 (typically about 10 mm). Area 1008 has a diameter of about 11 mm, which is also about the same or slightly larger than (about 110% of) the diameter of gastroscope 715. Alignment area 1008 provides support for gastroscope 715 to maintain a hermetic seal at sealing area 1006 during motion of the gastroscope. Seal 1004 is made from, e.g., rubber or other deformable material.

Other embodiments are within the scope of the following claims.

For example, referring to FIG. 31, instead of curved surfaces 1130 of FIG. 28, cartridge 960a' includes a spring member 1130'. When bars 824a, 824b contacts members 1130', member 1130' deflects forming a curved surface resulting in a lateral force being applied to bars 824a, 824b that acts to dislodge the bars from needles 1120a, 1120b.

Referring to FIG. 32, in an alternative embodiment, tubes 1120' include a pair of radially opposed slots 1132 that impart flexibility to end 1133 of the tube to aid in release of the bars from the tubes. Bars 824' can include a pair of guide nubs 1134 received in slots 1132 to radially orients bars 824' relative to tubes 1120'. Referring to FIG. 33, bars 824" include a bump or undercut 1136 that determine the force needed to remove the bars from the tubes. The tubes can be formed from plastic and molded as an integral component of the cartridges, and the bars can be insert molded into the tubes. Referring to FIG. 34, bars 824''' are connected to tubes 1120'' by a weak area 1137 of decreased diameter that breaks upon application of lateral force to bars 824'''.

Referring to FIGS. 35A and 35B, instead of bars attached by suture, the tissue fixation member includes bars 1150 connected by a flexible spanning member 1152. Bars 1150 define through bores 1154 and are received on members 1156 having tissue penetrating tips 1158. Members 1156 replace tubes 1120.

Figures 36A, 36B:
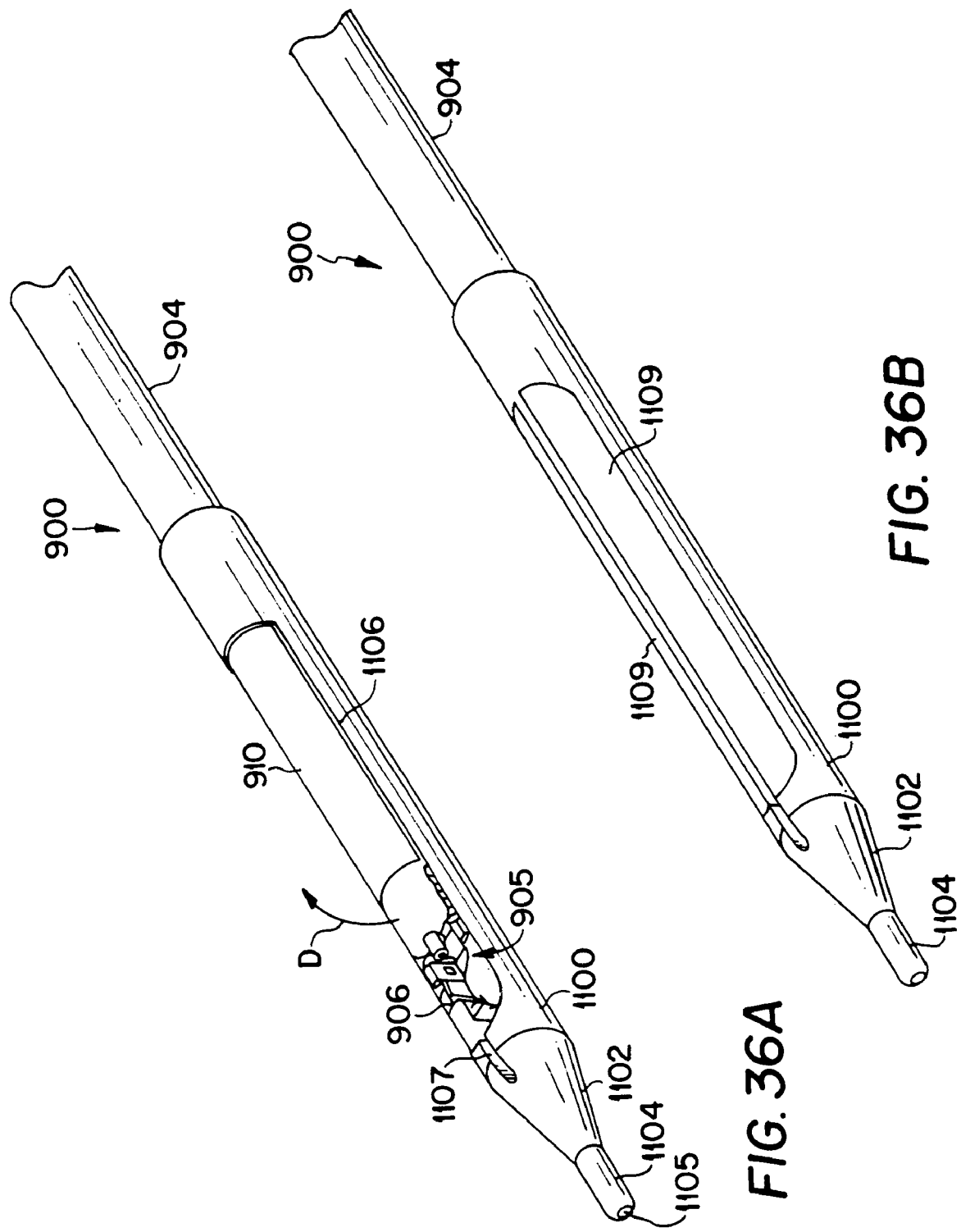

Referring to FIG. 36A, to aid in insertion of instrument 900 through the esophagus, end effector 906 and retroflex portion 910 are partially covered with an atraumatic hood 1100. Hood 1100 has a tapered distal end 1102 terminating in a small diameter lead portion 1104. Hood 1100 includes an opening 1106 through which end effector 906 and retroflex portion 910 are deployed, in the direction of arrow, D, after insertion of instrument 900 through the esophagus. Distal end 1102 defines a channel 1105 extending from lead portion 1104 to a slot 1107. Instrument 900 can be introduced transorally over a guidewire (not shown) by threading the guidewire through channel 1105 entering at lead portion 1104 to exiting at slot 1107. Hood 1100 is made from, e.g., metal, plastic, or elastomeric materials such as rubber, polyurethane or silicone.

As shown in FIG. 36B, to further ensure trauma to tissue as the instrument is introduced transorally is avoided, a pair of flaps 1109 are provided covering assembly 905. The flaps part when retroflex portion 910 is deployed.

Figure 37:
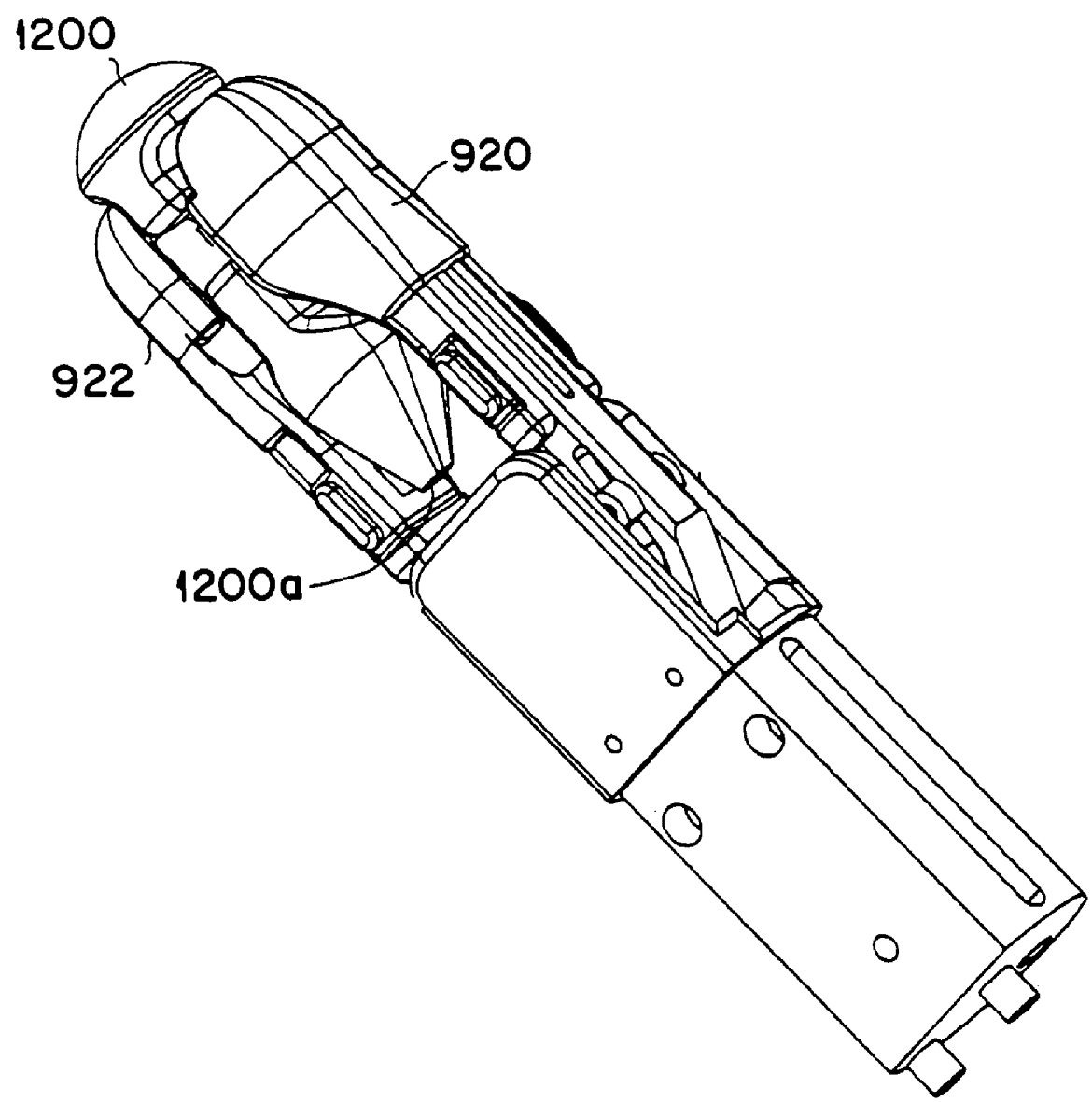

Referring to FIG. 37, rather than a hood covering end effector 906, placed between jaws 920, 922 is volume-filling bullet 1200 that creates a relatively smooth surface at the distal end of the instrument to facilitate insertion of the instrument into a patient. Bullet 1200 defines a through hole 1200a for delivery over a guidewire. Volume-filling bullet 1200 can be dissolvable in the operating environment, retrievable from the operating environment, or abandonable in the operating environment. For example, the guidewire can have a tip with a larger diameter than hole 1200a such that bullet 1200 is retained on the guidewire and removable therewith.

Figure 38:
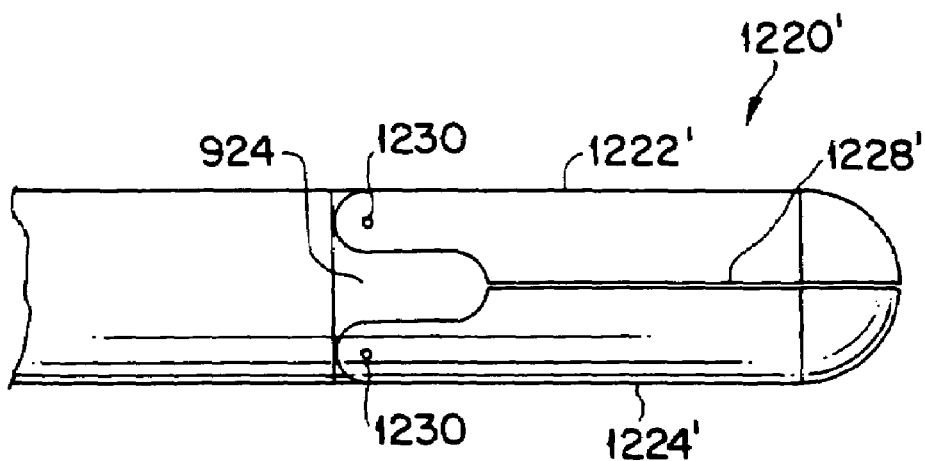
Figure 39:
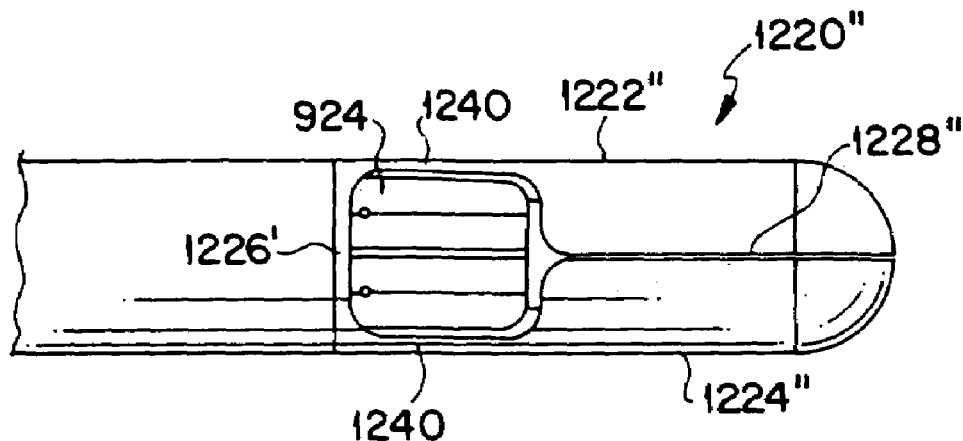

Referring to FIG. 38, in another embodiment, a hood 1220' includes halves 1222', 1224' that are connected to mount 924 at pivots 1230. When the jaws are opened, halves 1222', 1224' pivot about pivots 1230 to separate at seam 1228'. In FIG. 39, halves 1222'', 1224'' of a hood 1220'' include spring beams 1240 joined in a region 1226'. When the jaws are opened, halves 1222'', 1224'' separate at seam 1228'' and spring beams 1240 deform.

Figure 40:
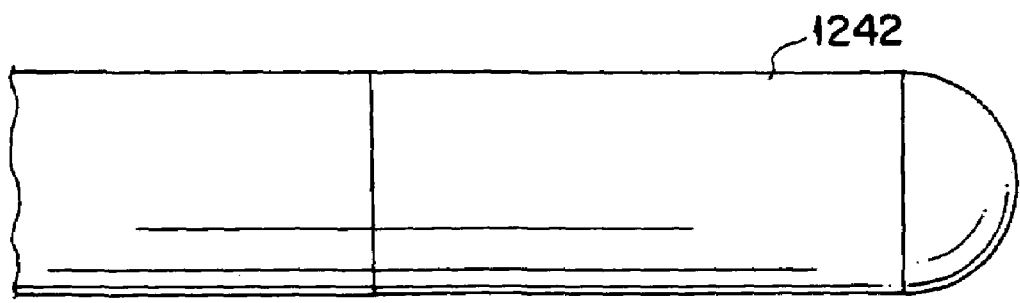

Alternatively, as shown in FIG. 40, to provide an atraumatic distal end, an end cap 1242 is placed over the jaws. End cap 1242 can be removed by pushing it off distally using the tissue engagement member, can be dissolvable (e.g., made out of starch or gelatin), or can "break-away" when the jaws are opened. Providing a perforation along the length of cap 1242 can aid in break-away. After removal, cap 1242 can be abandoned in the operating environment, where it is dissolved or passed, or it can be retained by a guidewire so that it is withdrawn when the instrument is withdrawn.

Figure 41A:
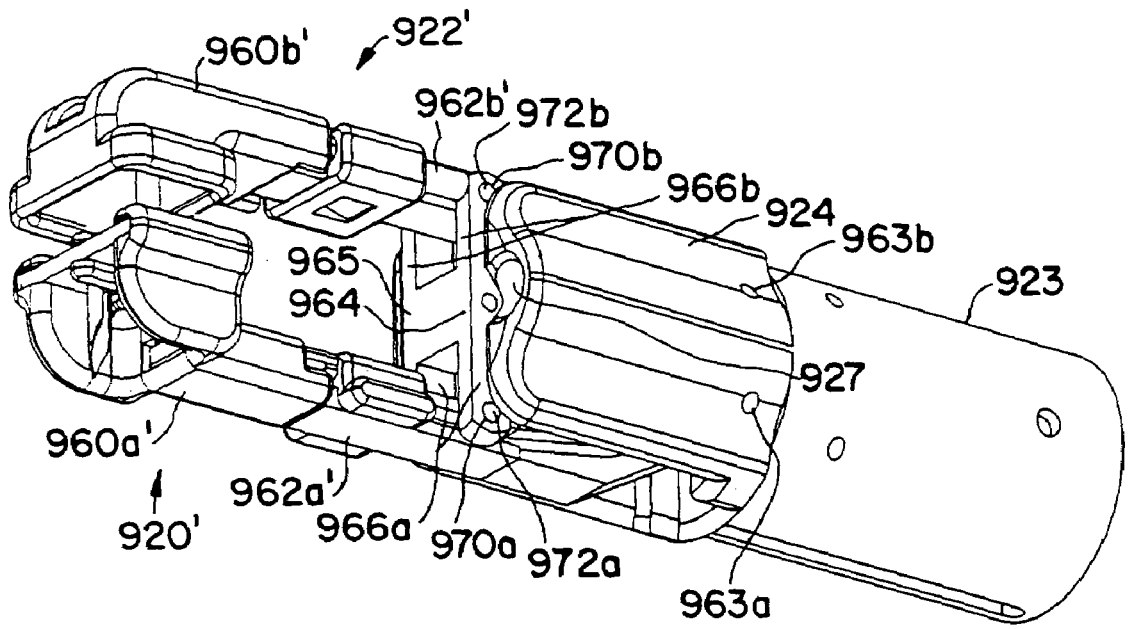
FIG. 41A is an isometric view and FIG. 41B is a side view in partial cross-section of an alternative embodiment of an end effector.
Figure 41B:
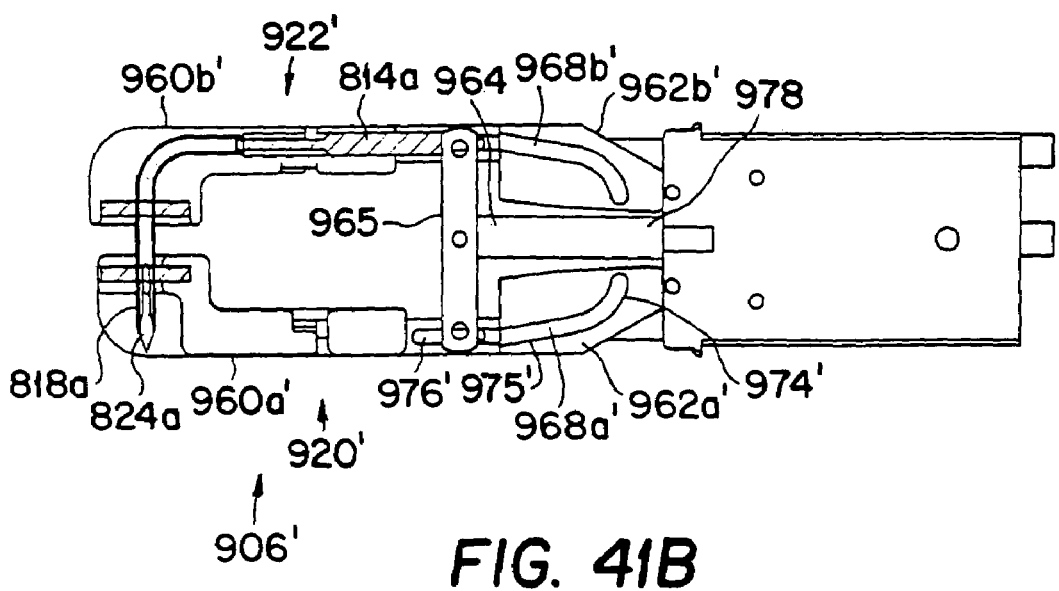

Referring to FIGS. 41A and 41B, in an alternative embodiment, an end effector 906' includes jaw members 920', 922', each of which includes a tissue manipulating cartridge 960a', 960b', respectively, releasable mounted to a respective actuating arm 962a', 962b'. Jaw 922' contains a pusher rods 814a, 814b for deploying bars 824a, 824b as described above with reference to FIG. 5. However, rather than employing a separate mechanism for actuating pusher rods 814a, 814b, pusher rods 814a, 814b are actuated by yoke 964. Each arm 962a', 962b' defines a slot 968a', 968b'' having a first arcuate section 974', a second generally linear, angled section 975', and a third generally linear, parallel section 976'. Movement of yoke 964 along slot sections 974' and 975' closes jaws 920', 922'. To deploy tissue fixation device 730 (FIG. 2), movement of yoke 964 along section 976' of slots 968a, 968b moves pusher rods 814a, 814b distally advancing bars 824a, 824b out of tissue penetrating tips 818a, 818b to deploy fixation device 730, as described above with reference to FIGS. 4A and 4B.

Figure 42:
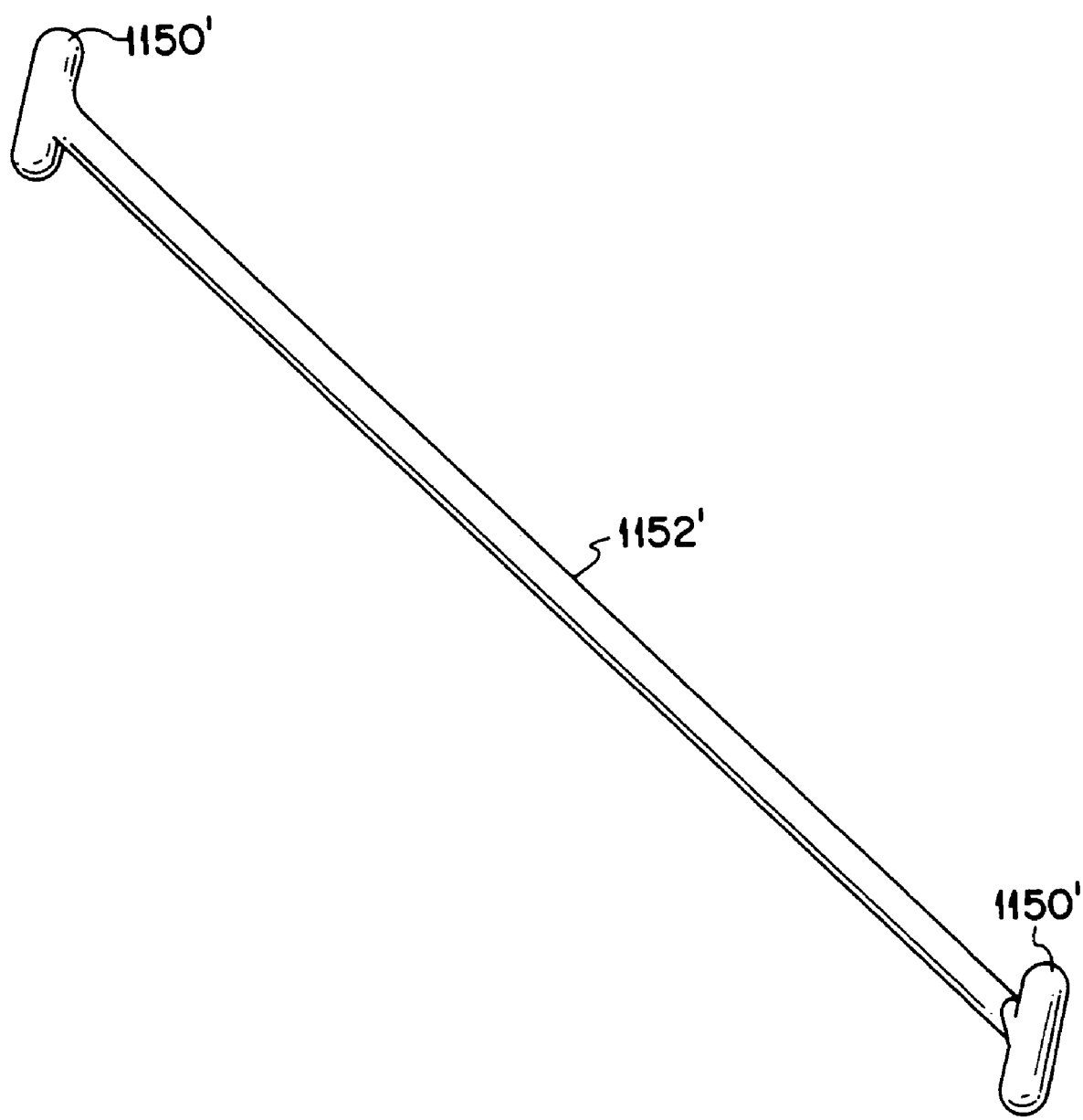
FIG. 42 is an illustration of a tissue fixation device for use with the end effector of FIG. 41.

Referring to FIG. 42, an alternative tissue fixation member for use with the embodiments of FIGS. 2 and 41, includes bars 1150' connected by a flexible spanning member 1152.' Bars 1150' replace bars 824a, 824b.

Figure 43:
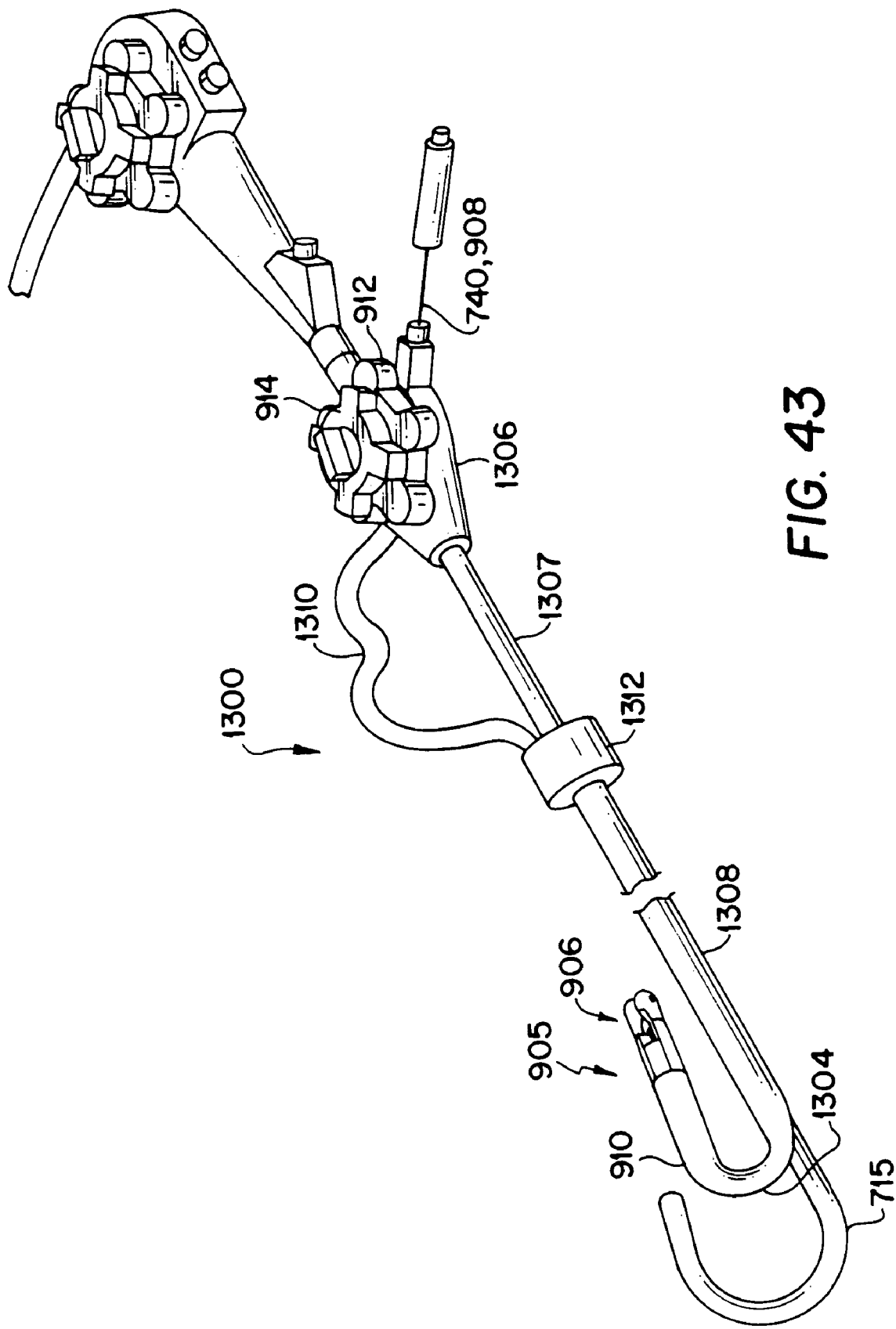
FIGS. 43-45 are illustrations of alternative configurations of an instrument for reconfiguring tissue.
Figure 44:
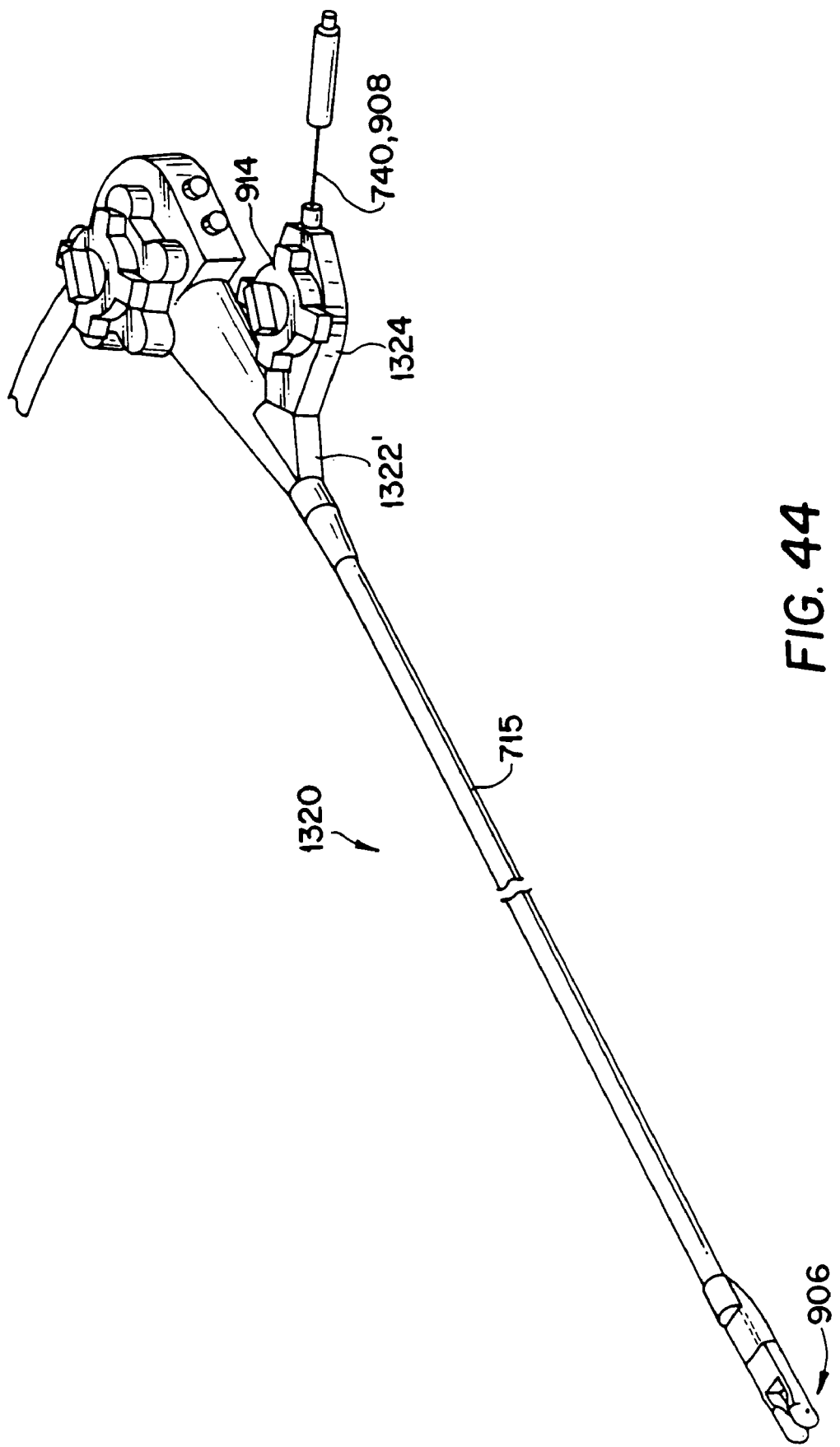
Figure 45:
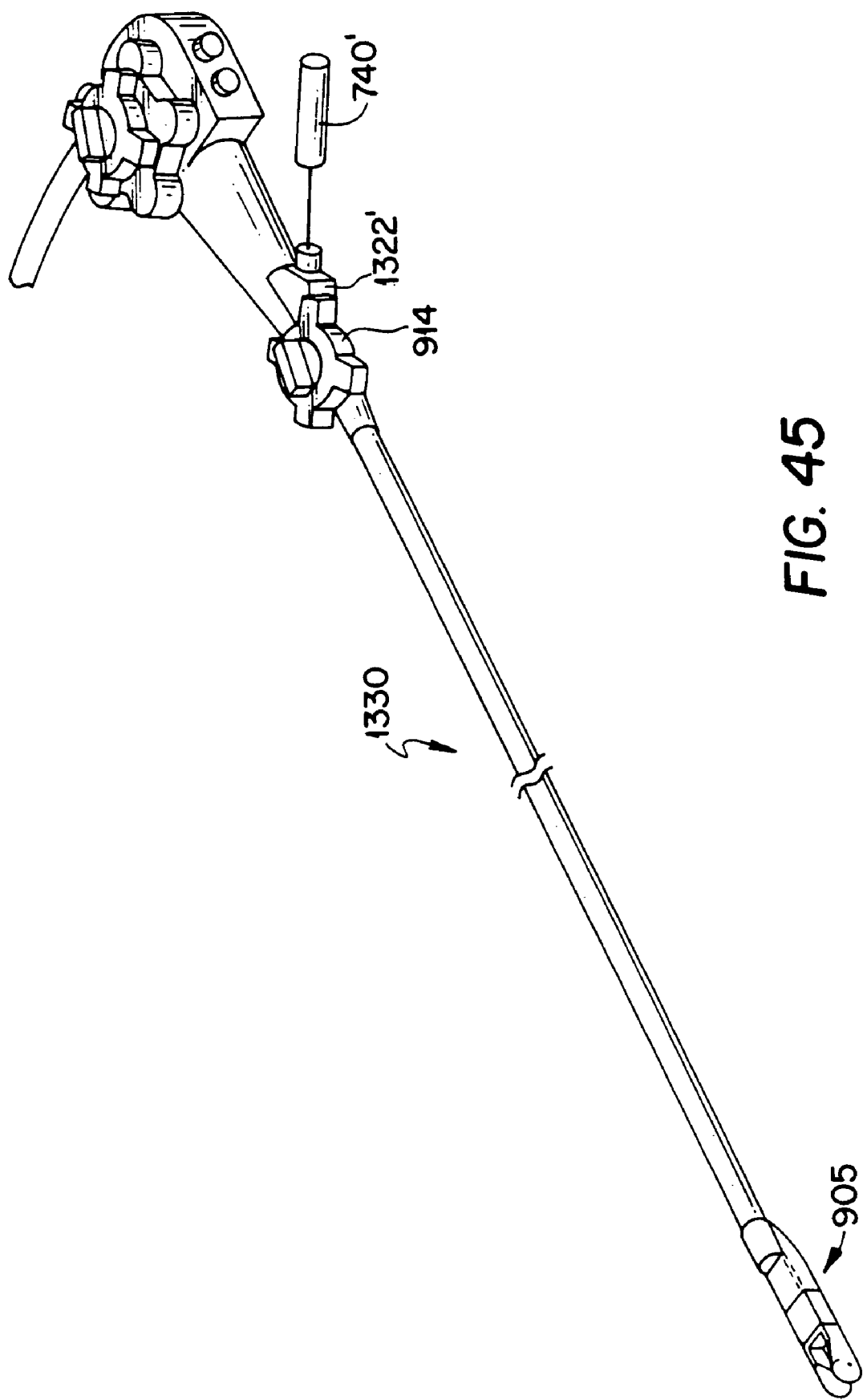

The instruments embodied in FIGS. 43-45 are configured to allow one person to control both the gastroscope and the tissue reconfiguring instrument. Referring particularly to FIG. 43, an instrument 1300 for reconfiguring tissue includes a standard gastroscope 715 and a tissue manipulator 1304 mounted to gastroscope 715. Tissue manipulator 1304 includes a control mount 1306 which the user mounts to gastroscope tube 1307 by, e.g., a friction fit. Control mount 1306 includes knobs 912, 914, described above. End effector 906 and retroflex portion 910 of assembly 905 are mounted to a sleeve 1308 through which gastroscope tube 1307 extends. Sleeve 1308 defines conduits for the control cables as described above. Connecting control mount 1306 and sleeve 1308 is a flexible conduit 1310 enclosing the various cables for controlling end effector 906 and retroflex portion 910, as discussed above. Sleeve 1308 includes a hand grip 1312. Conduit 1310 permits axial movement of gastroscope 715 relative to tissue manipulator 1304. In use, the operator holds the gastroscope handle with one hand, and operates all the controls and manipulates grip 1312 with the other hand, permitting a single operator to control all functions.

Referring to FIG. 44, an instrument 1320 for reconfiguring tissue includes a standard gastroscope 715 to which the user mounts end effector 906. Cables for actuating the jaws are attached to a jaw control mount 1324. The cables are received in the standard biopsy channel 1322' of the gastroscope. Retroflexing action is provided by gastroscope 715 and is controlled by the gastroscope controls. Jaw control mount 1324 includes knob 914 for actuating the jaw control cables. In the embodiment of FIG. 45, rather than mounting the tissue reconfiguring instrument to a standard gastroscope, an integral instrument 1330 includes a knob 914 mounted directly to gastroscope 1330. The control cables for actuating the jaws are integrated with the gastroscope control cables. The tissue engaging member, e.g., member' 740' of FIG. 12, is introduced through the gastroscope channel 1322'.

Figure 46A:
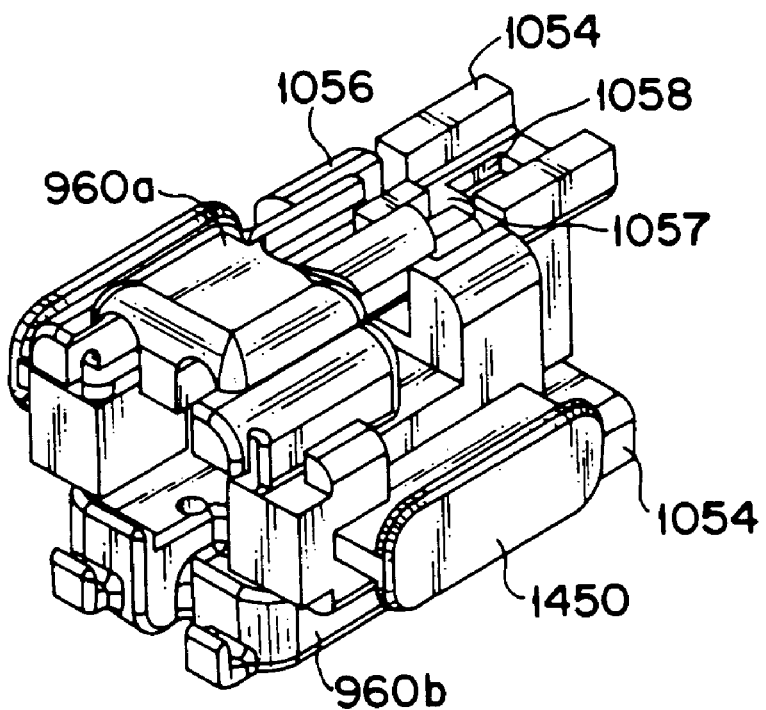
Figure 46B:
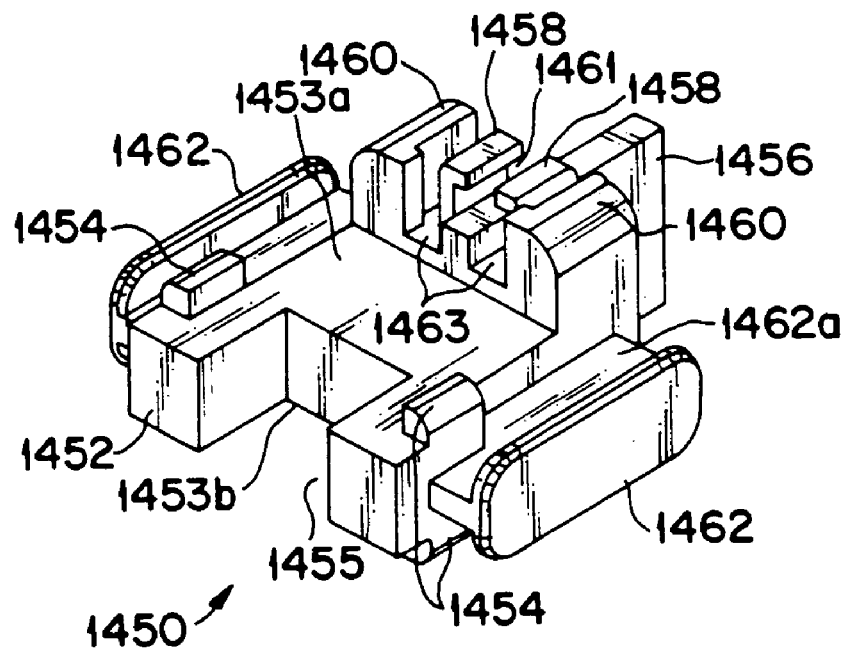
Figure 47B:
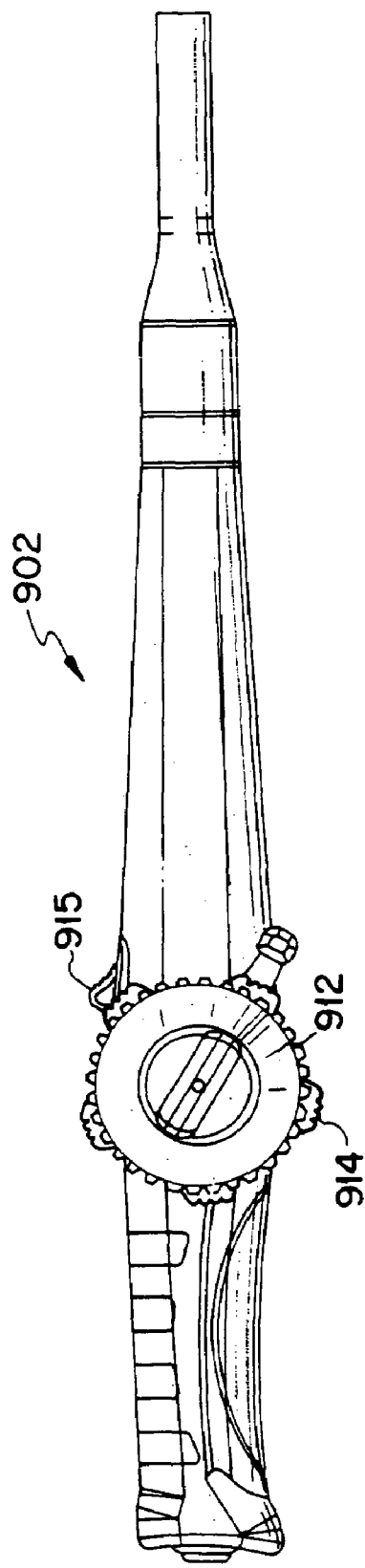
Figure 47C:
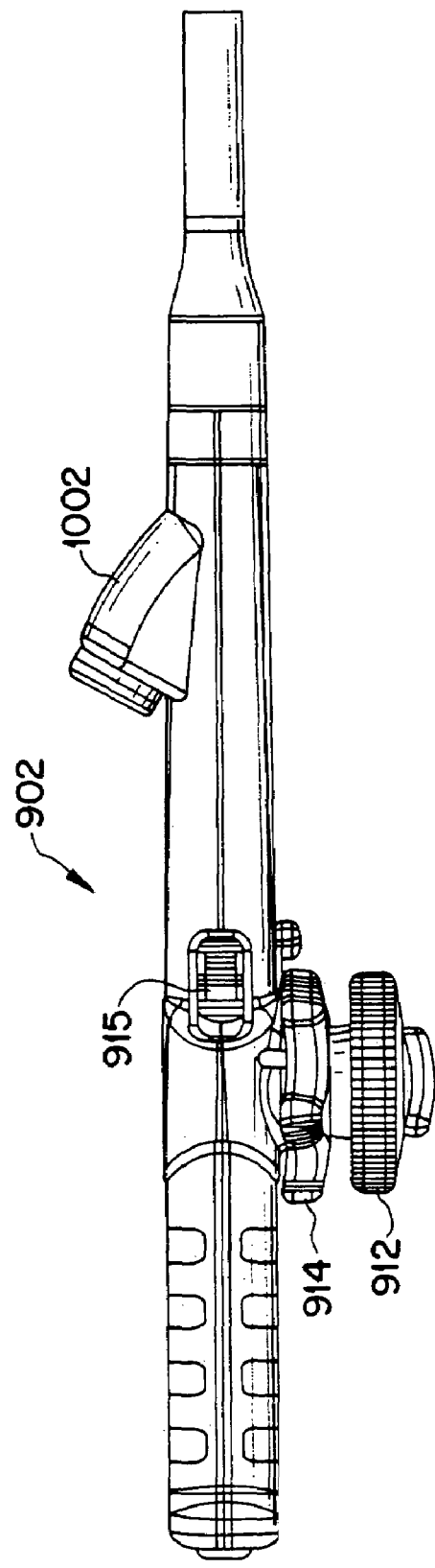
Figure 47F:
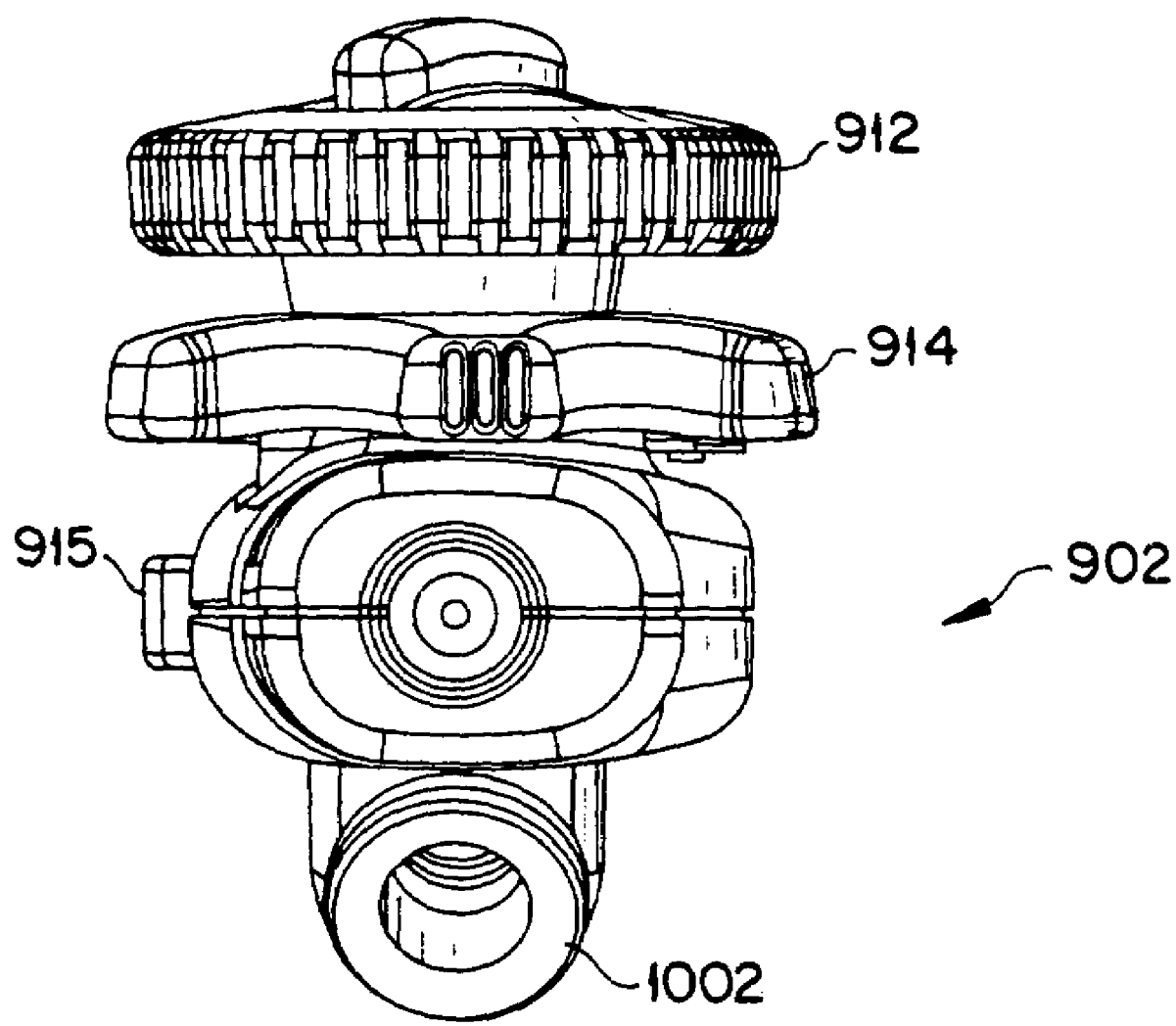

Referring to FIGS. 46A and 46B, cartridges 960a, 960b are supplied to the medical personnel in a holder 1450. Holder 1450 includes a base section 1452 having a first side 1453a for receiving head 1059 of cartridge 960a, and a second side 1453b for receiving head 1059 of cartridge 960b. Base section 1452 defines an opening 1455 where tubes 1120a, 1120b are located. Extending from either side of base section 1452 are two sets of detents 1454 that are positioned on either side of the cartridge head 1059. Extending proximally from base section 1452 is a fin 1456 with spring beams 1458 on either side of fin 1456 on both sides of base section 1452. Located on either side of spring beams 1458 are guide rails 1460. Between the spring beams is a slot 1461 and between each spring beam 1458 and guide rail 1460 is a slot 1463. Holder 1450 includes finger grips 1462 for ease of handling. Hood 1220 is provided to the user with holder 1450. To allow the user to hold finger grips 1462, finger grips 1462 are attached to the remainder of the holder by a thin section 1462a over which the slot in the hood is positioned.

To load cartridges 960a, 960b in holder 1450, each cartridge is in turn positioned over base section 1452 with thin section 1057 of the cartridge aligned with slot 1461. By pushing down on the cartridge, spring beams 1458 are forced apart and thin section 1057 snaps into place in slot 1461, with spring beams 1458 holding the cartridge in place. Cartridge head 1059 is located between detents 1454, and side walls 1056 are partially within slots 1463 to align the cartridge and help hold the cartridge in position. With base section 1452 located between cartridges 960a, 960b, the cartridges are spaced such that the implant will not deploy (corresponding to the position shown in FIG. 23C).

Referring also to FIG. 46C, to attach cartridges 960a, 960b to arms 962a, 962b, respectively, while holding finger grips 1462, the user slides the cartridges over the arms (with the arms positioned as shown in FIG. 23C). Initially, formation 1051 on the inner surfaces of the arms slide between spring beams 1458 forcing the spring beams apart. Further sliding of the cartridge over the arms, positions rectangular member 1050 under arms 1056 and locates clip 1052 in hole 1058. The cartridges are now attached to the arms. Because spring beams 1458 have been forced apart by formation 1051, holder 1450 can now be released from cartridges 960a, 960b by opening the jaws and the instrument is ready for use.

Holder 1450 is preferably formed from plastic, and holder 1450 with cartridges 960a, 960b, hood 1220 and the implant are supplied to the surgical personnel in a sterile condition.

FIGS. 47A-47F are various views of handle 902.

What is claimed is:

1. A method comprising:
   puncturing stomach tissue from within the stomach with a piercing member;
   pulling the piercing member into a pair of coacting jaws to pull the punctured tissue into the pair of coacting jaws;
   engaging the punctured stomach tissue with the pair of coacting jaws from within the stomach; and
   piercing the stomach tissue with at least one of the jaws.

2. The method of claim 1 wherein the at least one jaw includes an implant that pierces the tissue.

3. The method of claim 2 wherein the at least one jaw includes a tissue piercing element that delivers at least a portion of an implant.

4. The method of claim 1 wherein the jaws are configured to deploy an implant into the stomach tissue.

5. The method of claim 1 wherein engaging stomach tissue includes placing parts of a tissue fixation device coupled to the jaws in contact with the stomach tissue.

6. A method of treatment comprising:
   puncturing stomach tissue with a piercing member from within the stomach;
   pulling the piercing member into a plurality of members to pull the punctured stomach tissue into the plurality of members;
   engaging the pierced stomach tissue with a plurality of members from within the stomach; and
   moving at least one of the plurality of members to place exterior surface regions of the stomach in apposition.

7. The method of claim 6 wherein engaging includes piercing the stomach tissue with the plurality of members.

8. The method of claim 6 further comprising fixing the exterior surface regions of the stomach to each other.

9. The method of claim 8 wherein fixing includes placing at least one tissue fixation device through at least one full-thickness layer of the stomach.

10. The method of claim 8 wherein fixing includes delivering a tissue fixation device to the stomach tissue while the stomach tissue is engaged.

11. The method of claim 6 wherein engaging includes applying pressure to the stomach tissue.

12. The method of claim 6 wherein engaging includes pulling the stomach tissue into a tissue securing device.

13. The method of claim 12 further comprising securing the exterior surface regions using the tissue securing device.

14. A method of treatment comprising:
   piercing stomach tissue with a coil from within the stomach;
   pulling the coil to reposition the pierced stomach tissue;
   engaging the pierced stomach tissue with at least one of a plurality of members from within the stomach;
   moving the plurality of members to place exterior surface regions of the stomach in apposition; and
   fixing the exterior surface regions of the stomach to each other.

15. The method of claim 14 wherein engaging includes piercing the stomach tissue with the plurality of members.

16. The method of claim 14 wherein fixing includes placing at least one tissue fixation device through at least one full-thickness layer of the stomach.

17. The method of claim 14 wherein fixing includes delivering a tissue fixation device to the stomach tissue while the stomach tissue is engaged.

18. The method of claim 14 wherein engaging includes applying pressure to the stomach tissue.

19. The method of claim 14 wherein engaging includes pulling the stomach tissue into a tissue securing device.

20. The method of claim 19 further comprising securing the exterior surface regions using the tissue securing device.

* * * * *